(12) United States Patent
MacArthur

(10) Patent No.: US 12,035,952 B1
(45) Date of Patent: Jul. 16, 2024

(54) RADIAL INCLINATION VOLAR ANGLE RESTORATION PLATE

(71) Applicant: Robert MacArthur, Signal Hill, CA (US)

(72) Inventor: Robert MacArthur, Signal Hill, CA (US)

(\*) Notice: Subject to any disclaimer, the term of this patent is extended or adjusted under 35 U.S.C. 154(b) by 0 days.

(21) Appl. No.: 18/447,296

(22) Filed: Aug. 9, 2023

Related U.S. Application Data

(63) Continuation of application No. 18/352,236, filed on Jul. 13, 2023.

(51) Int. Cl.
*A61B 17/80* (2006.01)
*A61B 17/68* (2006.01)
*A61B 17/84* (2006.01)

(52) U.S. Cl.
CPC ...... *A61B 17/8061* (2013.01); *A61B 17/8052* (2013.01); *A61B 17/808* (2013.01); *A61B 17/842* (2013.01); *A61B 17/68* (2013.01); *A61B 17/8028* (2013.01); *A61B 17/8095* (2013.01)

(58) Field of Classification Search
CPC .............. A61B 17/8061; A61B 17/808; A61B 17/8028; A61B 17/8095; A61B 17/8052; A61B 17/842; A61B 17/809; A61B 17/8057; A61B 17/8605; A61B 17/8085; A61B 17/82; A61B 17/68
USPC .............................. 606/280, 70–71, 281–299
See application file for complete search history.

(56) References Cited

U.S. PATENT DOCUMENTS

| | | | |
|---|---|---|---|
| 9,833,270 B2 | 12/2017 | Zlotolow | |
| 2007/0276383 A1* | 11/2007 | Rayhack | A61B 17/8057 606/86 B |
| 2012/0078252 A1* | 3/2012 | Huebner | A61B 17/808 606/70 |

OTHER PUBLICATIONS

"Lever Action Plate System", Mcginley Orthopedics, retrieved from https://www.mcginleyorthopedicinnovations.com/lever-action-plate-system.

\* cited by examiner

*Primary Examiner* — Marcela I. Shirsat
(74) *Attorney, Agent, or Firm* — John M. Rogitz

(57) ABSTRACT

A radial inclination volar angle restoration plate includes a shank and a window portion. The plate also includes holes for accepting bone fasteners, as well as holes for accepting respective pegs from distal and radial pads. The pads are engageable with the plate via the pegs and can guide an osteotome extending through a window of the window portion to help reduce a bone fracture. The plate, fasteners, pads, and/or osteotome may be included together in a kit.

20 Claims, 47 Drawing Sheets

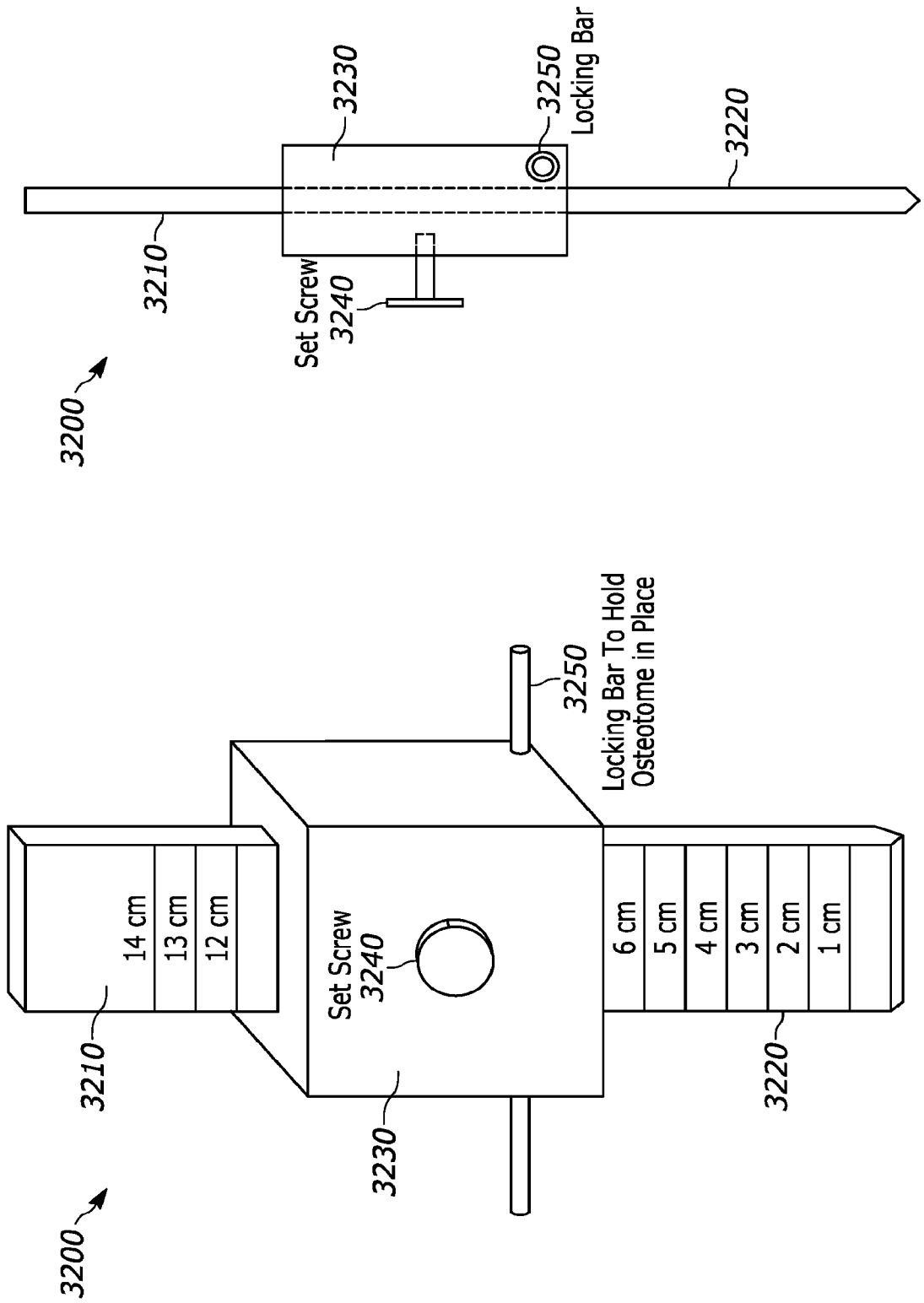

Reduction Chart

| Pad Thickness | Osteotome Excursion ∠ | Dorsal Cortical Correction (Lengthening) | True Dorsal Cortical Correction | Volar Cortical Correction (Lengthening) | True Volar Cortical Correction |
|---|---|---|---|---|---|
| No Pad (Just 0.2 cm Thickness Of Plate) | 30° | 1.15 cm | 0.76 cm | 0.12 cm | 0.08 cm |
|  | 45° | 2.0 cm | 1.32 cm | 0.20 cm | 0.13 cm |
| 0.5 cm Pad | 30° | 1.44 cm | 0.95 cm | 0.40 cm | 0.27 cm |
|  | 45° | 2.50 cm | 1.65 cm | 0.70 cm | 0.46 cm |
| 1.0 cm Pad | 30° | 1.73 cm | 1.15 cm | 0.69 cm | 0.46 cm |
|  | 45° | 3.00 cm | 2.00 cm | 1.20 cm | 0.79 cm |
| 2.0 cm Pad | 30° | 2.31 cm | 1.52 cm | 1.27 cm | 0.84 cm |
|  | 45° | 4.00 cm | 2.64 cm | 2.20 cm | 1.32 cm |

*True Correction = Calculated Correction − 30% To Compensate For Compressibility Of Bone

FIG.33

RADIAL INCLINATION VOLAR ANGLE RESTORATION PLATE

FIELD

The disclosure below relates generally to radial inclination volar angle restoration (RIVAR) plates for distal radius fracture reduction.

BACKGROUND

Distal radius fractures are among the most common orthopedic injuries. Different devices have been tried to reduce distal radius fractures. But as recognized herein, those devices are insufficient for a number of reasons. For instance, some devices cause inflammation and rupture of the extensor tendons on the back of the wrist, while other devices cause irritation and rupture of the flexor pollicis longus (FPL) tendon.

SUMMARY

The disclosure below therefore relates to radial inclination volar angle restoration plates for distal radius fracture reduction, helping to improve patient outcomes and quicken recovery time.

Accordingly, in one aspect a device includes a shank defining a proximal-distal dimension and formed with plural longitudinally-spaced holes for accepting respective bone fasteners. The device also includes a window portion made integrally with the shank and extending distally away from a distal end of the shank. The window portion defines a dorsal surface and a volar surface opposite the dorsal surface. The window portion also defines an ulna-radius dimension generally perpendicular to the proximal-distal dimension. The window portion includes an ulnar wall and a radial wall opposite the ulnar wall, with at least the radial wall tapering radially from the distal end of the shank. The window portion also includes a cross-member connecting distal ends of the radial and ulnar walls to form a window with an endless periphery between the walls and the cross-member. The cross-member is wider in the ulna-radius dimension than the shank.

In some example embodiments, at least a distal portion of the window portion may be angled or curved volarly.

Also in some example embodiments, the radial wall of the window portion may extend further radially than the ulnar wall extends ulnarly.

Additionally, if desired the device may include at least one pad removably engageable with the shank and/or with the window portion.

So, for example, the pad may include at least one peg engageable with a respective hole in the window portion. Here the pad may include a distal pad, where the distal pad may include a distal face that is at least partially curved or beveled distally. The distal pad may also include a proximal edge portion. The proximal edge portion may include a proximal edge establishing a lip, where the lip may extend in the ulna-radius dimension. The proximal edge portion may also include a proximal wall beveled distally, where the proximal wall of the proximal edge portion may be configured to engage an osteotome. In certain examples, the proximal wall may be beveled distally and also beveled radially, while in other examples the proximal wall may be beveled distally but not beveled in the ulnar-radial dimension.

The pad might also include at least one peg engageable with a respective hole in the shank in certain examples. The pad may thus include a proximal pad, where the at least one peg may extend from a dorsal side of the proximal pad. At least one extension element may extend from a volar side of the proximal pad and may be configured to engage a bar extending laterally from an osteotome. The proximal pad may also include a distal edge portion against which an osteotome can be disposed, where the distal edge portion may establish a fulcrum for the osteotome. In certain specific examples, plural pegs may extend from the dorsal side of the proximal pad and plural extension elements may extend from the volar side of the proximal pad. The plural extension elements may be spaced from each other, where each extension element may include a curved end portion. Each curved end portion may be configured for receiving a portion of one or more bars extending laterally from the osteotome.

Additionally, in some example embodiments the device may include at least one osteotome that may be configured to extend through the window portion to provide leverage to reduce a bone fracture.

Also if desired, the cross-member may include plural holes configured to accept at least one fixation wire.

In another aspect, a method includes providing a device that includes a shank defining a proximal-distal dimension and that includes a window portion made integrally with the shank. The window portion extends distally away from a distal end of the shank. The window portion also defines a window with an endless inner periphery, with the window portion being configured for extension of an osteotome through the window during fracture reduction. The method also includes implanting the device into a patient to reduce a fracture.

In certain example implementations, the method may include reducing the fracture at least in part by engaging at least one pad with the shank and manipulating the osteotome against the at least one pad to reduce the fracture.

In still another aspect, a device includes a shank defining a proximal-distal dimension and formed with plural longitudinally-spaced holes for accepting respective bone fasteners. The device also includes a window portion made integrally with the shank and extending distally away from a distal end of the shank. The window portion defines a dorsal surface and a volar surface opposite the dorsal surface. The window portion also defines an ulna-radius dimension generally perpendicular to the proximal-distal dimension. The window portion includes an ulnar wall and a radial wall opposite the ulnar wall. The window portion also includes a cross-member connecting distal ends of the radial and ulnar walls, with the window portion including a distal end portion that extends volarly and obliquely away from a proximal portion of the window portion. The window portion also includes at least a first hole configured to receive a first peg of a distal pad, and the shank includes at least a second hole configured to receive a second peg of a proximal pad. The first and second holes are different from each other and are different from the plural longitudinally-spaced holes.

The details of the present application, both as to its structure and operation, can best be understood in reference to the accompanying drawings, in which like reference numerals refer to like parts, and in which:

BRIEF DESCRIPTION OF THE DRAWINGS

FIGS. 32A and 32B show respective perspective and side elevational views of an example sliding osteotome consistent with present principles;

FIG. 33 shows an example reduction chart that may be used consistent with present principles.

DETAILED DESCRIPTION

Present principles recognize that there are generally four principle parameters for defining radius fracture displacement and subsequent realignment or "reduction": the length of the radius, alignment of the joint surface between the radius and the wrist or carpal bones, radial inclination related to the radial side of the radius being longer than the ulnar side, and volar tilt where the dorsal side of the radius is longer than the volar side (e.g., 10 degree tilt generally being considered normal/healthy). Many distal radius fractures involve one or more of shortening of the radius, decrease in the radial inclination, and dorsal angulation of the volar tilt or reversal of the tilt so that the dorsal side is shorter than the volar side.

To address these issues while helping minimize adverse side effects of reduction, present principles recognize that volar plates may be used, with the plate placed proximal to the "watershed line" and the volar tilt being restored. The watershed line itself may be the point where the distal radius flares in the volar direction. Absent present principles, restoration of the volar tilt is technically much more difficult using a volar surgical approach. Traction on the thumb and pressure on the radial side of the distal radius can restore the radial inclination. However, traction on the hand and pressure on the dorsal side of the wrist may not effectively restore the volar tilt. The dorsally impacted bone might be crushed on itself and can only be reduced with direct pressure on the dorsal side bone surface or by levering the distal fragment into normal tilt by passing a flat metal tool across the fracture from volar to dorsal and then levering the metal tool away from the wrist, thus restoring the volar tilt. But the distal volar edge of the radius should be held in place to allow leverage, and the reduction is often lost before it can be stabilized with a volar plate, absent present principles.

Figure 1:
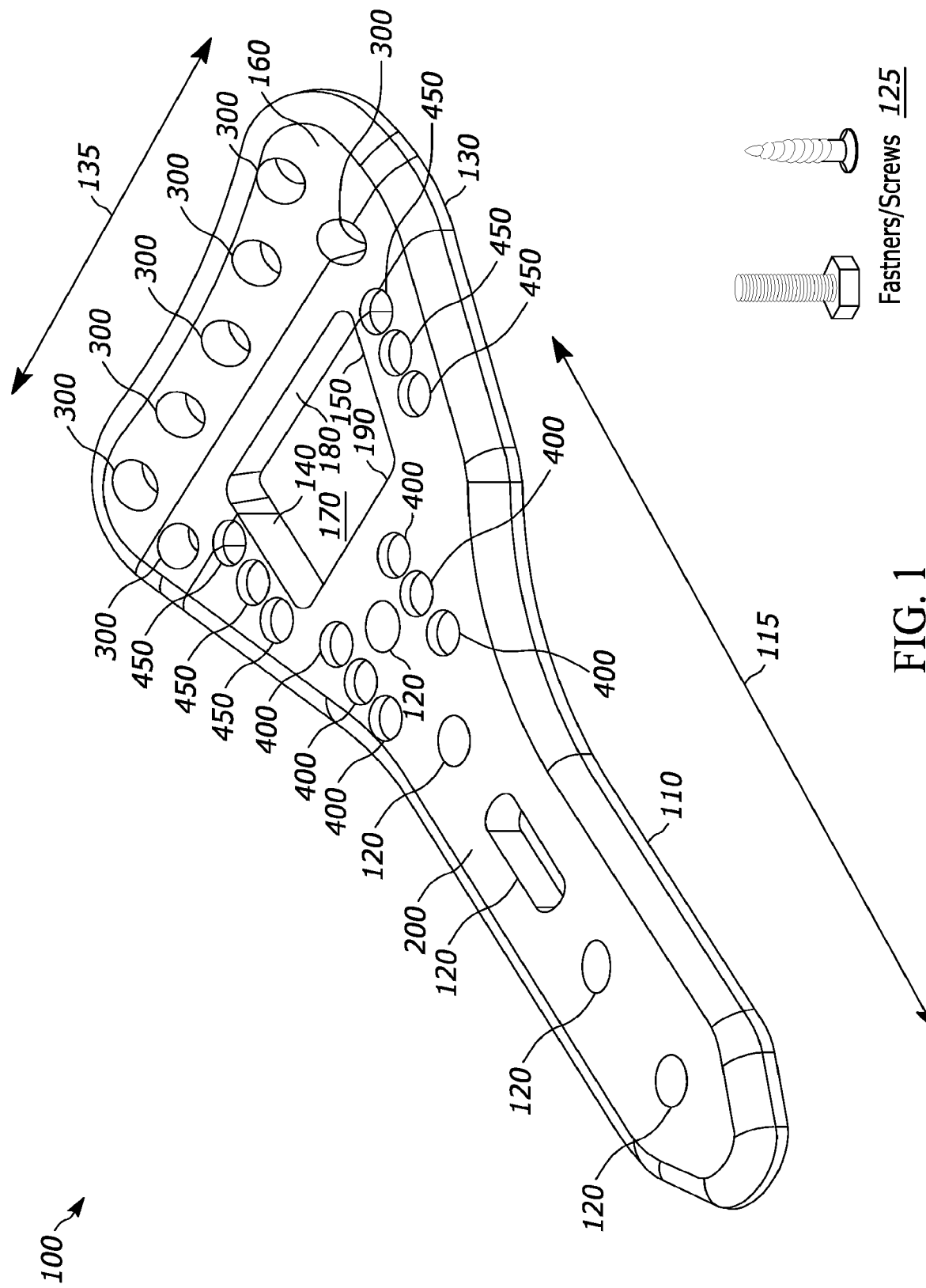
FIG. 1 illustrates an example embodiment of an example RIVAR plate in perspective view consistent with present principles.

Accordingly and now referring to FIG. 1, a perspective view is shown of a volar side/face 200 of an example radial inclination volar angle restoration (RIVAR) plate 100 consistent with present principles. Here, the RIVAR plate 100 is configured for a right arm/wrist but in either case may have volar to dorsal thickness of between 0.1 cm and 0.3 cm, and preferably 0.2 cm in certain non-limiting examples.

As shown in FIG. 1, the RIVAR plate 100 includes a shank 110 defining a proximal-distal dimension 115 and formed with plural longitudinally-spaced, coaxial holes 120 for accepting respective bone fasteners 125. If screws are used as the fasteners 125, the holes 120 may be threaded to engage the threads of the screws. If non-threaded fasteners are used, the holes 120 need not be threaded. Further note that the holes 120 are coaxial in this example according to an axis that is parallel to the longitudinal axis of the shank 110, and that the holes 120 are laterally central on the shank 110 itself.

The RIVAR plate 100 also includes a window portion 130 made integrally with the shank 110 and extending distally away from a distal end of the shank 110. The window portion 130 defines a dorsal surface and a volar surface opposite the dorsal surface, as well as defining an ulna-radius dimension 135 generally perpendicular to the proximal-distal dimension 115.

As also shown in FIG. 1, the window portion 130 includes an ulnar wall 140 and a radial wall 150 opposite the ulnar wall 140. At least the radial wall 150 may taper radially away from the distal end of the shank 110 as shown in FIG. 1, with the degree of taper varying depending on implementation. In various examples, the degree of taper might be ten to fifteen degrees.

Additionally, a cross-member 160 may be integrally formed as part of the portion 130. The cross-member 160 may connect distal ends of the walls 140, 150 to form a window 170 with an endless inner periphery between the walls 140, 150 and the cross-member 160. Note here that the cross-member 160 may be wider in the ulna-radius dimension 135 than the shank 110. And also note here that the length of the plate 100 itself may vary depending on the size of the patient's distal radius.

As also shown in FIG. 1, due to the taper mentioned above, the radial wall 150 of the window portion 130 may extend further radially than the ulnar wall 140 may extend ulnarly. Thus, in some examples, the ulnar wall 140 may extend from proximal to distal along an axis that is parallel to the longitudinal axis of the plate 100 as defined the proximal-distal dimension 115, while the radial wall 150 may extend obliquely toward a radial side of the plate 100 according to the ulna-radius dimension 135.

Figure 2:
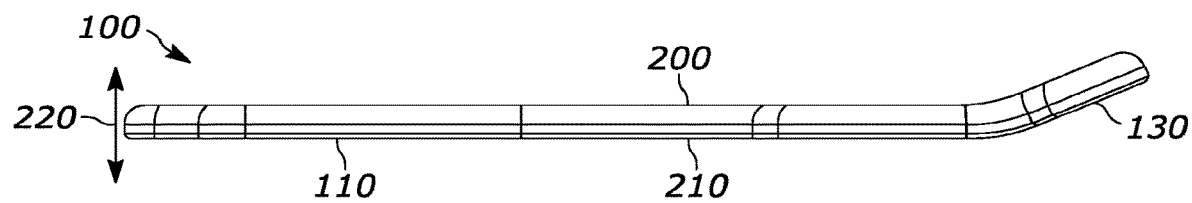
FIG. 2 shows the example RIVAR plate in side elevational view.

As better shown in the side elevational view of FIG. 2 (with the volar face 200 facing up and a dorsal face 210 facing down according to this perspective), a distal end portion of the window portion 130 may be angled or curved volarly as shown according to a dorsal-volar dimension 220. The curve of the portion 130 may begin longitudinally on the plate 100 at a point that is at or within a few millimeters of a distal wall 180 of the window portion 130 (the wall 180 also being shown in FIG. 1 and defining a distal boundary of the window 170). Thus, the distal-most centimeter or two centimeters of the plate 100 may be angled volarly in certain examples to conform to the volar flare of the distal radius. And note for completeness that the portion 130 may also include a proximal wall 190 as also shown in FIG. 1, with the wall 190 defining a proximal boundary of the window 170 and helping to establish the endless inner periphery of the window 170 along with the other window walls.

As alluded to above, the degree of volar inclination that results from the volar curve of the distal end segment of the window portion 130, relative to the longitudinal axis of the plate 100, may be an amount suitable to conform to the degree of inclination of a majority of patients' volar side of the distal radius (sometimes referred to as the "volar flare"). As such, the volar-tilted distal end of the plate 100 may establish an angle between eighteen and twenty-two degrees relative to the longitudinal axis of the plate 100, and preferably an angle of twenty degrees relative to the longitudinal axis of the plate 100 in non-limiting example embodiments.

Note here that the RIVAR plate 100 itself, including the shank 110 and window portion 130, may be integral and rigid. The plate 100 may be made of titanium, titanium alloy, stainless steel, cobalt chrome, iron, cobalt, chromium, other metal alloys, tantalum, polyethylene, acrylic, other polymers/plastics, and/or ceramics etc.

Also note here that while a right arm/wrist iteration of the RIVAR plate 100 is shown, it is to be understood that the RIVAR plate 100 may have different iterations for left and right arms according to the principles above while still maintaining radial taper of the radial wall 150 toward the radius, and with the radial wall 150 still extending further radially than the ulnar wall 140 extends ulnarly. But regardless of left or right arm configuration, the window portion 130 (e.g., at least a distal end portion thereof) may still be angled or curved volarly as described above, though the degree of the angle and shape of the curve/angle may vary depending on implementation as well.

Additionally, it is to also be understood the shank 110 itself may be configured wider or narrower in the ulna-radius dimension 135 depending on implementation/patient, and that the length of the shank 110 and/or overall length of the RIVAR plate 100 may also vary depending on implementation/patient.

Figure 3:
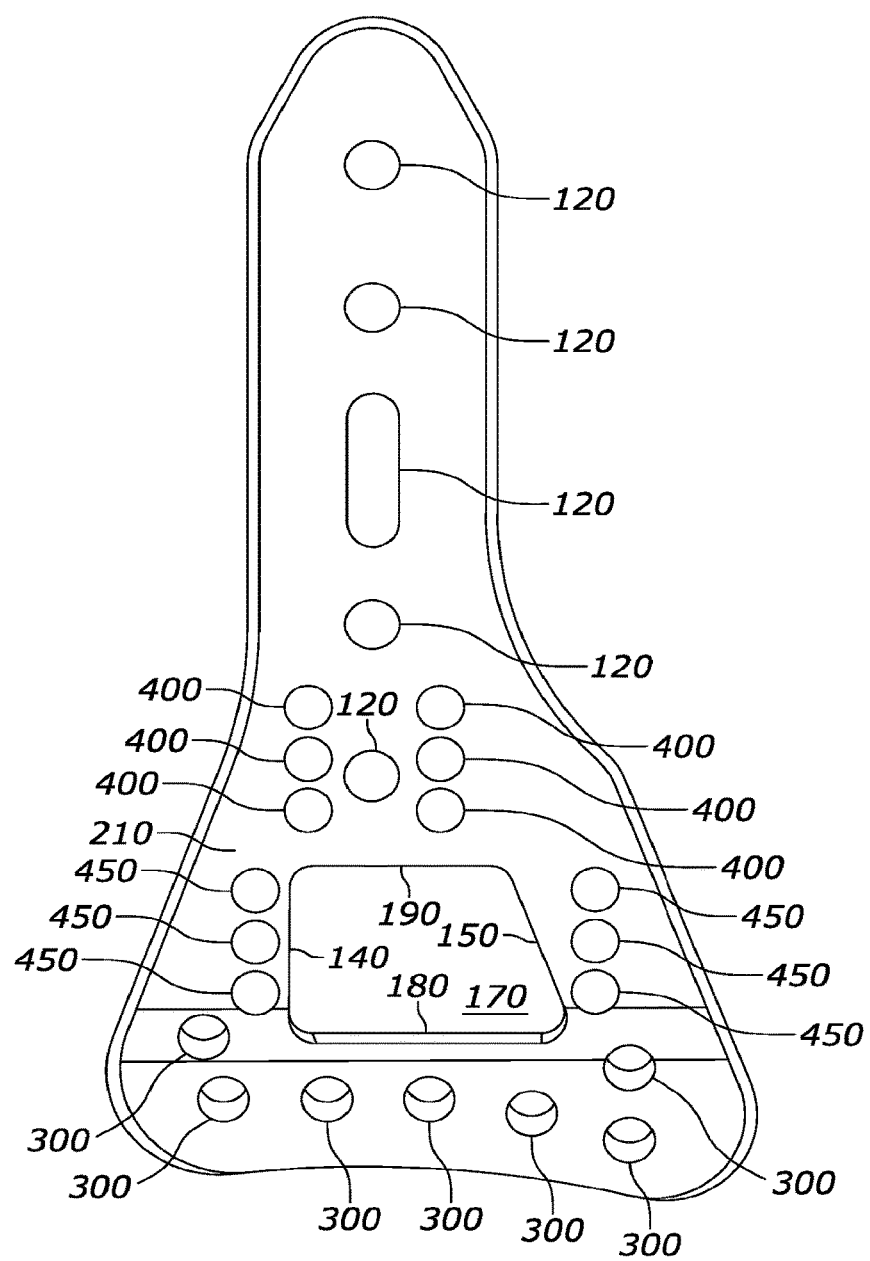
FIGS. 3 and 4 show the example RIVAR plate in dorsal and volar plan views, respectively.
Figure 4:
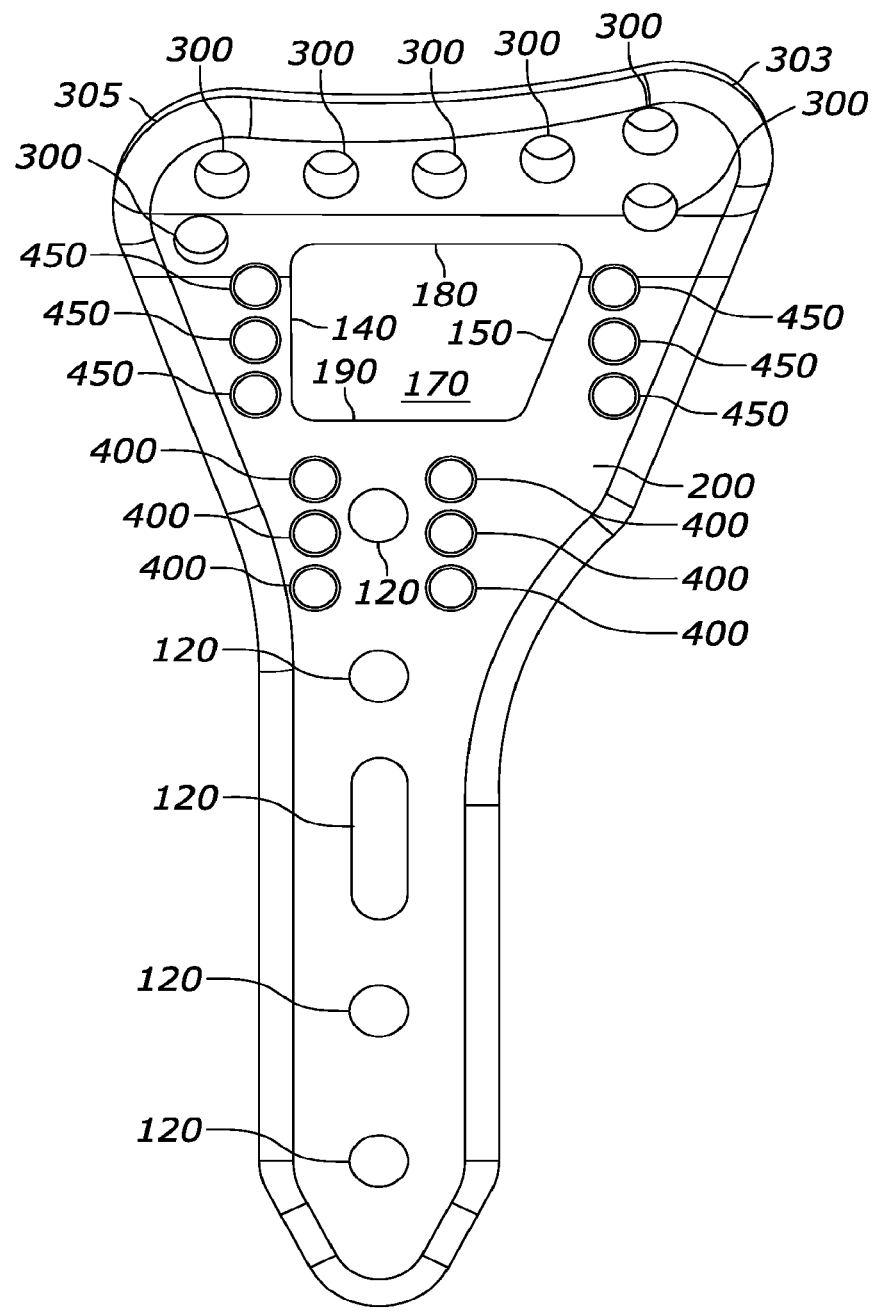

FIGS. 3 and 4 further illustrate the RIVAR plate 100. FIG. 3 is a dorsal plan view of the RIVAR plate 100. FIG. 4 is a volar plan view of the of the RIVAR plate 100. As may be appreciated from these figures, the holes 120 may extend all the way through the shank 110 in the dorsal-volar dimension 220, providing access to the holes from either face 200, 210. Holes 300 on the window portion 130 may similarly extend all the way through the window portion 130 in the dorsal-volar dimension 220. The holes 300 may also accept respective bone fasteners 125 (and/or K-wires). Accordingly, like the holes 120, if screws are used as fasteners 125, the holes 300 may be threaded to engage the threads of the screws. Also note that both the holes 120 and 300 may be locking or non-locking with respect to the fasteners 125, and the number of both the holes 120 and 300 may vary depending on implementation. The shapes of the holes 120 and 300 may also vary as well and, as such, it may be appreciated from FIGS. 3 and 4 that one of the holes 120 is oblong rather than circular like other holes 120.

Additionally, FIGS. 3 and 4 show that the holes 300 may specifically be disposed on the cross-member 160, and at least some of the holes 300 may be spaced from each other in the ulna-radius dimension 135. As also shown in these figures, the last hole 300 on each side of the cross-member 160 (according to the dimension 135) may also be spaced from an adjacent hole 300 in the proximal-distal dimension 115 as well. Other holes 300 besides the last one on each side may also be offset from each other in the dimension 115 as shown as well (while still being spaced from each other in the dimension 135) so that together they curve distally toward the radius side of the plate 100 as shown. Fasteners 125 may therefore be engaged with the holes 300 and 120 to mount the plate 100 to a patient's radius during radial fracture reduction.

Also note here that a radial-side distal tip 303 of the plate 100 may extend farther distally and radially than an ulnar-side distal tip 305 of the plate 100 extends ulnarly and distally to establish a generally radial inclination of the distal end portion of the plate 100, with the degree of offset between the two tips 303, 305 varying depending on implementation.

FIGS. 1, 3, and 4 also show proximal pad peg holes 400 and distal pad peg holes 450. Respective radial-side holes 400 may be coaxial with each other as shown, while respective ulnar-side holes 400 may also be coaxial with each other as shown, with holes 400 on either side being arranged along a longitudinal axis parallel to the longitudinal axis of the shank 110. Likewise, respective radial-side holes 450 may be coaxial with each other as shown, while respective ulnar-side holes 450 may also be coaxial with each other as shown, with holes 450 on either side being arranged along a longitudinal axis parallel to the longitudinal axis of the shank 110. Further note here that, as best shown in FIGS. 3 and 4, the holes 400 may be offset in the dimension 135 such that the radius-side holes 400 are spaced more from the radial edge of the plate 100 than the ulnar-side holes 400 are spaced from the ulnar edge of the plate 100, with respective transverse pairs of holes 400 from the ulnar and radius sides also being spaced equally from each other. Transverse pairs of the holes 450 may also be spaced equally from each other.

Additionally, the holes 400, 450 may not extend all the way through the shank 110 or window portion 130 in the dorsal-volar dimension 220 in some example embodiments, though in other embodiments they may in fact do so if desired. In any case, the holes 400, 450 may be respectively configured to closely receive, possibly in interference fit, respective pegs from respective proximal and distal pads. The distal pad may therefore be removably engageable with the window portion 130 by extending its pegs into the holes 450 in the window portion 130. The proximal pad may be removably engageable with the shank 110 by extending its own respective pegs into the holes 400 in the shank 110. It is to therefore be generally understood that each pad may include at least one peg, and optionally plural pegs, engageable with a respective hole 400 or 450. Also note that the number and location of the holes 400, 450 may vary depending on desired implementation.

Figure 5:
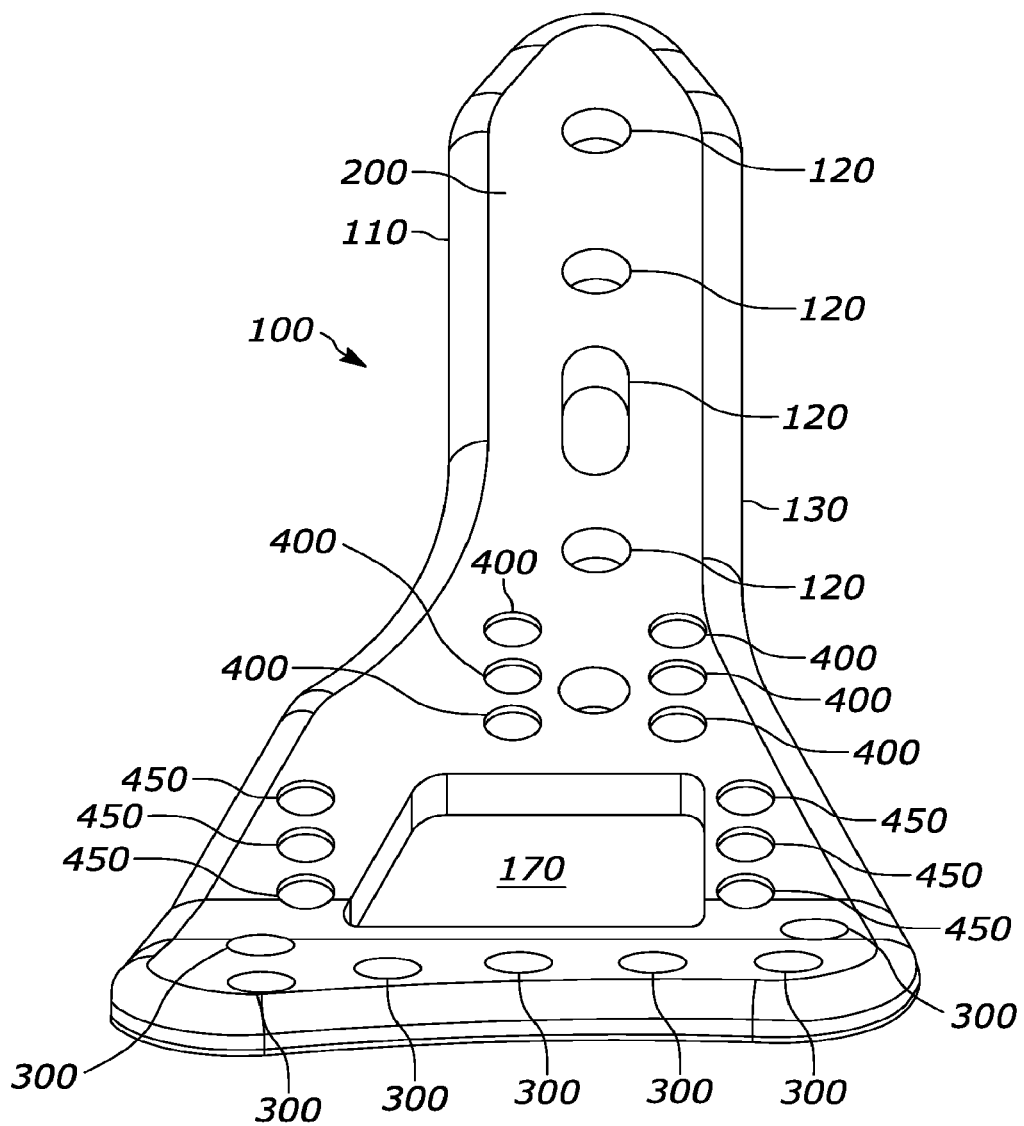
FIG. 5 shows a perspective view looking at the example RIVAR plate from distal to proximal.
Figure 6:
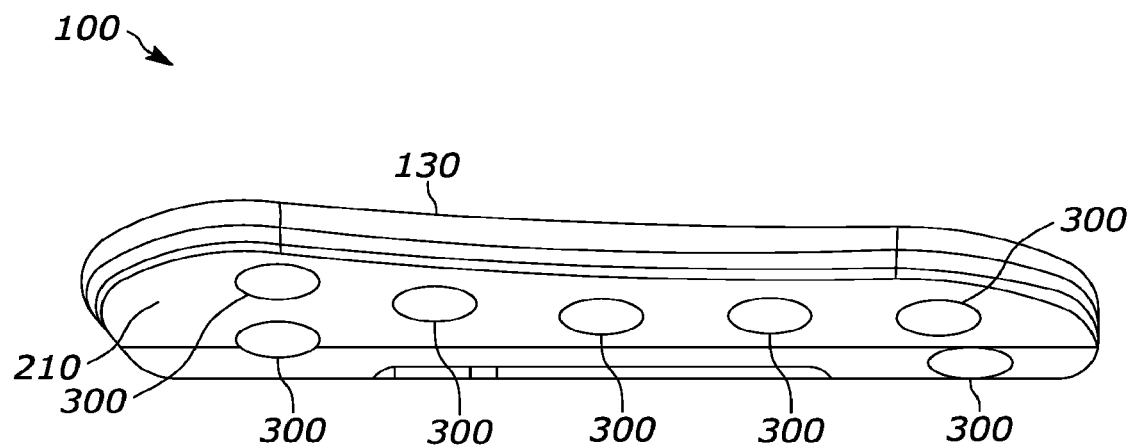
FIG. 6 shows a distal end elevational view of the example RIVAR plate.
Figure 7:
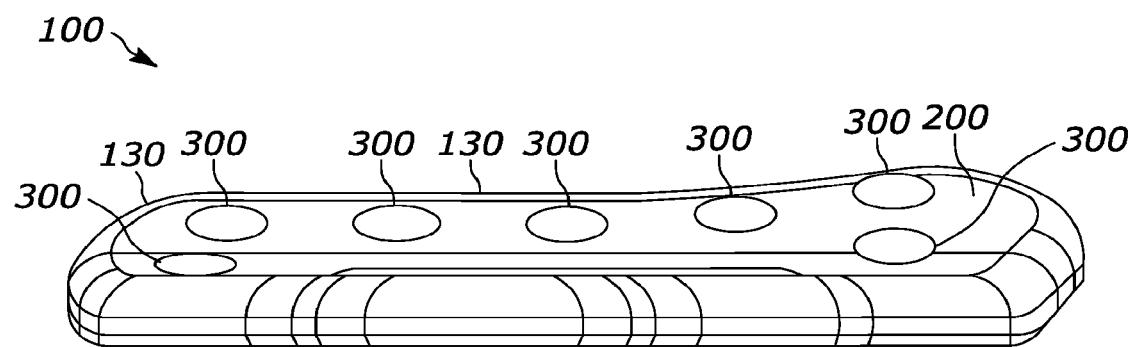
FIG. 7 shows a proximal end elevational view of the example RIVAR plate.

FIGS. 5-7 show additional views of the plate 100 consistent with present principles. Specifically, FIG. 5 shows a perspective view looking at the plate from distal to proximal. FIG. 6 shows a front/distal end elevational view of the plate 100 to appreciate the distal curve of the window portion 130. FIG. 7 shows a rear/proximal end elevational view to further appreciate this curve from another angle.

Figure 8:
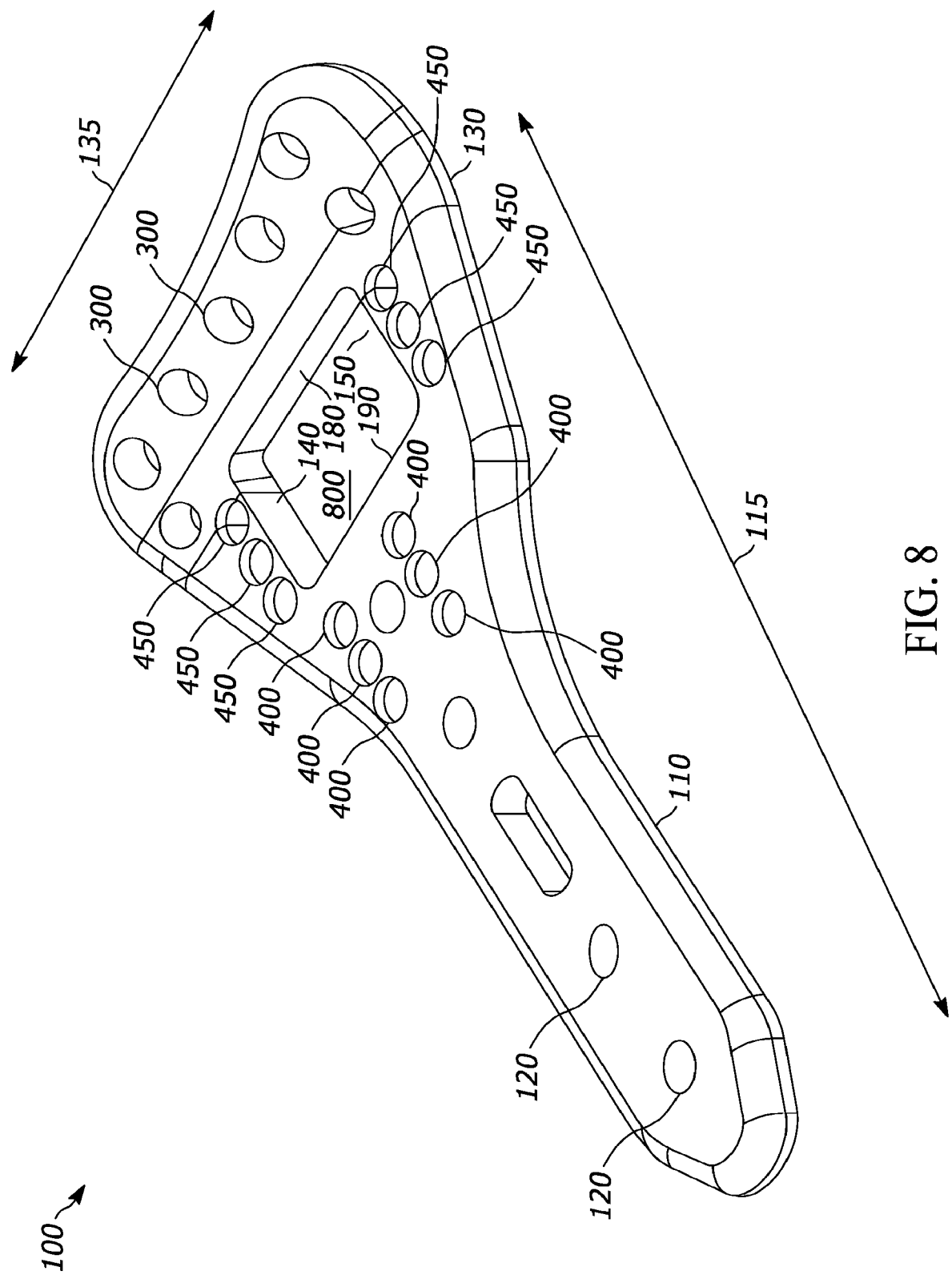
FIGS. 8-10 show respective perspective, volar plan, and dorsal plan views of another example RIVAR plate with equilateral radial and ulnar window walls consistent with present principles.
Figure 9:
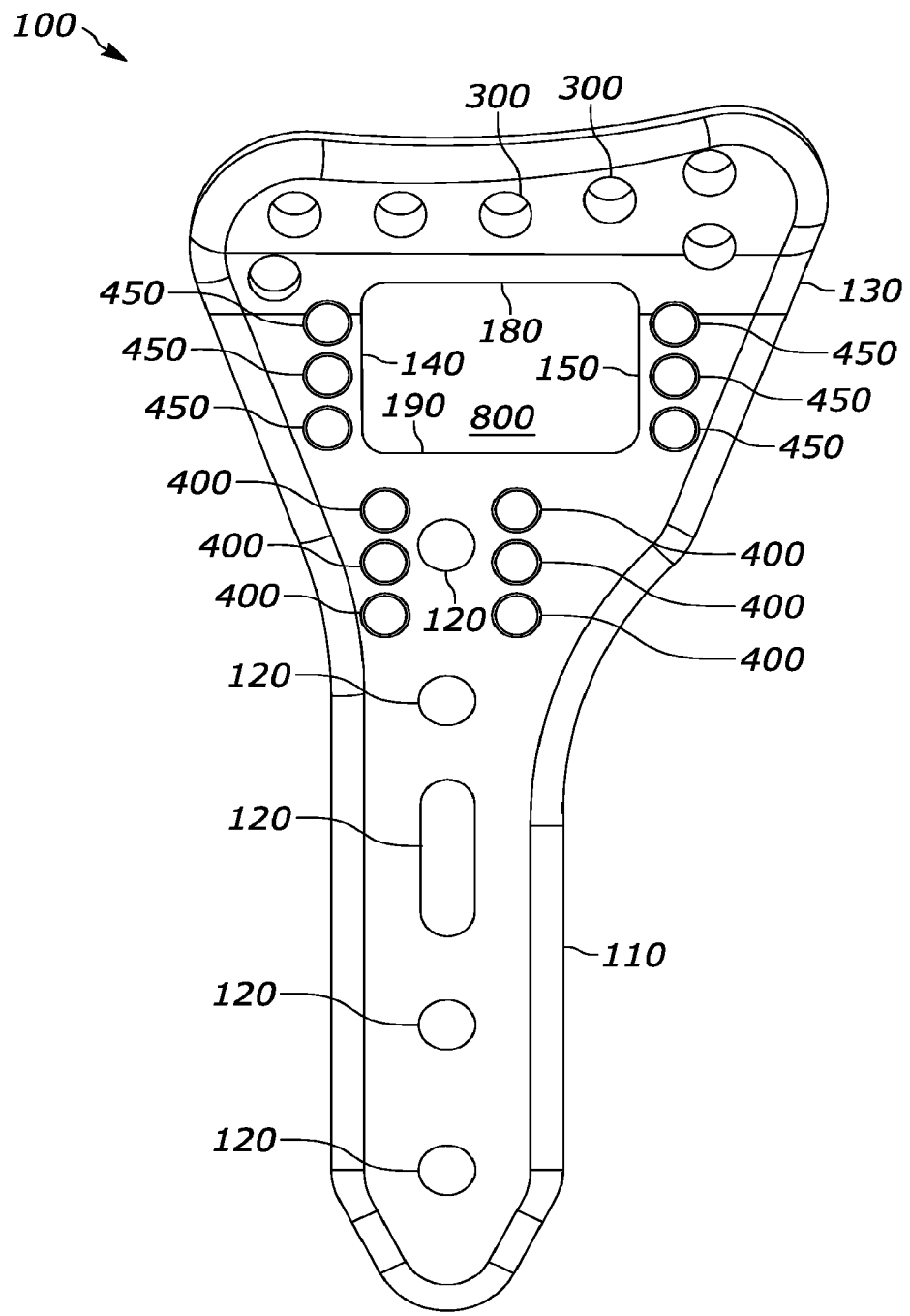
Figure 10:
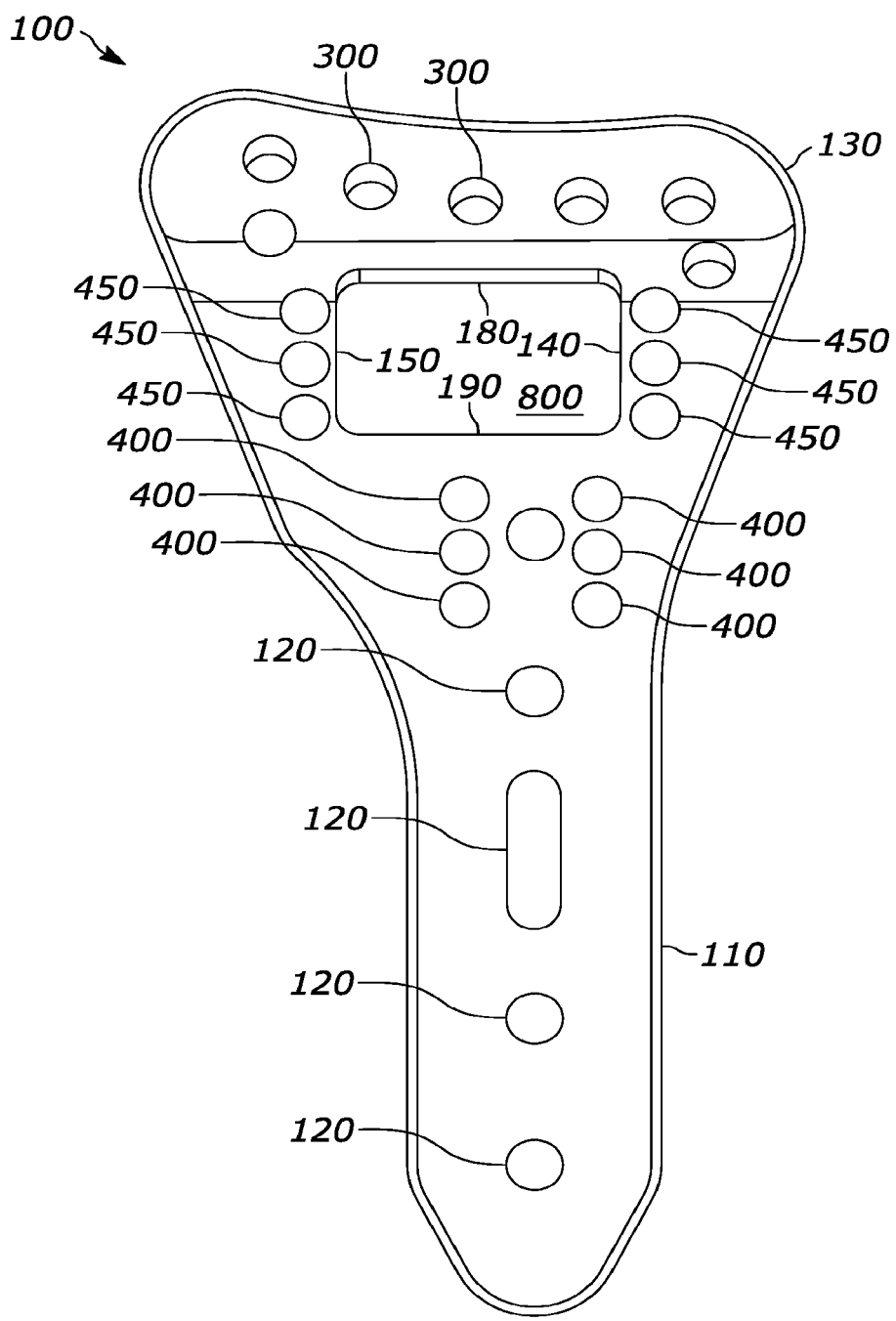

Turning to FIGS. 8-10, these figures show an alternate example embodiment of a window in the window portion 130 of the plate 100. Here, all other aspects described above may be the same but for the configuration of the window. FIG. 8 shows a perspective view of the plate 100, FIG. 9 shows a volar/bottom plan view of the plate 100, and FIG. 10 shows a dorsal/top plan view of the plate 100. Distinguishing this example embodiment, note that in each of these figures, the walls 140 and 150 are equilateral (rather than the wall 150 tapering radially per the embodiment of FIGS. 1-7). Also note that the walls 180, 190 are equilateral, forming a rectangular-shaped window 800 in the portion 130. Thus, according to this example embodiment, both the ulnar wall 140 and radial wall 150 may extend from proximal to distal along axes that are parallel to the longitudinal axis of the plate 100 as defined the proximal-distal dimension 115 (rather than the radial wall 150 extending obliquely and radially toward a radial side of the plate 100 according to the ulna-radius dimension 135 per the first embodiment of FIGS. 1-7). Also according to this example, the proximal wall 190 and distal wall 180 may extend along axes that are parallel to the transverse axis of the plate 100 as defined by the ulna-radius dimension 135. What's more, note that as best shown in FIGS. 9 and 10, the holes 400 may still be offset in the dimension 135 as described above such that the radius-side holes 400 are spaced more from the radial edge of the plate 100 than the ulnar-side holes 400 are spaced from the ulnar edge of the plate, with respective transverse pairs of holes 400 from the ulnar and radius sides still being spaced equally from each other.

The equilateral window embodiment of FIGS. 8-10 might be used, for example, by placing an osteotome through the window, across the fracture, and levering the handle toward the forearm, away from the hand, effecting an increase in length and dorsal angulation of the distal radius. Alternatively, after placing the osteotome across the fracture, a distal pad may be placed on the plate, thus holding the osteotome against the inner proximal edge of the reduction window during the process of levering. Alternatively, if greater length restoration is desired, pads may be applied to the volar surface of the RIVAR plate as described below.

Now in reference to FIG. 11A through FIG. 15C, proximal pads will now be described that may be engaged with the plate 100 via the holes 400 in the shank 110 consistent with present principles. Amongst these figures, the "A" figures show a proximal pad 1100 of a first thickness in the dorsal-volar dimension, the "B" figures show a proximal pad 1125 of a second (greater) thickness in the dorsal-volar dimension, and the "C" figures show a proximal pad 1150 of a third (even greater) thickness in the dorsal-volar dimension. These pads may be of the following respective thicknesses in certain example embodiments: 0.5 cm, 1.0 cm and 2.0 cm, with the thicker two pads affecting progressively greater lengthening of the compressed and shortened distal radius fragment by moving the fulcrum further from the surface of the bone. The exact amount of lengthening is affected by: the thickness of the proximal and distal pads, the quality or compressibility of the bone, and the excursion angle of the osteotome blade. The Reduction Chart described below may serve as an example guide for the degree of expected lengthening so that the correct distal and proximal pad(s) may be selected. Lengthening may be done under direct fluoroscopic guidance. Once acceptable alignment is achieved, the osteotome may be held in place by the curved extensions on the volar surface of the pads, thus allowing the surgeon to have both hands free to apply fixation screws to the distal fragment(s).

Figure 11A:
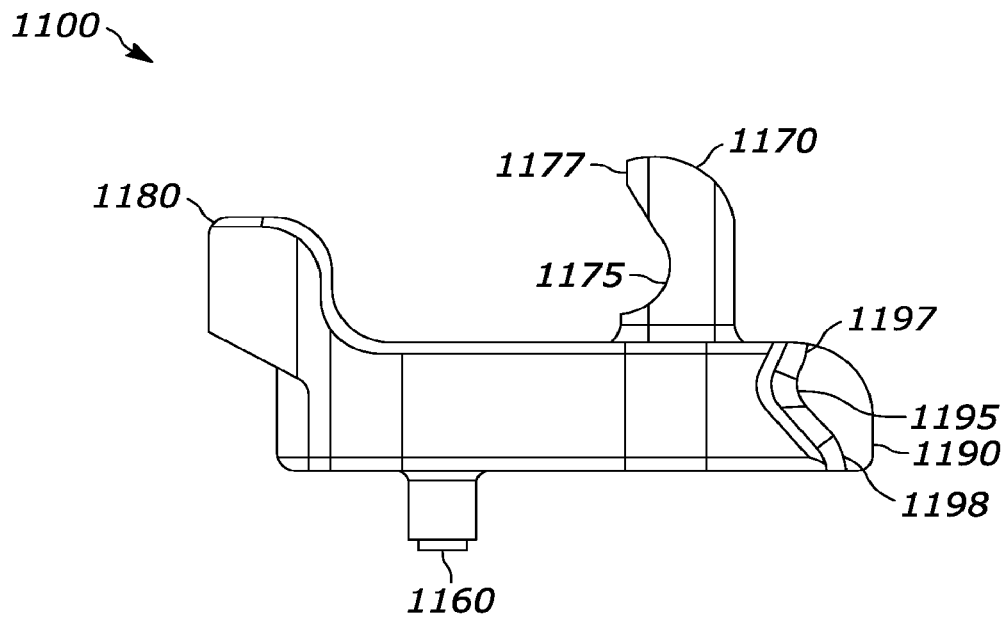
FIGS. 11A-11C show side elevational views of example proximal pads of varying thickness that may be engaged with a RIVAR plate consistent with present principles.
Figure 11B:
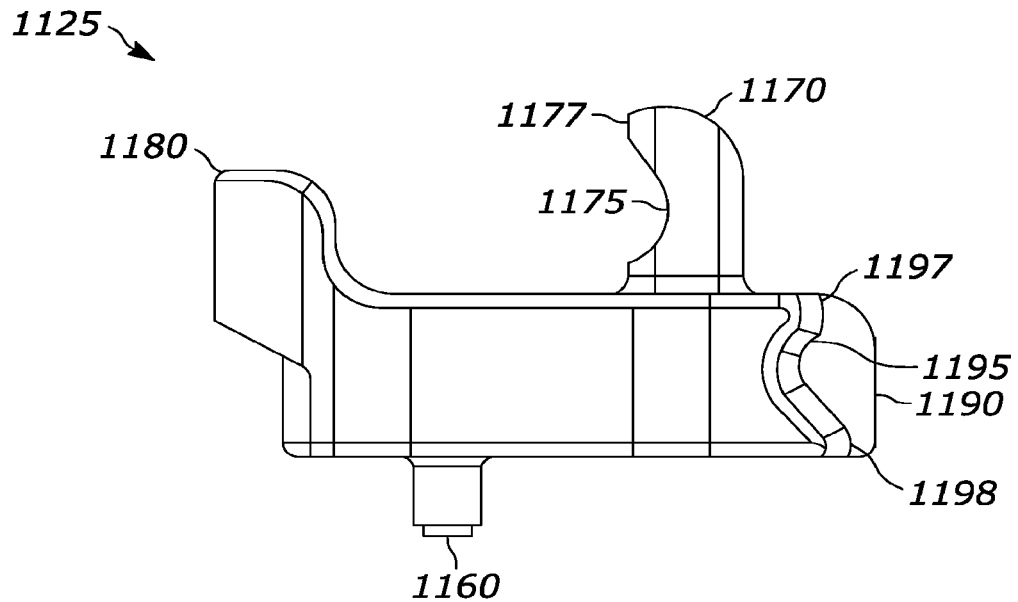
Figure 11C:
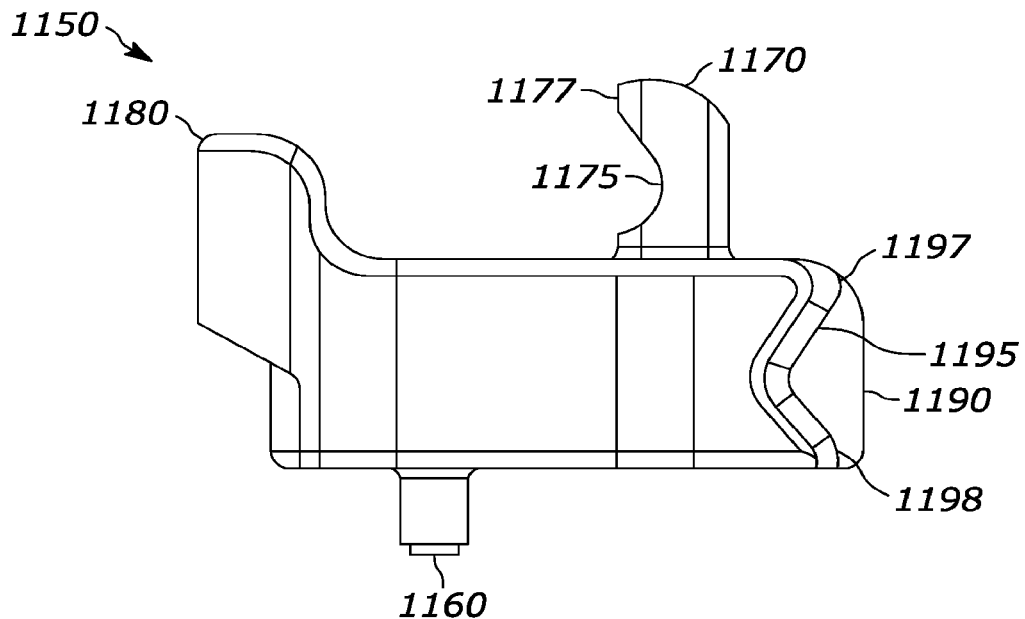
Figure 12A:
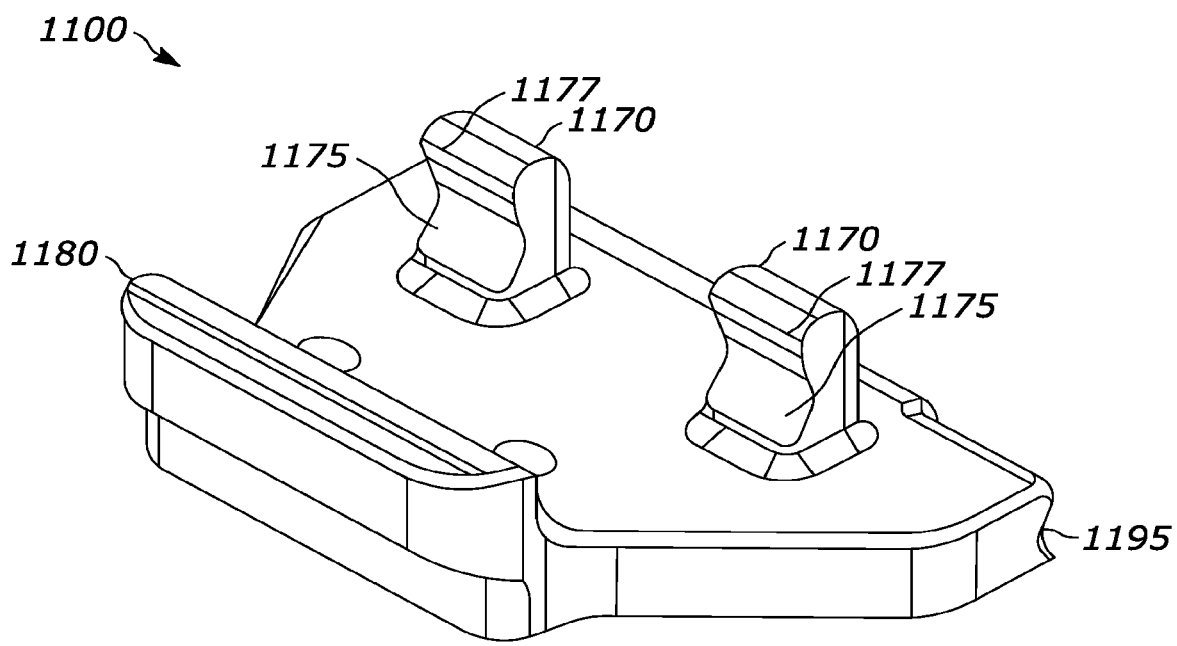
FIGS. 12A-12C show perspective views of the proximal pads from a generally proximal viewpoint.
Figure 12B:
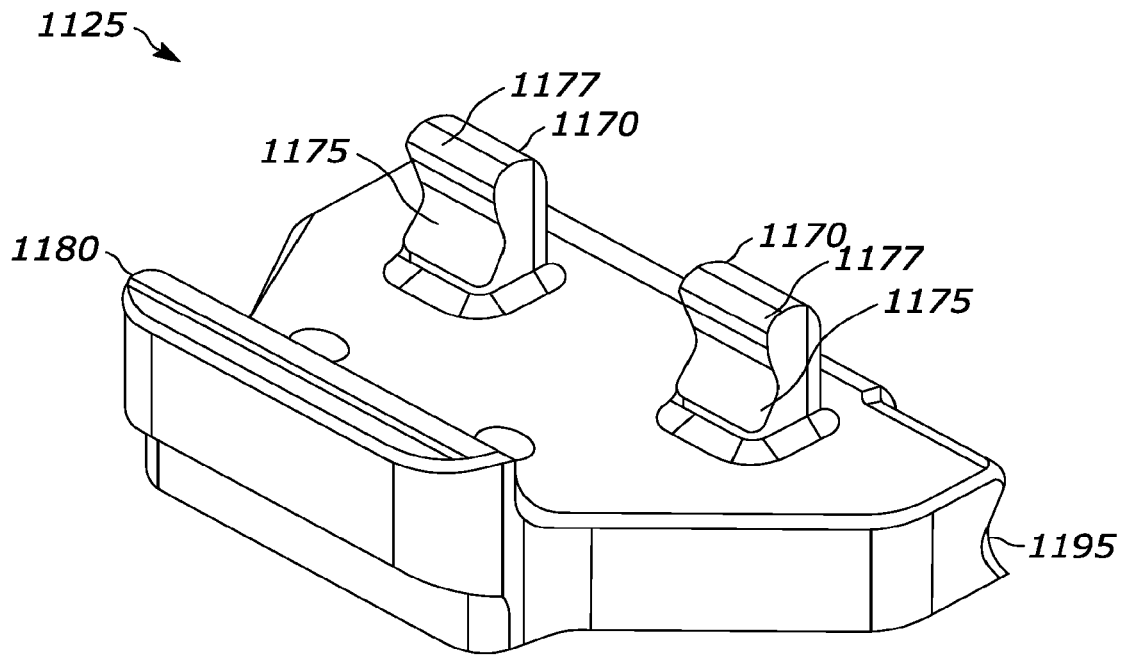
Figure 12C:
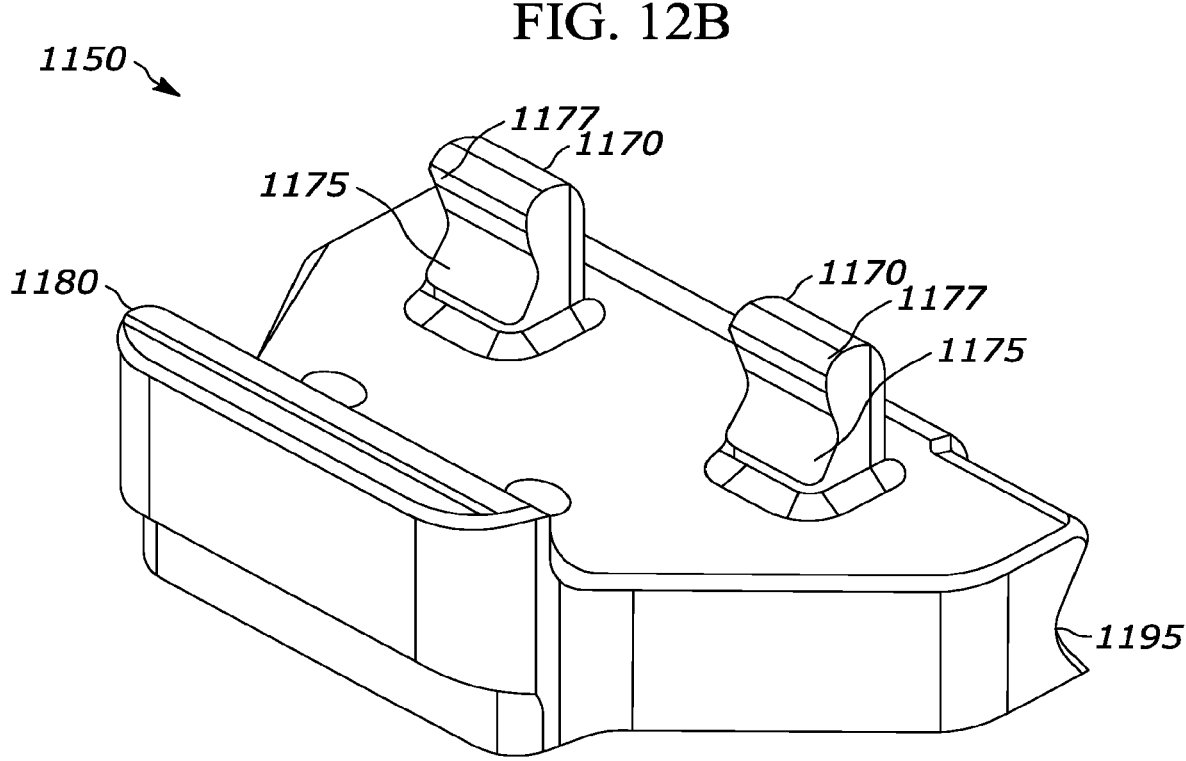
Figure 13A:
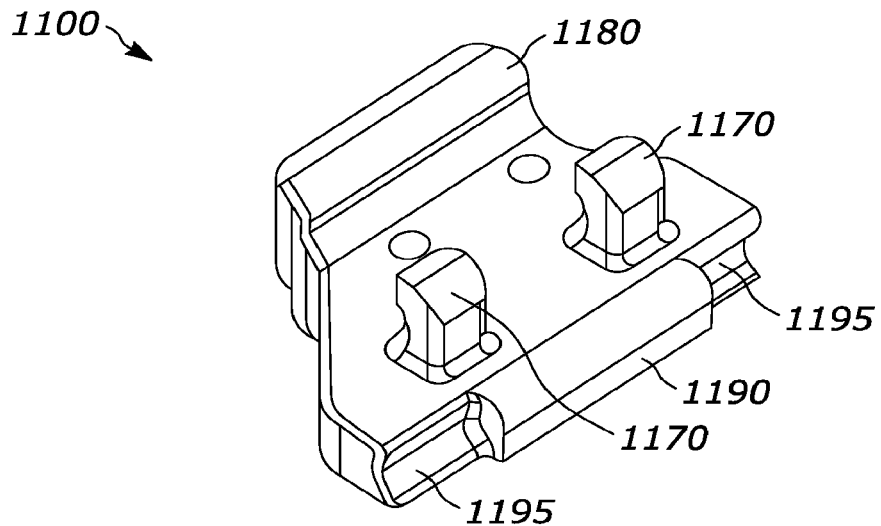
FIGS. 13A-13C show perspective views of the proximal pads from a generally distal viewpoint.
Figure 13B:
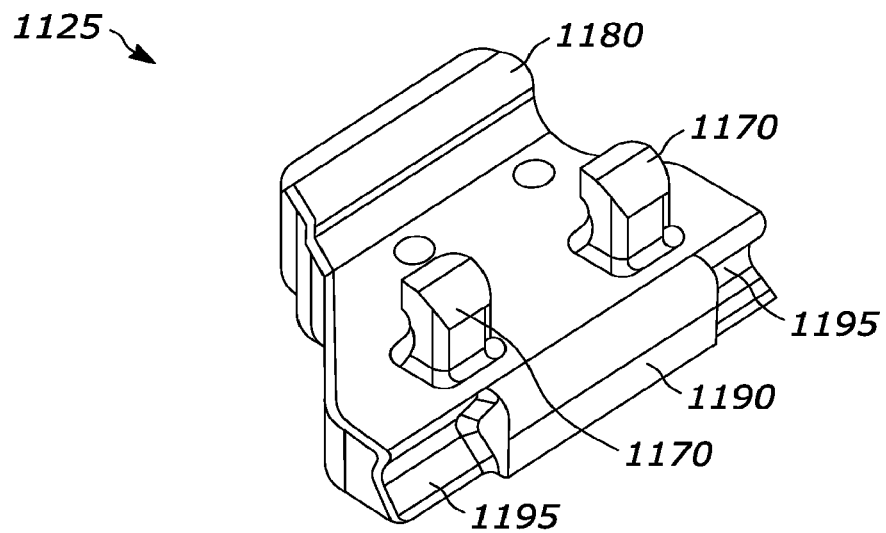
Figure 13C:
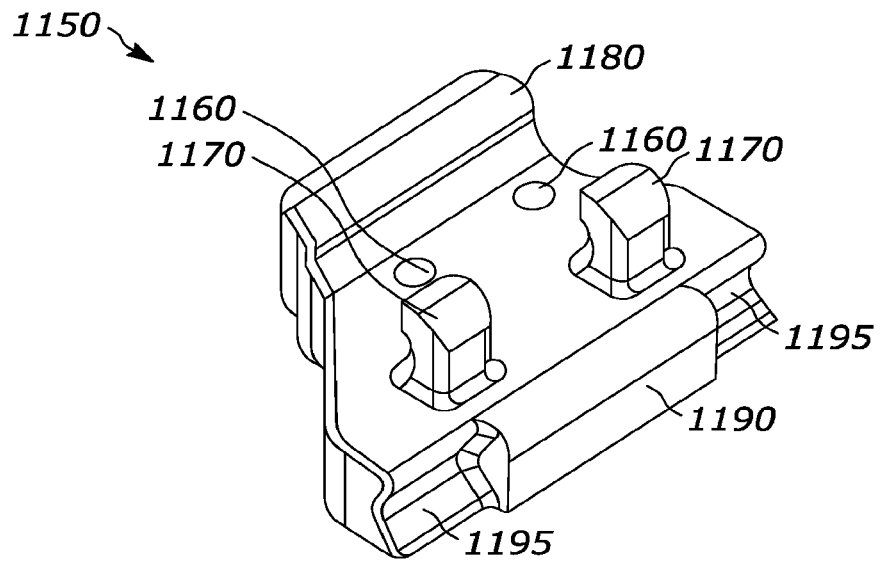
Figure 14A:
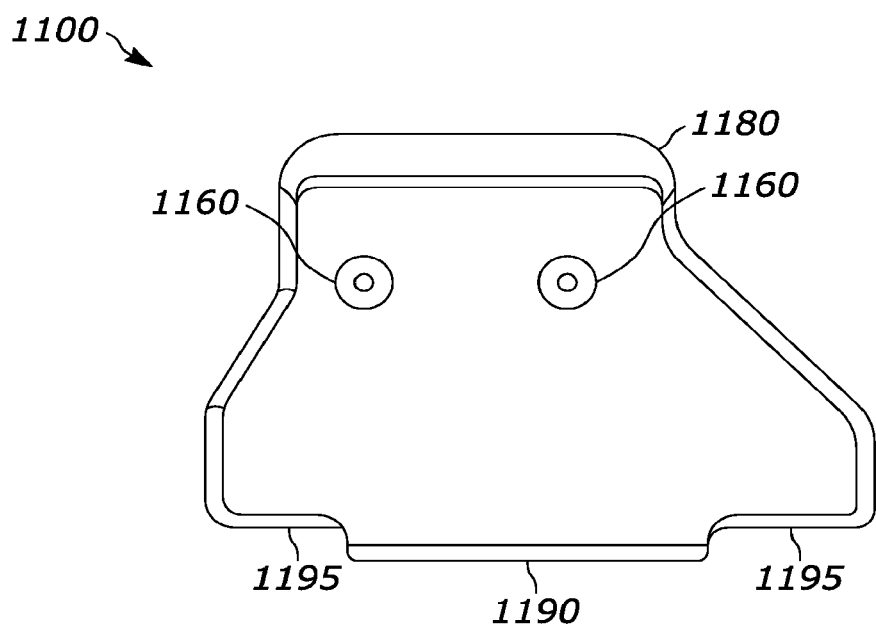
FIGS. 14A-14C show plan views of a dorsal face of the proximal pads.
Figure 14B:
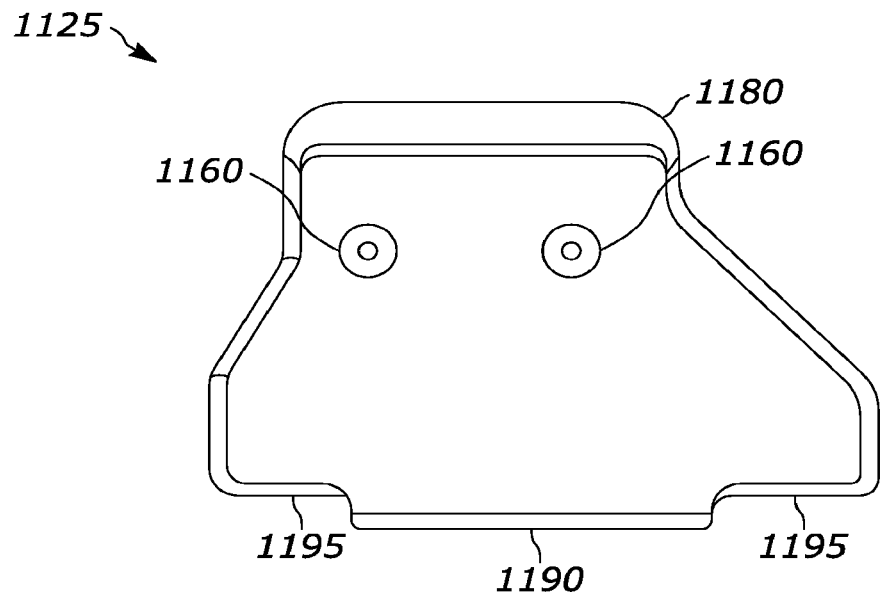
Figure 14C:
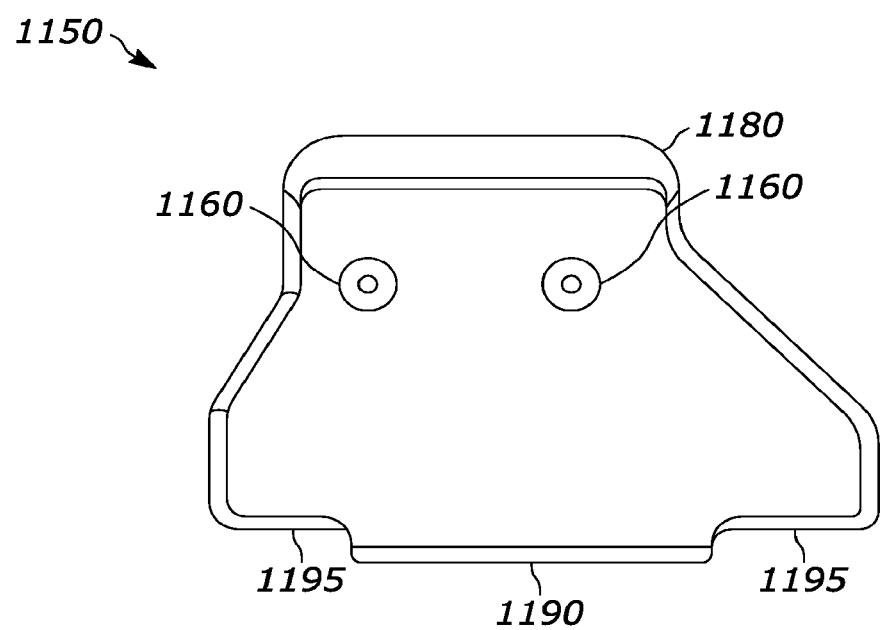
Figure 15A:
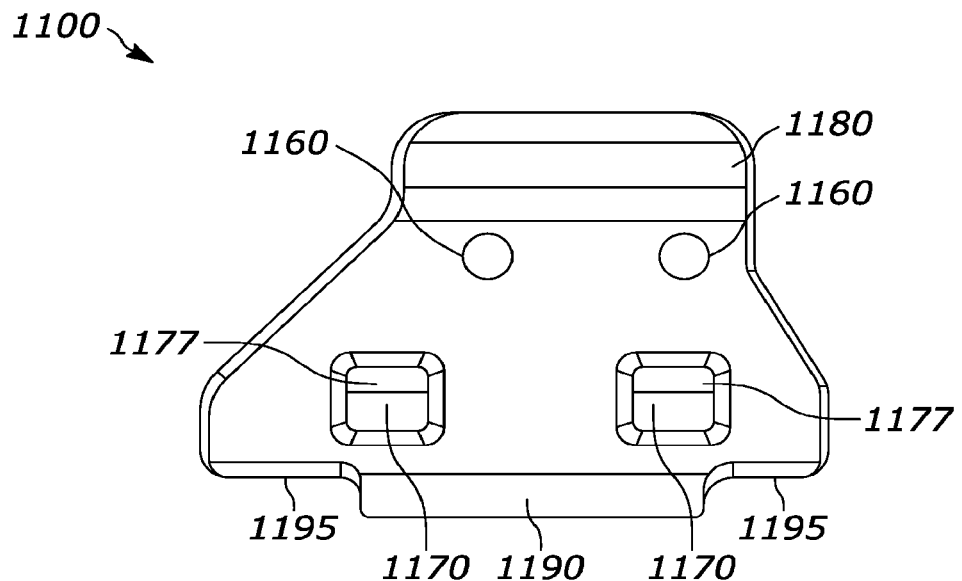
FIGS. 15A-15C show plan views of a volar face of the proximal pads.
Figure 15B:
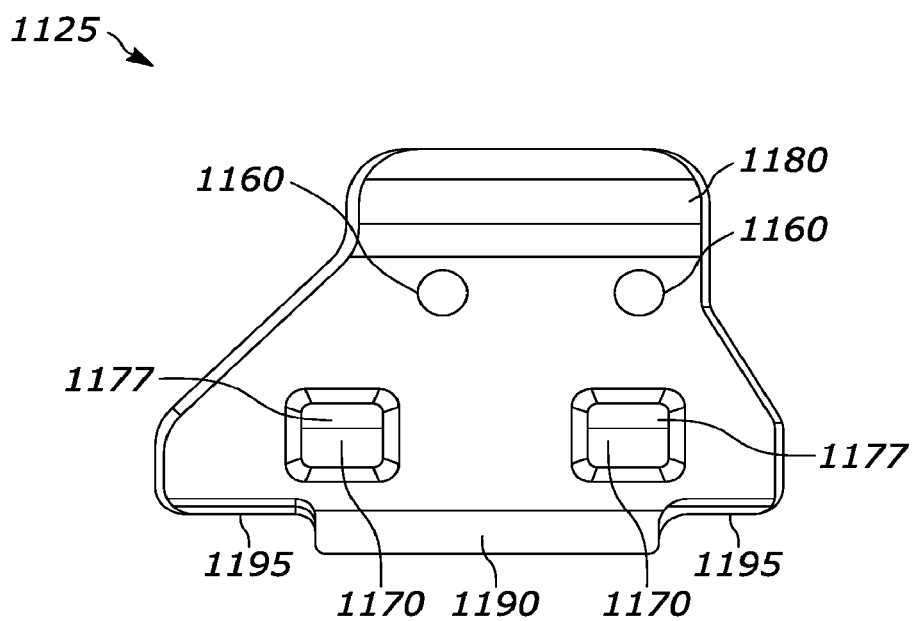
Figure 15C:
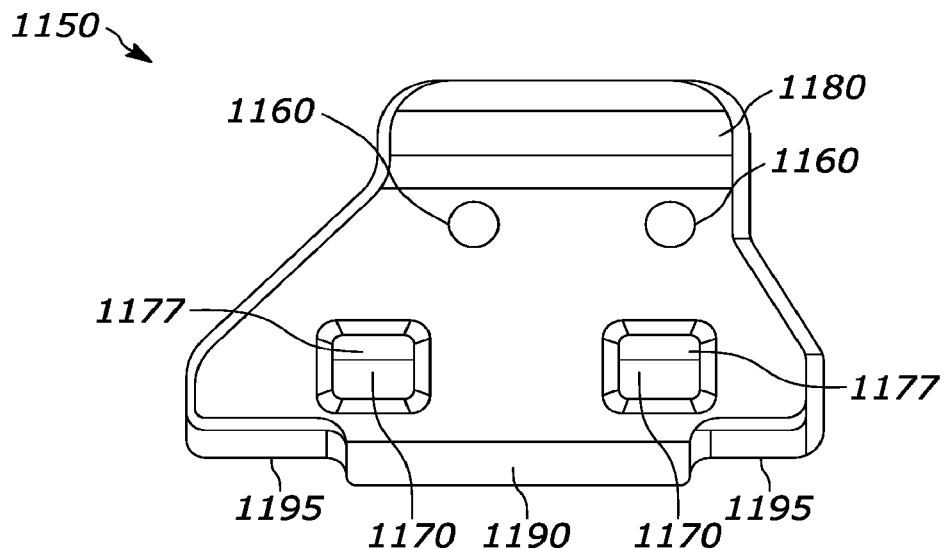

Also note that FIGS. 11A-11C show side elevational views of proximal pads, FIGS. 12A-12C show perspective views of the pads from a generally proximal viewpoint, FIGS. 13A-13C show perspective views of the pads from a generally distal viewpoint, FIGS. 14A-14C show plan views of a dorsal face of the pads, and FIGS. 15A-15C show plan views of a volar face of the pads.

Save for differences in the thickness of the pads 1100, 1125, 1150, like components may be included on each of the pads 1100, 1125, and 1150, with those components being configured the same on each respective pad. Accordingly, reference will be made mostly to the pad 1100, with like components being similarly configured and arranged on the pads 1125, 1150 as well.

As shown in FIG. 11A, the pad 1100 may include at least one, and preferably but optionally plural, pegs 1160 each engageable with a respective hole 400 in the shank 110. Each peg 1160 may extend away from a dorsal face of the proximal pad 1100, with the dorsal face of the pad abutting and lying flat against the face 200 when the peg(s) 1160 are fully positioned into respective holes 400. Thus, note that the dorsal face of the pad 1100 may sit flat against the face 200 when the pad 1100 itself is fully engaged with the plate 100.

The pegs 1160 themselves may be cylindrical and integral with the pad 1100. Both the pegs 1160 and pad 1100 may be rigid. The pegs 1160 and pad 1100 may be made of titanium, titanium alloy, stainless steel, cobalt chrome, iron, cobalt, chromium, other metal alloys, tantalum, polyethylene, acrylic, other polymers/plastics, and/or ceramics etc. Additionally, as shown in FIGS. 11A-11C, the pegs 1160 may include a cylindrical end on the dorsal end portion of the respective peg 1160, with the cylindrical end having a diameter less than the diameter of a volar cylindrical segment of the respective peg 1160 that extends dorsally away from the dorsal face of the pad 1100 toward the cylindrical end.

FIG. 11A and others also show that the pad 1100 may include at least one, and preferably but optionally plural, extension elements 1170 extending from a volar side of the pad 1100. The elements 1170 may establish hooks or otherwise include a curved end portion, with each hook/curved end portion configured for receiving a portion of one or more bars extending laterally from an osteotome as will be described in greater detail later.

Accordingly, each element 1170 may include a groove 1175 into which the lateral bar of the osteotome may be placed. The grooves 1175 may be in a proximal face of the element 1170 to engage the osteotome bar. Each element 1170 may also include a lip 1177 at each volar end segment of the element 1170. Each lip 1177 may also form part of the hook, and as such may extend proximally and away from the element 1170, helping to form the hook along with the groove 1175 itself to hold the osteotome securely and steadily in the in the hook under control of a physician. Further note that, if desired, a dorsal end segment of the element 1170 that meets the volar face of the pad 1100 may also extend proximally and away from the longitudinal axis of the element 1170 near the body of the pad 1100 (at a base of the element 1170), also helping to form the hook with the smooth and concave groove 1175 and lip 1177.

As also variously shown in these figures, the proximal pad 1100 may also include another extension element 1180 on a proximal end segment of the pad 1100, with the element 1180 extending volarly away from the volar surface of the pad 1100 and also possibly extending proximally away from a proximal body segment of the pad 1100. The element 1180 may be curved convex with an apex facing in a distal-volar direction as shown. The extension element 1180 may help guide a transverse bar of the osteotome into the hooks of the elements 1170, and may also be used for gripping by the surgeon when engaging the pad 1100 with the plate 100 itself.

The proximal pad 1100 may also include a distal edge 1190 against which the osteotome may be positioned. The edge 1190 may act as a fulcrum for the osteotome during osteotome levering for distal radius fracture reduction. As shown best in FIGS. 13A-13C, the distal edge 1190 may extend transversely along middle portions of the distal side of the respective pad 1100, with side end segments of the distal side receding proximally to establish hollow grooves 1195 that extend transversely toward the respective radial and ulnar sides of the pad 1100. The grooves 1195 may be smooth, generally concave, and face distally. The grooves 1195 may also be bounded by volar and dorsal lips 1197, 1198 as shown best in FIGS. 11A-11C. The grooves 1195 may thus be configured to closely receive part of a distal pad as will be described in more detail below.

But referring back to the distal edge 1190, note that it may include a face that is generally perpendicular to the volar face of the pad 1100 (and therefore perpendicular to the volar face 200 of the plate 100 when the pad 1100 is engaged with the plate 100). Additionally, the volar end segment of the distal edge 1190 may be curved convexly and extend between the perpendicular face of the edge 1190 and the volar surface of the pad 1100 itself.

Now in reference to FIG. 16A through FIG. 20C, a first example embodiment of distal pads will now be described that may be engaged with the plate 100 via the holes 450 consistent with present principles. This first example embodiment may be used for instances where an increase in radial inclination is not being performed as part of a distal radius fracture reduction. Amongst these figures, the "A" figures show a distal pad 1600 of a first thickness in the dorsal-volar dimension, the "B" figures show a distal pad 1625 of a second (greater) thickness in the dorsal-volar dimension, and the "C" figures show a distal pad 1650 of a third (even greater) thickness in the dorsal-volar dimension. Thus, again note that the pads 1600, 1625, and 1650 may be of the following respective thicknesses: 0.5 cm, 1.0 cm, and 2.0 cm).

Figure 16A:
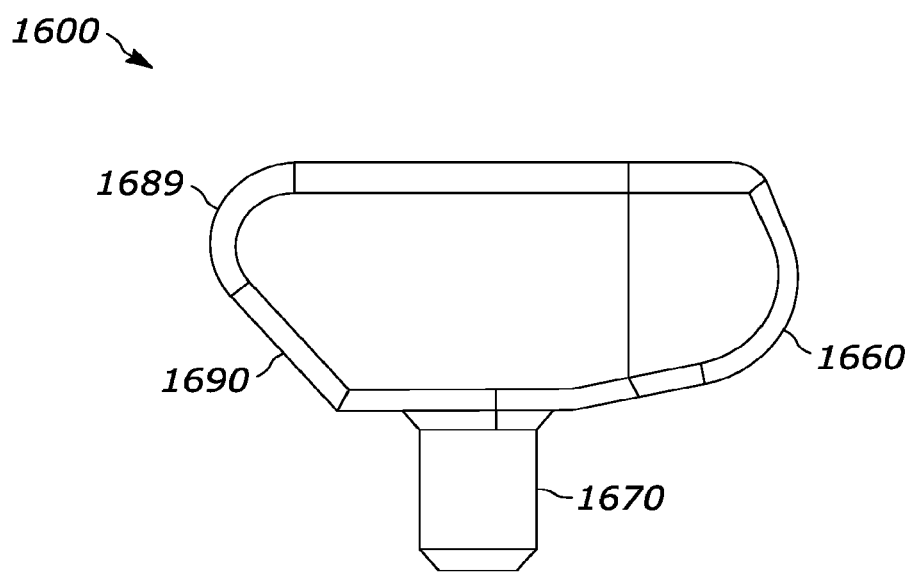
FIGS. 16A-16C show side elevational views of example distal pads of varying thickness that may be engaged with a RIVAR plate consistent with present principles.
Figure 16B:
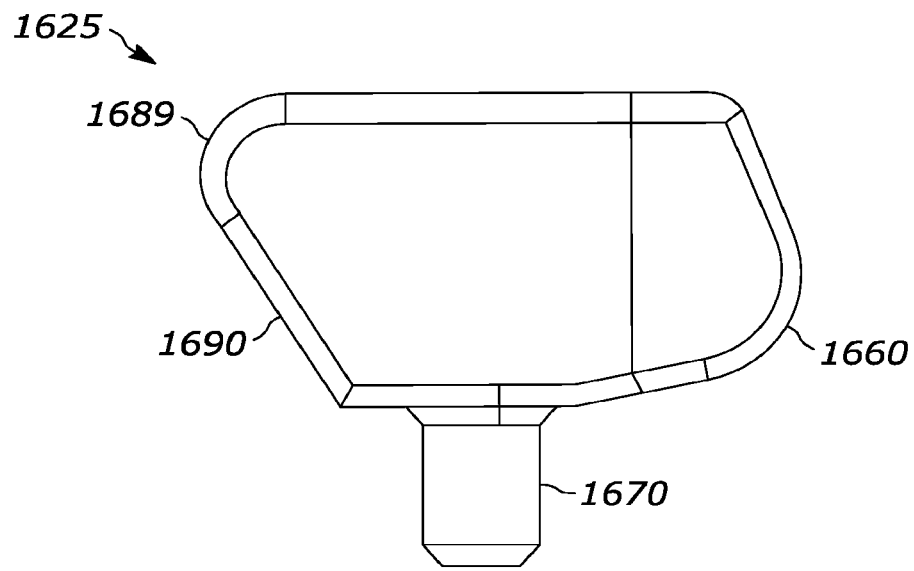
Figure 16C:
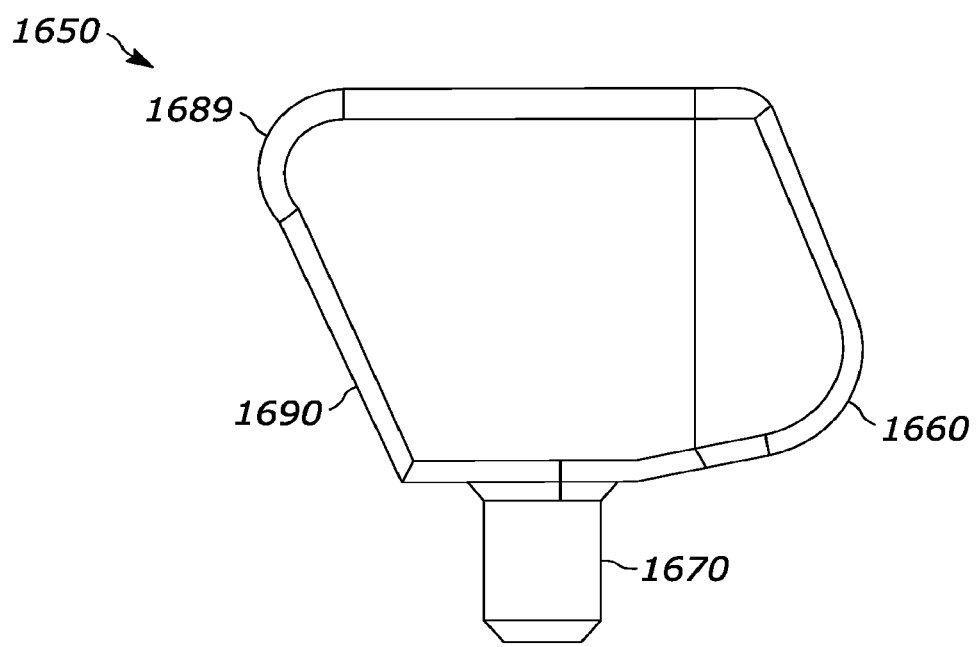
Figure 17A:
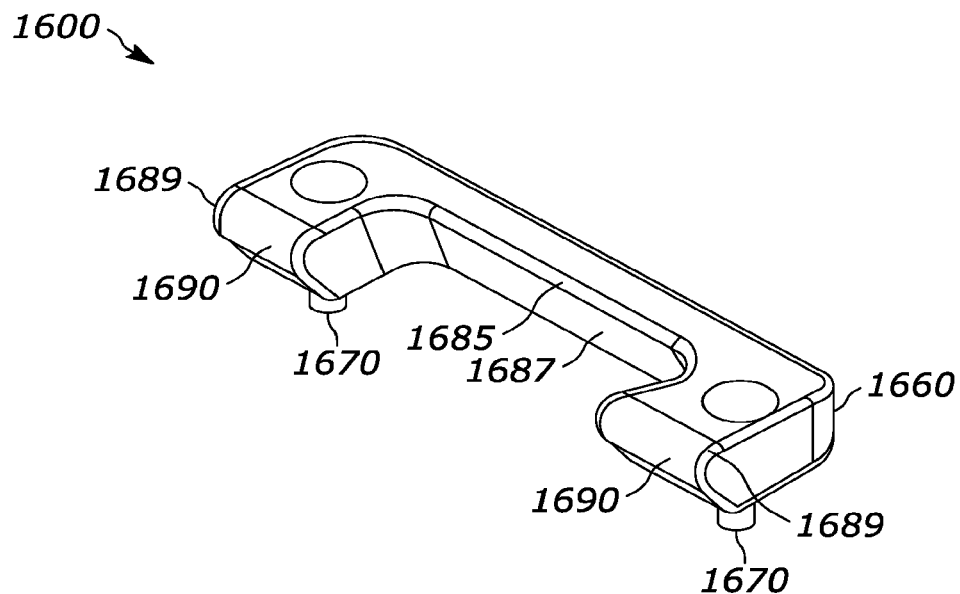
FIGS. 17A-17C show perspective views of the distal pads from a generally proximal viewpoint.
Figure 17B:
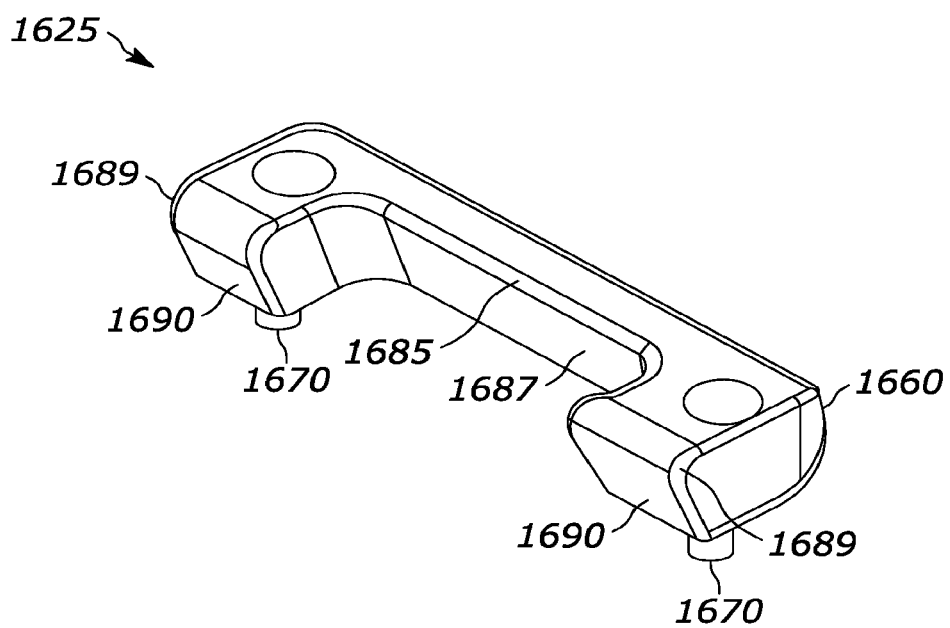
Figure 17C:
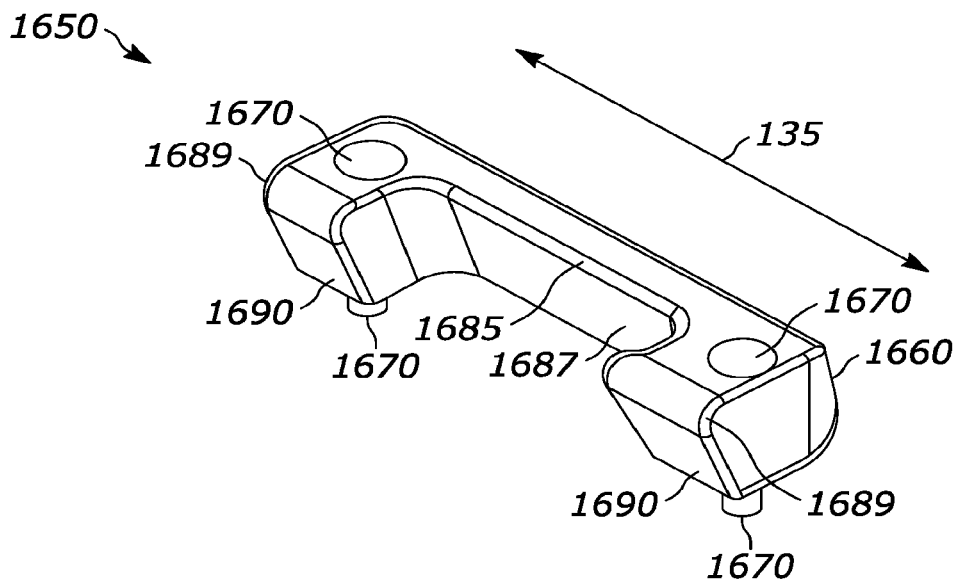
Figure 18A:
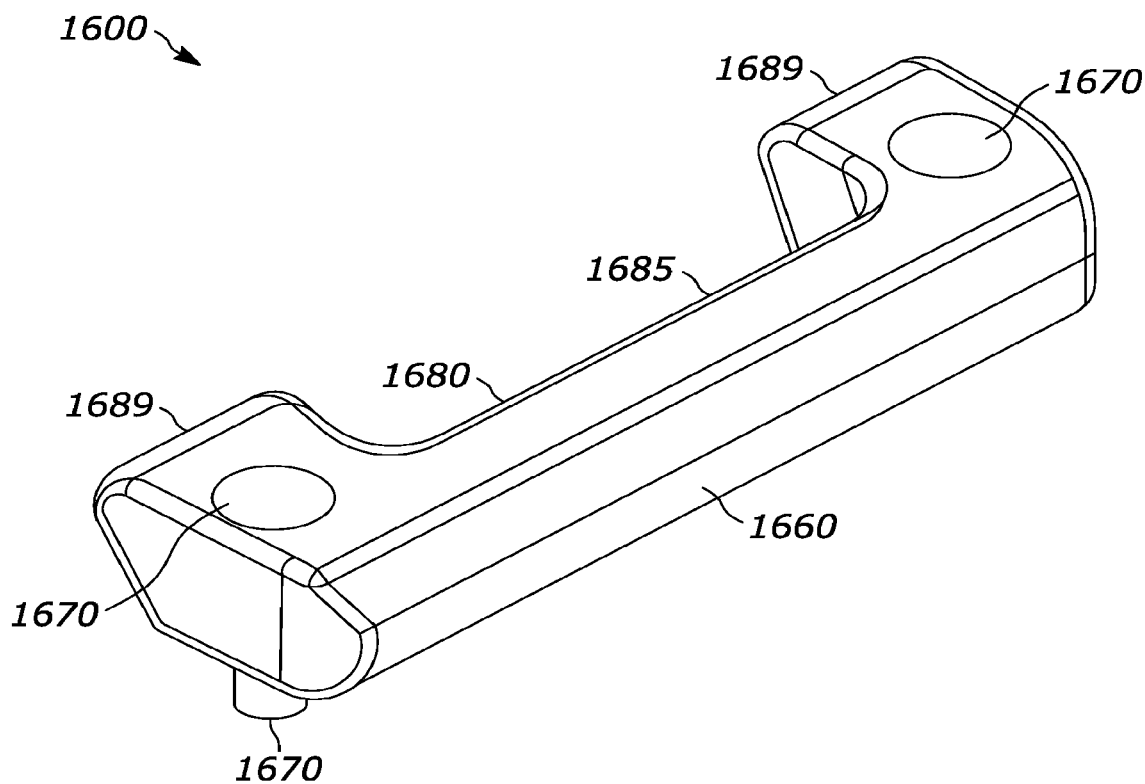
FIGS. 18A-18C show perspective views of the distal pads from a generally distal viewpoint.
Figure 18B:
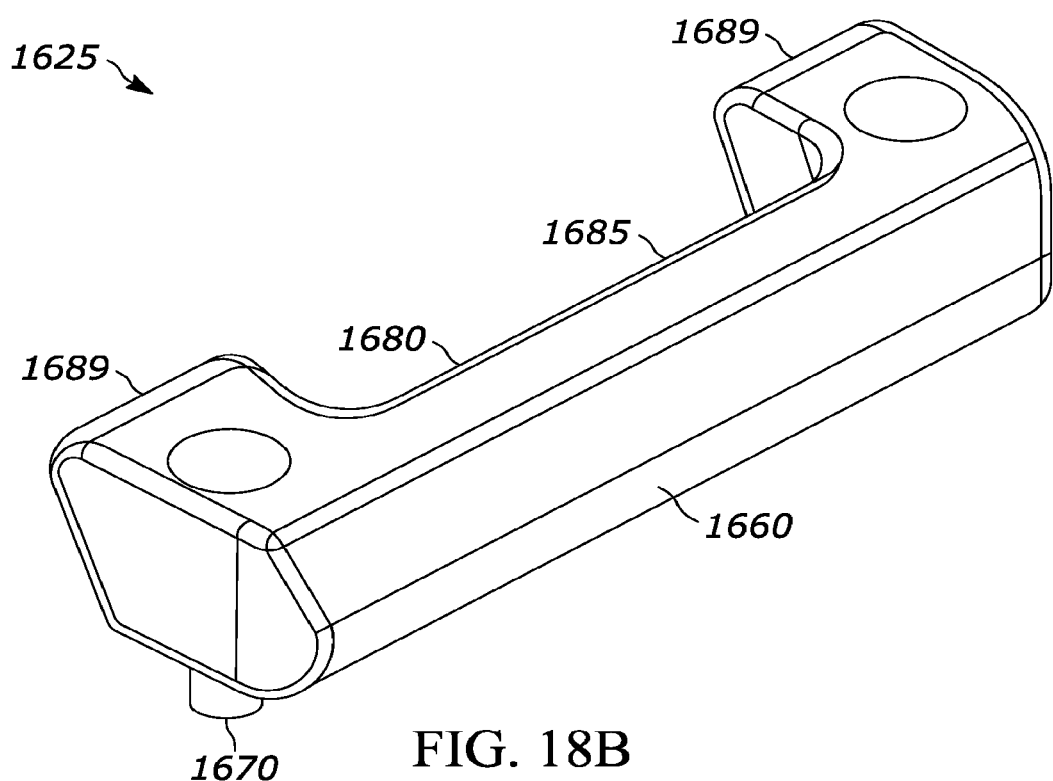
Figure 18C:
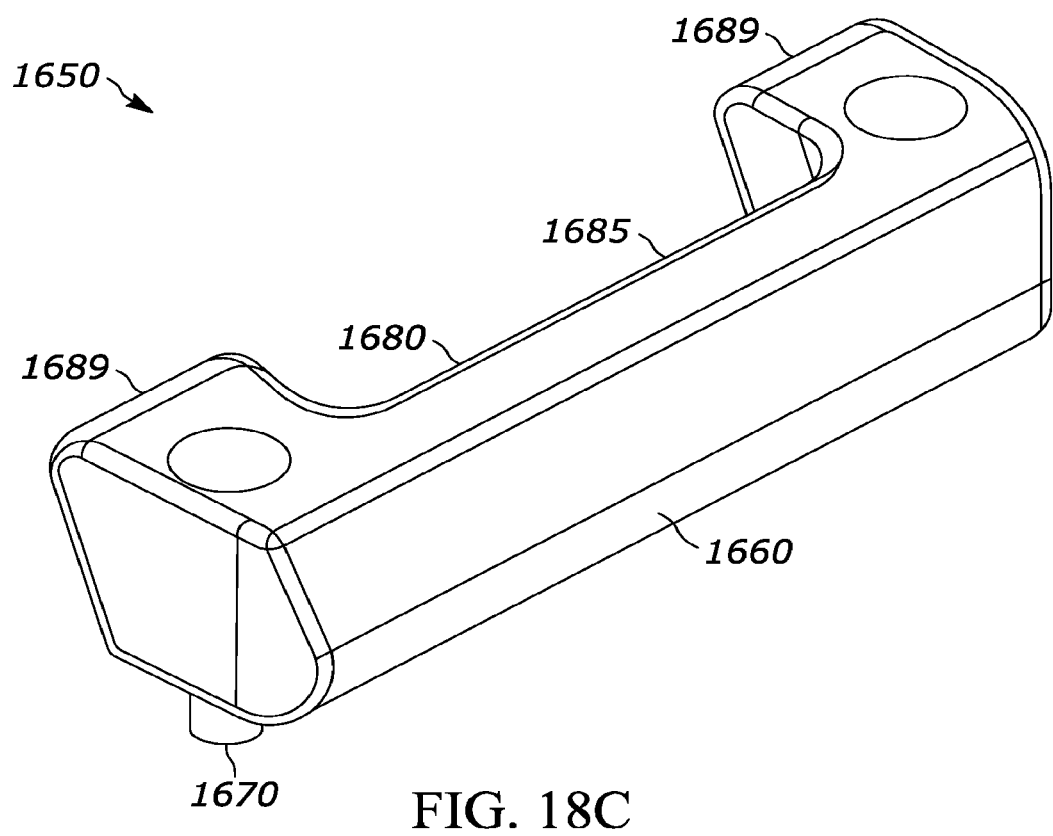
Figure 19A:
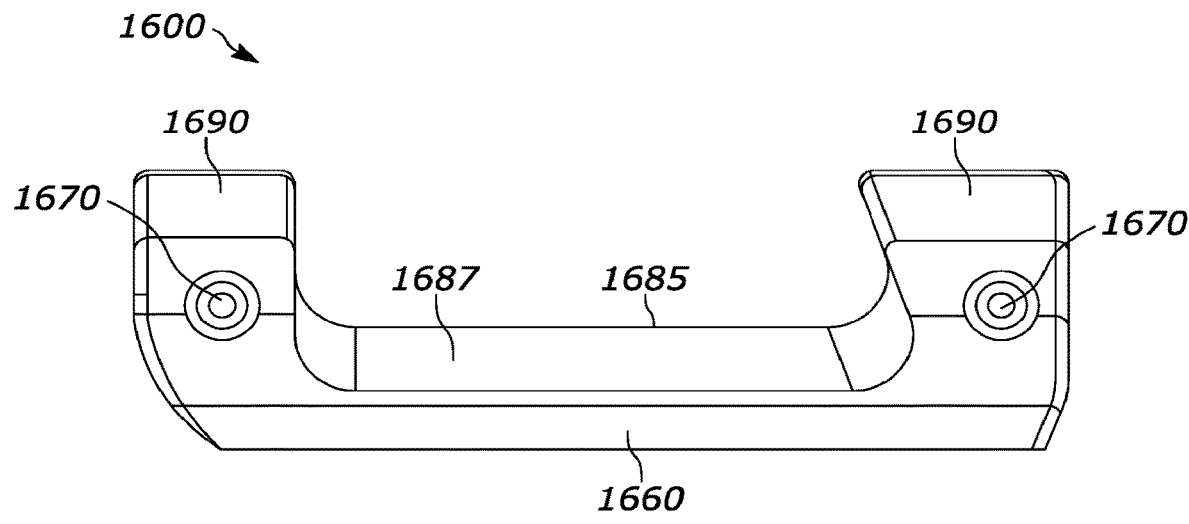
FIGS. 19A-19C show plan views of a dorsal face of the distal pads.
Figure 19B:
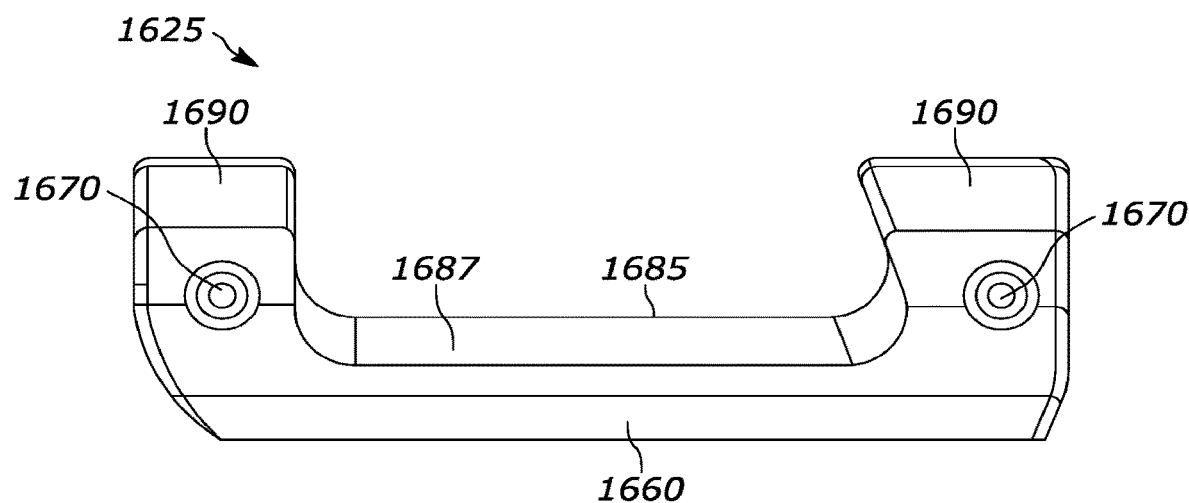
Figure 19C:
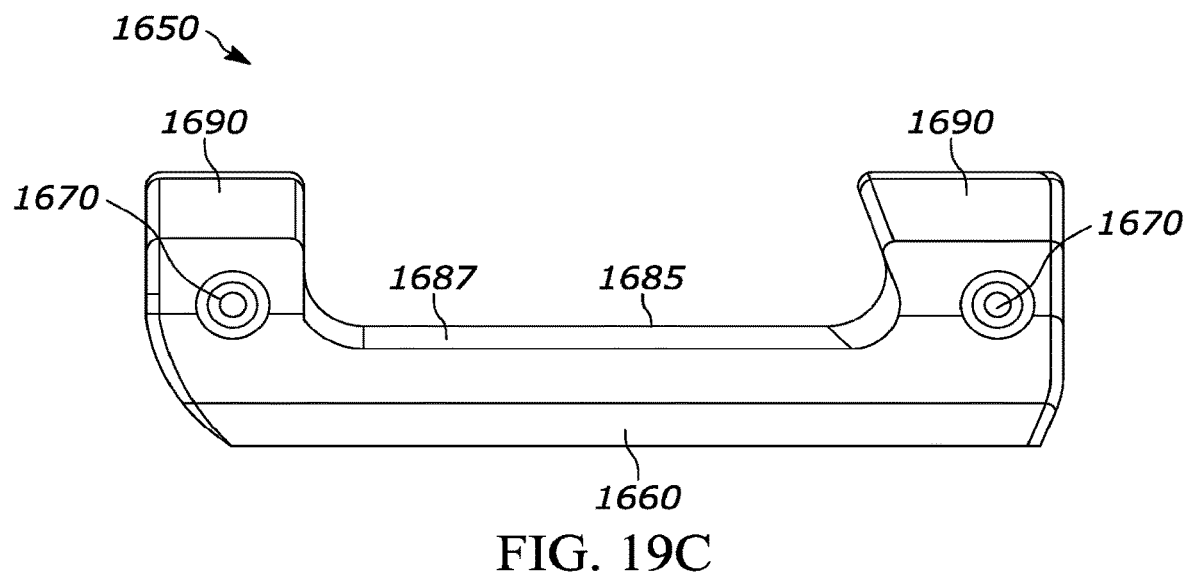
Figure 20A:
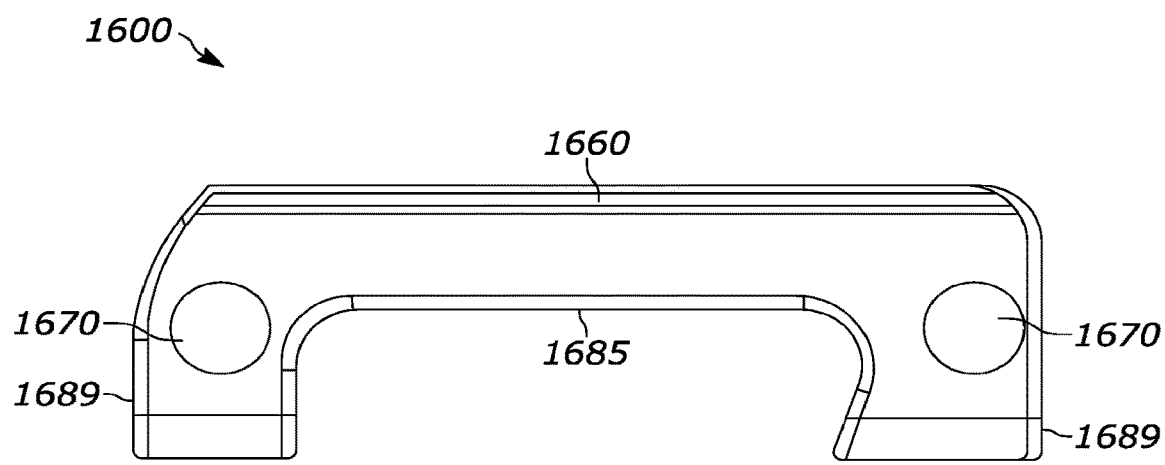
FIGS. 20A-20C show plan views of a volar face of the distal pads.
Figure 20B:
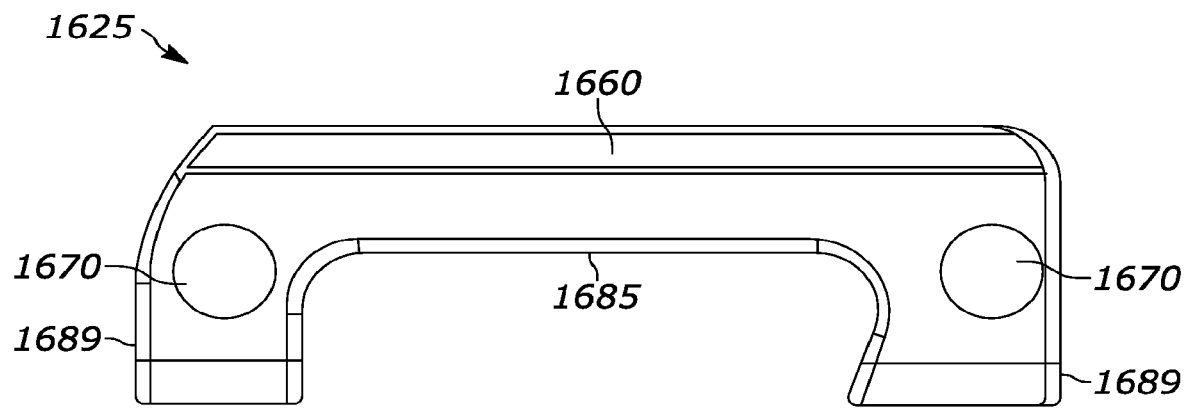
Figure 20C:
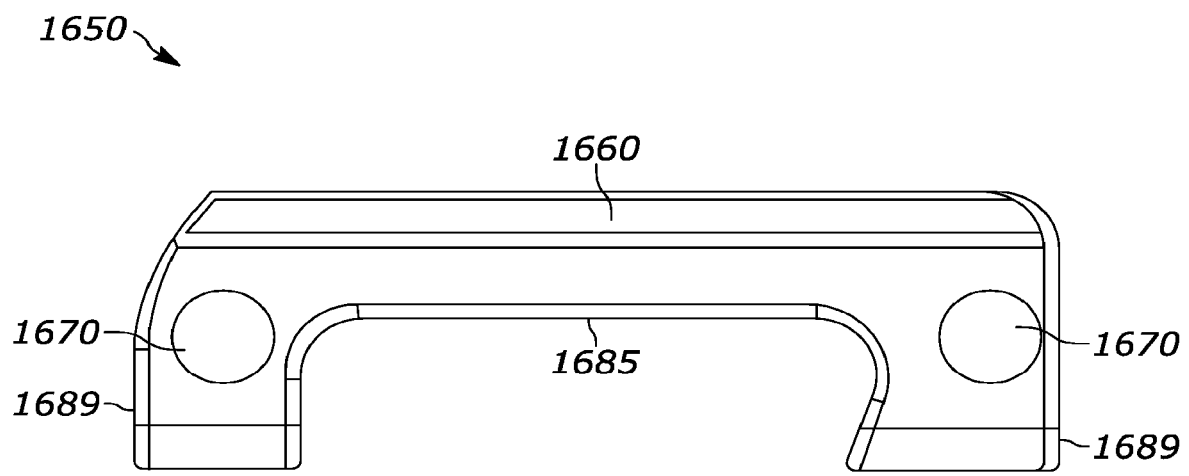

Also note that FIGS. 16A-16C show side elevational views of the distal pads, FIGS. 17A-17C show perspective views of the distal pads from a generally proximal viewpoint, FIGS. 18A-18C show perspective views of the distal pads from a generally distal viewpoint, FIGS. 19A-19C show plan views of a dorsal face of the pads, and FIGS. 20A-20C show plan views of a volar face of the pads.

Save for differences in the thickness of the pads 1600, 1625, 1650, like components may be included on each of the pads 1600, 1625, and 1650, with those components being configured the same on each respective pad. Accordingly, reference will be made mostly to the pad 1600, with like components being similarly configured and arranged on the pads 1625, 1650 as well.

As shown in FIG. 16A, the distal pad 1600 may include a distal face 1660 that is at least partially curved and/or beveled distally (e.g., beveled distally and then curved along a distal-dorsal edge portion of the face 1660 as shown). The curve may be convex. Thus, in at least some examples, the curve of the lower portion of the face 1660 may conform to the volar tilt of the plate at the distal end of the plate 100 (e.g., conform to the curved cross-member 160 of the window portion 130) as described above.

The distal pad 1600 may also include at least one, and preferably but optionally plural, pegs 1670 each engageable with a respective hole 450 in the window portion 130. Each peg 1670 may extend away from a dorsal face of the distal pad 1600, with the dorsal face of the pad 1600 abutting and lying flat against the face 200 when the peg(s) 1670 are fully positioned into respective holes 450. Thus, note that the dorsal face of the pad 1600 may sit flat against the face 200 when the pad 1600 itself is fully engaged with the plate 100.

The pegs 1670 may be cylindrical and integral with the pad 1600. Both the pegs 1670 and pad 1600 may be rigid. The pegs 1670 and pad 1600 may be made of titanium, titanium alloy, stainless steel, cobalt chrome, iron, cobalt, chromium, other metal alloys, tantalum, polyethylene, acrylic, other polymers/plastics, and/or ceramics etc. Additionally, as shown in FIGS. 16A-16C, the pegs 1670 may include a cylindrical end on the dorsal end portion of the respective peg 1670, with the cylindrical end having a diameter less than the diameter of a volar cylindrical segment of the respective peg 1670 that extends dorsally away from the dorsal face of the pad 1600 toward the cylindrical end.

As also shown variously in FIGS. 16A-20C, each distal pad 1600, 1625, 1650 may include a proximal edge portion 1680, with the proximal edge portion 1680 including a proximal edge 1685 establishing a lip. As may be appreciated particularly from FIGS. 17A-17C, this lip may extend in the ulna-radius dimension 135 and also establish a volar edge of a proximal wall 1687. While the wall 1687 may be straight in the volar-dorsal dimension and therefore perpendicular to the volar face of the pad 1600 in certain examples, in the particular example shown in these figures the wall 1687 is instead beveled distally and extends to a dorsal edge at an angle in the range of forty-five degrees to sixty degrees (though distal pads of varying wall degrees may be offered as part of a kit consistent with present principles as well).

Additionally, as also shown in these figures, opposing ends of the lip established by the proximal edge 1685 may curve into side walls forming part of respective proximal knobs 1689. The knobs 1989 may have their own respective lips extending laterally in the ulna-radius dimension 135 to the ulnar and radial ends of the pad 1600, with each knob 1989 establishing a volar edge of a respective wall 1690 that is also beveled distally and extends to a dorsal edge similar to the wall 1687. Further note that the knobs 1989 may extend proximally away from the proximal edge 1685, creating a partial slot for the osteotome to prevent lateral osteotome movement when one of the flat distal end faces of the osteotome are positioned against the wall 1687 for levering. Thus, note that the proximal wall 1687 of the proximal edge portion 1680 may be configured to engage the osteotome, providing a surface against which the osteotome may be positioned during fracture reduction.

Turning to FIGS. 21-25, a second example embodiment of a distal pad 2100 is shown. Many aspects of the distal pad 2100 may be similar in configuration to the pad 1600 as described above, but here the pad 2100 has double-plane beveled proximal wall 2140 rather than a single-plane beveled proximal wall. Thus, while the proximal wall 2140 of the pad 2100 may still be beveled between forty-five and sixty degrees volar-dorsal as described above in reference to wall 1687, the wall 2140 may also be beveled ulnar-radial in a second plane for the radial-ulnar dimension (e.g., also at forty-five to sixty degrees). This two-plane bevel allows pivoting and/or twisting of the osteotome in a swivel fashion when a flat distal face of the osteotome is positioned against the wall 2140 in order to increase radial inclination (the amount that the radial side of the end of the distal radius is longer than the ulnar side of the distal radius) in addition to restoring radial length and volar tilt (as already possible with the pad 1600/face 1687). Thus, a kit consistent with present principles might include the single-plane beveled pads of 1600, 1625, and 1650 of varying thickness, and might also include dual-planed beveled pads of varying thickness as configured per the description of FIGS. 21-25 below.

Figure 21:
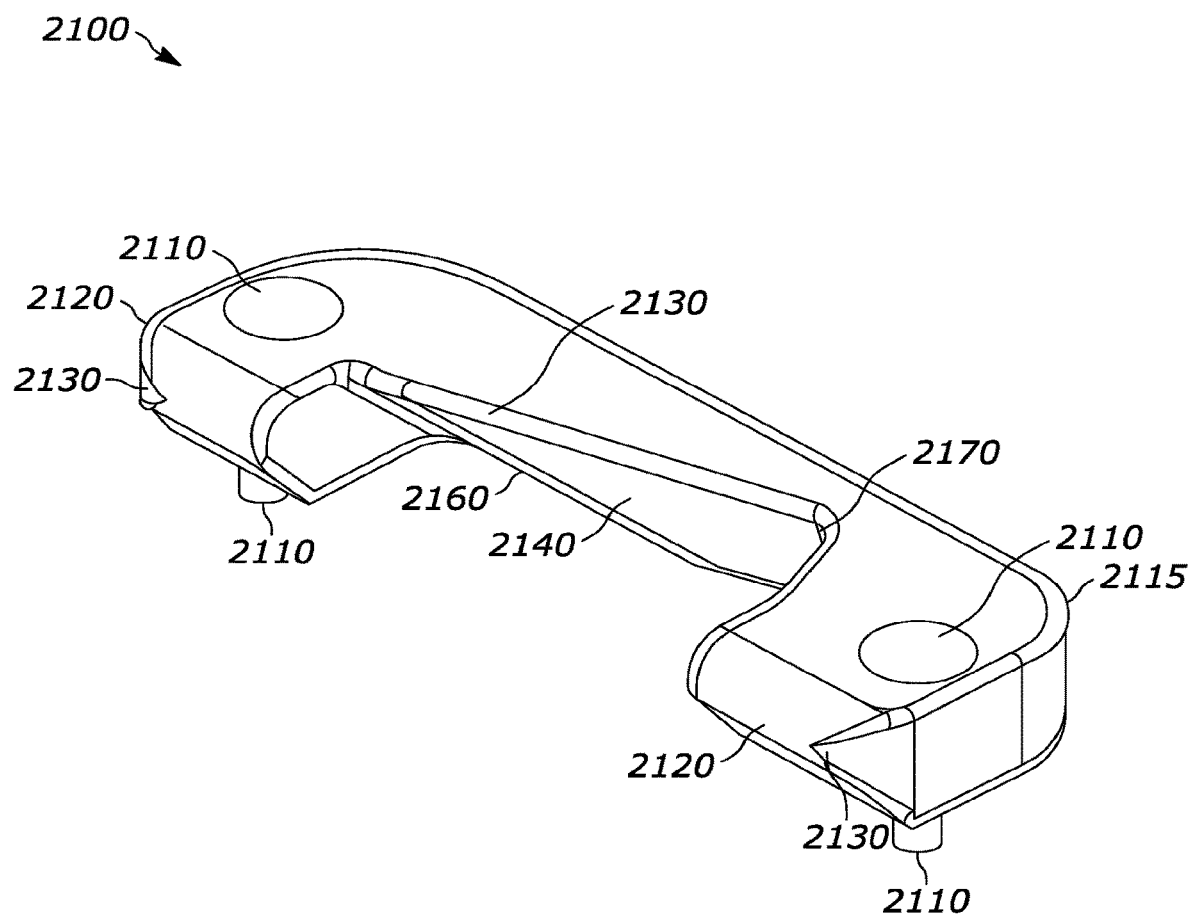
FIG. 21 shows a perspective view from a generally volar-proximal viewpoint of a second example distal pad having a dual-planed bevel consistent with present principles.
Figure 22:
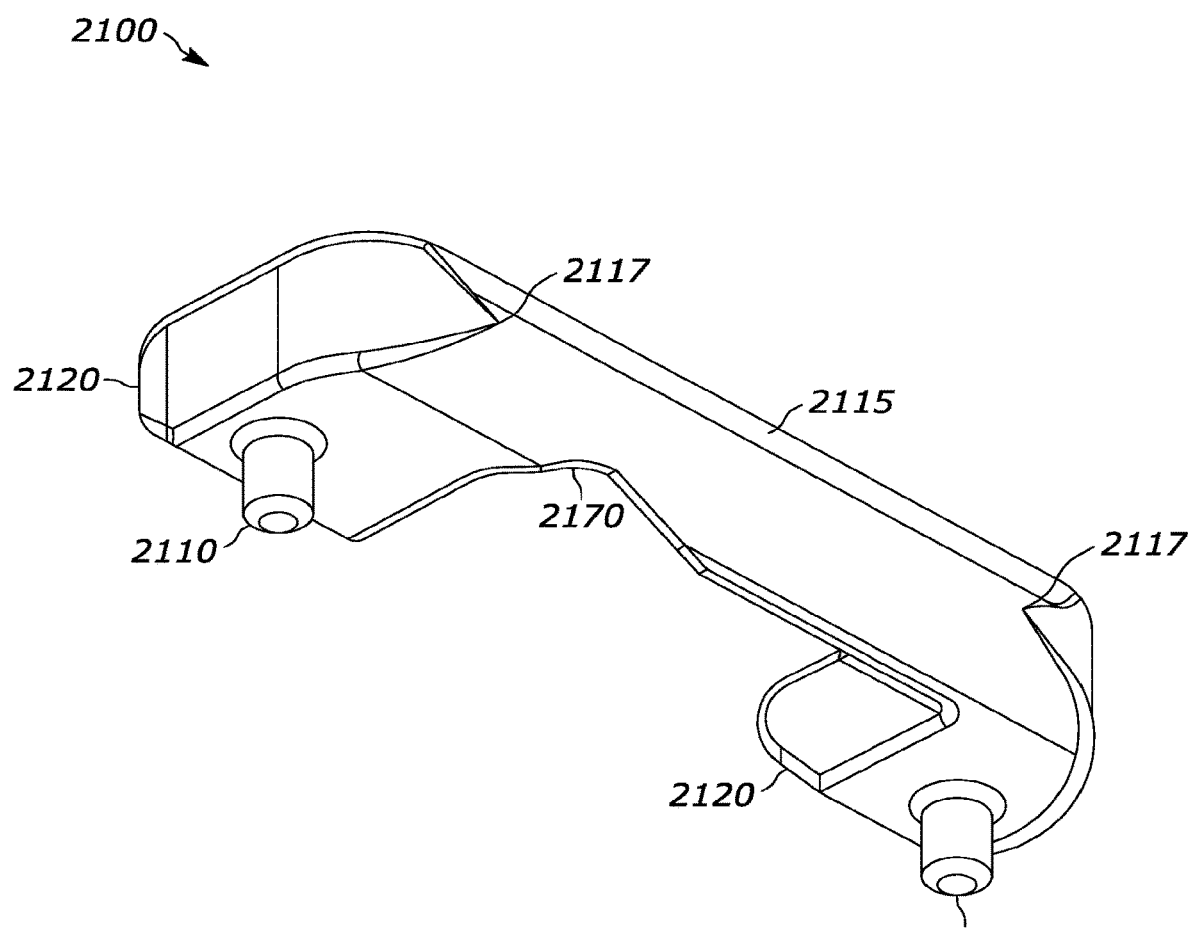
FIG. 22 shows a perspective view of the second example distal pad from a generally dorsal-distal viewpoint.
Figure 23:
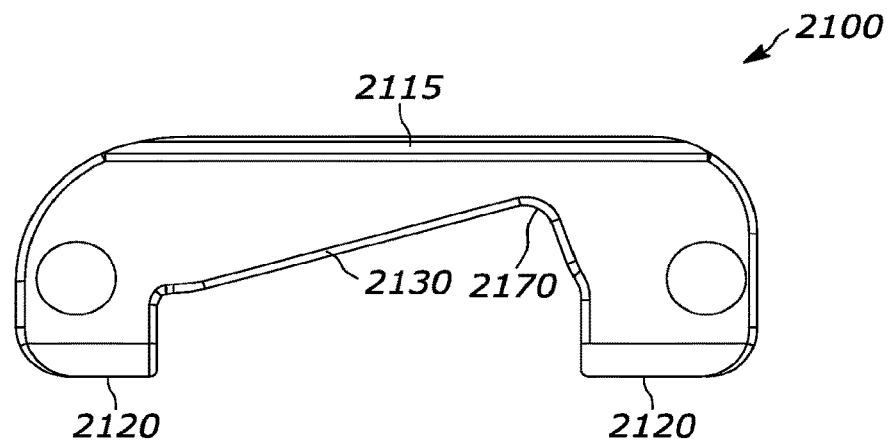
FIG. 23 shows a volar plan view of the second example distal pad.
Figure 24:
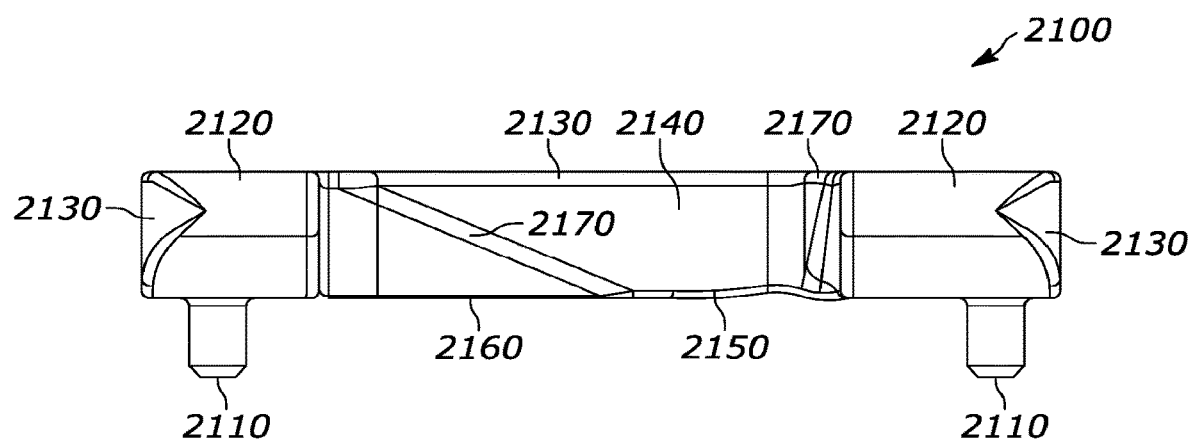
FIG. 24 shows a proximal end side elevational view of the second example distal pad.
Figure 25:
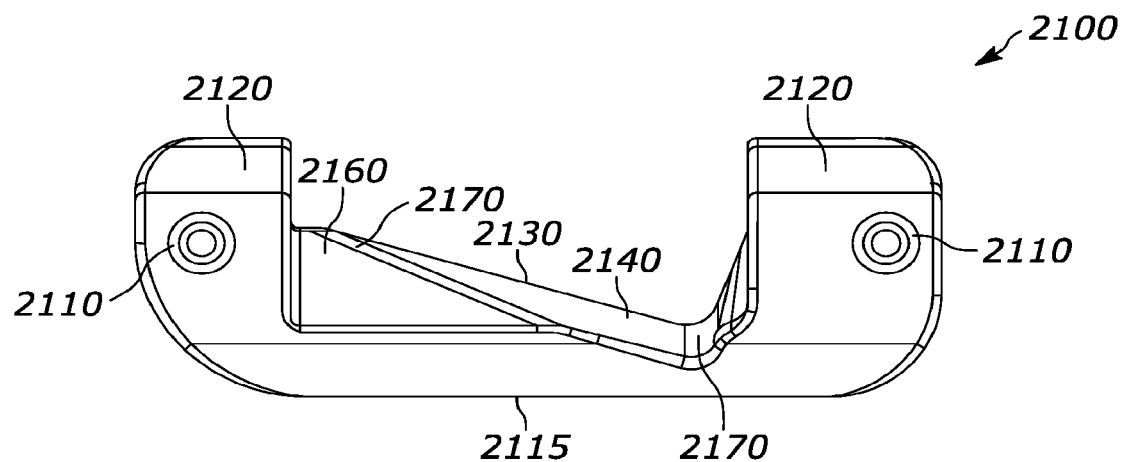
FIG. 25 shows a dorsal plan view of the second example distal pad.
Figure 26A:
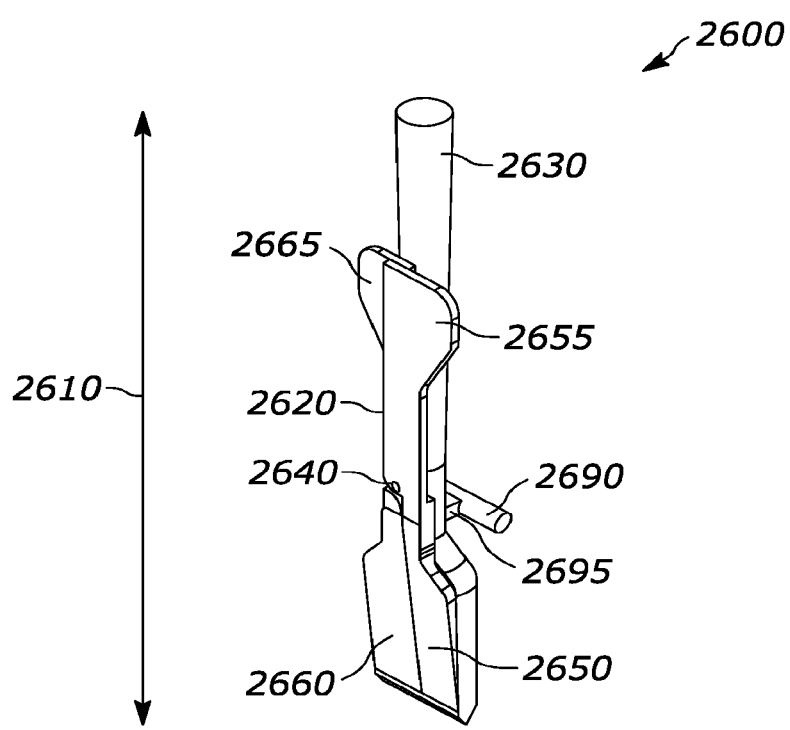
FIGS. 26A-26D show various views of an example fanning osteotome in non-fanned configuration.
Figure 26B:
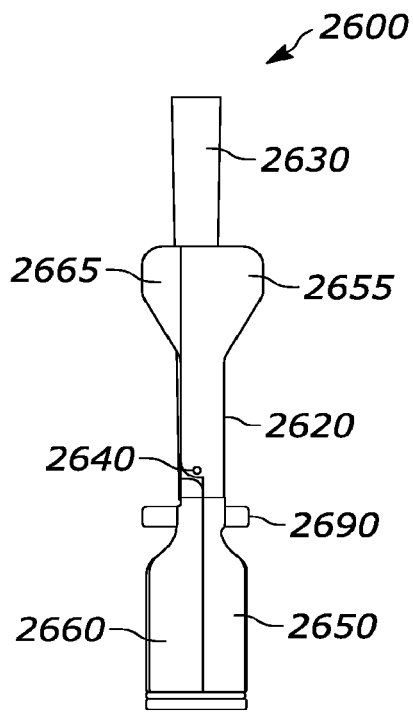
Figure 26C:
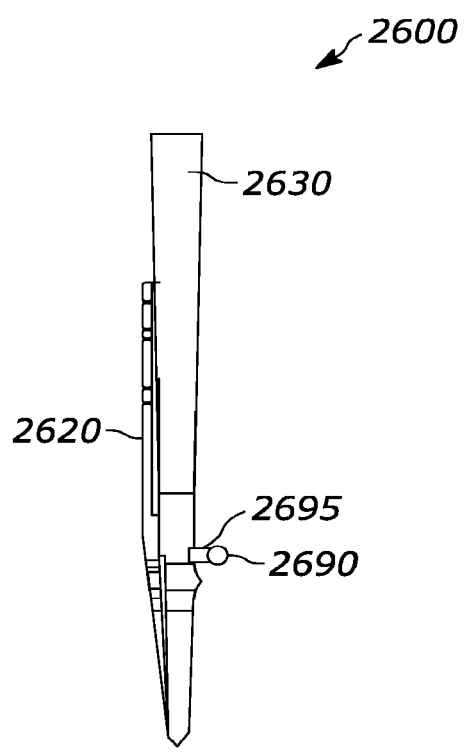
Figure 26D:
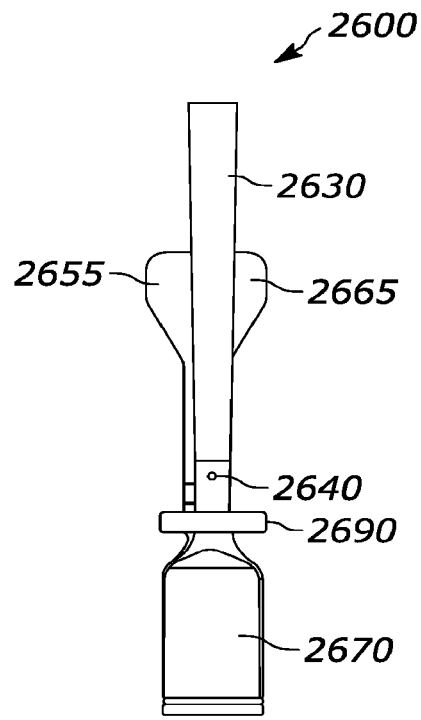
Figure 27A:
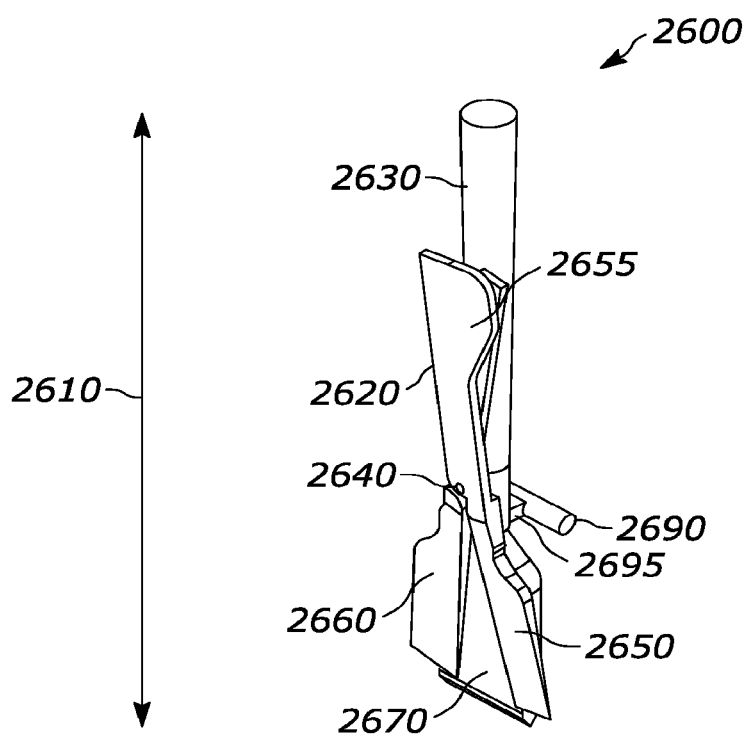
FIGS. 27A-27D show various views of the example fanning osteotome in fanned configuration.
Figure 27B:
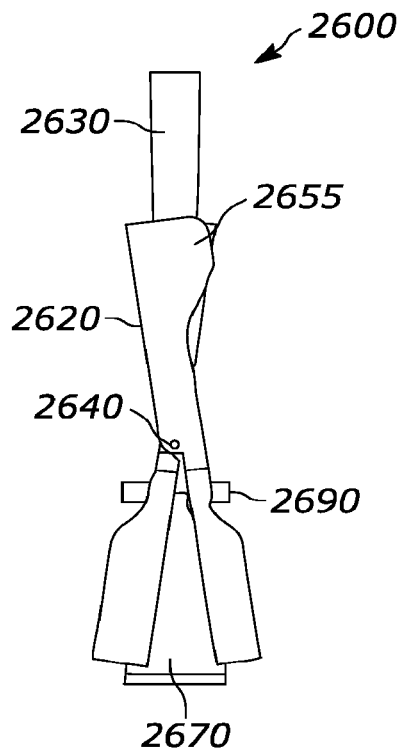
Figure 27C:
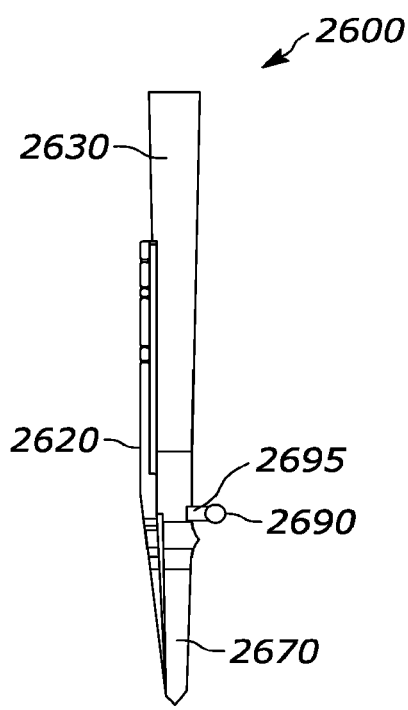
Figure 27D:
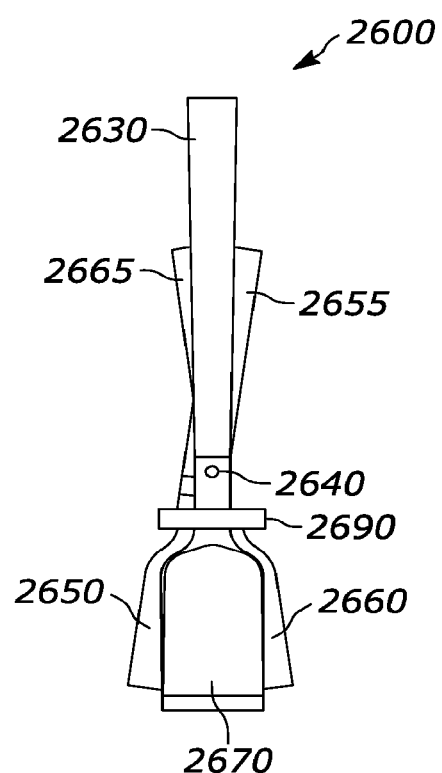

Accordingly, note that FIG. 21 shows a perspective view of the pad 2100 from a generally volar-proximal viewpoint, FIG. 22 shows a perspective view of the pad 2100 from a generally dorsal-distal viewpoint, FIG. 23 shows a top/volar face plan view of the pad 2100, FIG. 24 shows a front/proximal side elevational view of the pad 2100, and FIG. 25 shows a bottom/dorsal face plan view of the pad 2100.

As shown in FIGS. 21-25, the pad 2100 may include pegs 2110 that may be similar to the pegs 1670 and, as such, may be rigid and made integral with the pad 2100. The pad 2100 may also include a distal face 2115 that may be similar to the distal face 1660. The pad 2100 may further include proximal knobs 2120 that may be similar to the proximal knobs 1689 and, as such, may be beveled in a single plane volar to dorsal similar to the knobs 1689. However, further note that the knobs 2120 may in some examples be curved inward at distal outer segments 2130 thereof (distal relative to the main body of the pad 2100), terminating at a point best shown in the front elevational view of FIG. 24. What's more, if desired the knobs 2120 may be curved around the face 2115 at proximal segments (again, proximal relative to the body of the pad 2100), terminating at a respective point 2117 on the face 2115 best shown in FIG. 22.

As also shown in these figures, the pad 2100 may include a proximal edge 2130 establishing a lip (proximal relative to the patient). As may be appreciated from FIG. 21 for example, this lip may extend in the ulna-radius dimension and also be sloped obliquely and distally toward the radial side of the pad 2100 as shown. The lip may thus establish a volar edge of a proximal wall 2140. As mentioned above and perhaps best shown in FIG. 21, the wall 2140 may be beveled volar to dorsal and also beveled ulnar to radial. As shown in FIG. 24, at least part of the wall 2140 may extend to a dorsal edge 2150, with other portions of the wall 2140 terminating at another wall 2160 or transitional curved or beveled surface 2170 between the walls 2140 and 2160. The wall 2160 may be beveled in a single dimension, volar to dorsal, and also extend to the dorsal edge 2150. Thus, note that the wall 2160 is only beveled in a single plane, volar-dorsal similar to the wall 1687 already described above. Accordingly, depending on stage of distal radius fracture reduction, a flat distal surface of the osteotome may be positioned against either wall 2140 or 2160 for leverage for desired fracture reduction. Also note that the lip 2130, wall 2140, and radial-side knob 2120 may together form a notch 2170 into which a longitudinal edge of the osteotome may be placed to further aid in twisting and/or swiveling of the osteotome to increase radial inclination. Yet the distal radius may still be elongated by levering the osteotome against the wall 2160 when desired.

Now in cross-reference to FIGS. 26A-D and FIGS. 27A-D, a reduction osteotome 2600 with fanning capability is shown and may be used with a RIVAR plate, proximal pad, and distal pad consistent with present principles. FIGS. 26A-D show the osteotome 2600 in collapsed/unfanned position, while FIGS. 27A-D show the osteotome 2600 as fanned outward (explained in greater detail below). For both of FIGS. 26A-D and 27A-D, note that the "A" figures show perspective views of the osteotome 2600, the "B' figures show front elevational views of the osteotome 2600, the "C' figures show side elevational views of the osteotome 2600, and the "D" figures show rear elevational views of the osteotome 2600. And though not shown in this figure, note that the osteotome 2600 may also have a slider, which may be locked into place with a locking screw if desired and as further set forth below.

As shown in these figures, the osteotome 2600 includes a fanning mechanism 2620 extending longitudinally along, and coupled, to a longitudinal osteotome bar 2630. The mechanism 2620 may be coupled to the bar 2630 via a pin or screw 2640 about which rotating bars 2650, 2660 of the mechanism 2620 may rotate with respect to each other. But further note that a rear distal end osteotome member 2670 remains stationary with respect to the bar 2630. The distal member 2670 may be rigid and integral with the bar 2630 and can be used for fracture reduction, with it being further noted that the bars 2650, 2660 may also be rigid and fanned in or out as needed to further aid with reduction via distal end segments of the bars 2650, 2660. For example, the bars 2650, 2660 may be fanned outward to a position that matches the width of the distal radius. Also note that the distal ends of the bars 2650, 2660, and member 2670 may each include opposing flat surfaces as shown that face frontwards and backwards, with the front to back thickness of the distal end segment of the bar 2670 being a 1 mm (millimeter) thick rigid/non-flexible blade that can slice through bone. Or the combined thickness of the distal end segments of the bars 2650, 2660, and 2670 may be 1 mm.

The bars/struts 2650, 2660 may themselves be fanned based on a physician laterally pinching or squeezing respective handles 2655, 2665 of the mechanism 1620 inward together, with the handles 2655, 2665 as located at proximal ends of the bars 2650, 2660. This in turn causes the bars 2650, 2660 to rotate about the pin/hinge 2640 for the generally rectangular flat distal ends of the bars 2650, 2660 to fan laterally outward as well as proximally upward in semi-circular fashion such that the distal ends scissor back and forth with respect to each other to form a laterally wider or narrower surface for distal radial fracture reduction as needed, with this wider or narrower surface collectively formed by both the distal ends if the bars 2650, 2660 that scissor as well as the stationary distal member 2670. FIGS. 26A-D therefore show the bars 2650, 2660 in closed configuration in which respective inner vertical edges of the distal ends abut each other, while FIGS. 27A-D show the bars 2650, 2660 in open configuration in which the distal ends of the bars 2650, 2660 are spaced from each other but are still generally oriented with flat front surfaces in a plane(s) that is parallel to the plane of the flat front surface of the stationary distal member 2670. Thus, per FIGS. 27A-D, the flat front and rear surface areas of the distal ends of the osteotome 2600 may be increased more or less as needed for fracture reduction by pinching the handles 2655, 2665 more or less. Additionally, in some examples the mechanism 2620 may include a spring mechanism (not shown) to keep the bars 2650, 2660 in the closed configuration of FIGS. 26A-D under spring bias, which may be overcome by a physician pinching the handles 2655, 2665 together.

FIGS. 26A-27D also show a lateral bar 2690 that may be placed in the aforementioned hooks of a proximal pad as described above to hold the osteotome in position while definitive fixation is performed on the distal fragment(s). The bar 2690 may be made integral with the bar 2630 and may be spaced from the bar 2630 by an integral support member 2695 extending back and away from the bar 2630. The bar 2690 may therefore be used to rotate the osteotome about an axis defined by the longitudinal axis of the bar 2690 itself once the bar 2690 has been positioned into the hooks of the proximal pad.

Note that some or all of the components of the osteotome 2600 may be rigid and made of titanium, titanium alloy, stainless steel, cobalt chrome, iron, cobalt, chromium, other metal alloys, tantalum, polyethylene, acrylic, other polymers/plastics, and/or ceramics etc. Further note that although not shown for simplicity, the osteotome 2600 may include bold "cm" markings on both front and back surfaces, spaced longitudinally along on the osteotome 2600 so that the surgeon knows the depth of penetration across the fracture site as expressed in centimeters.

Figure 28:
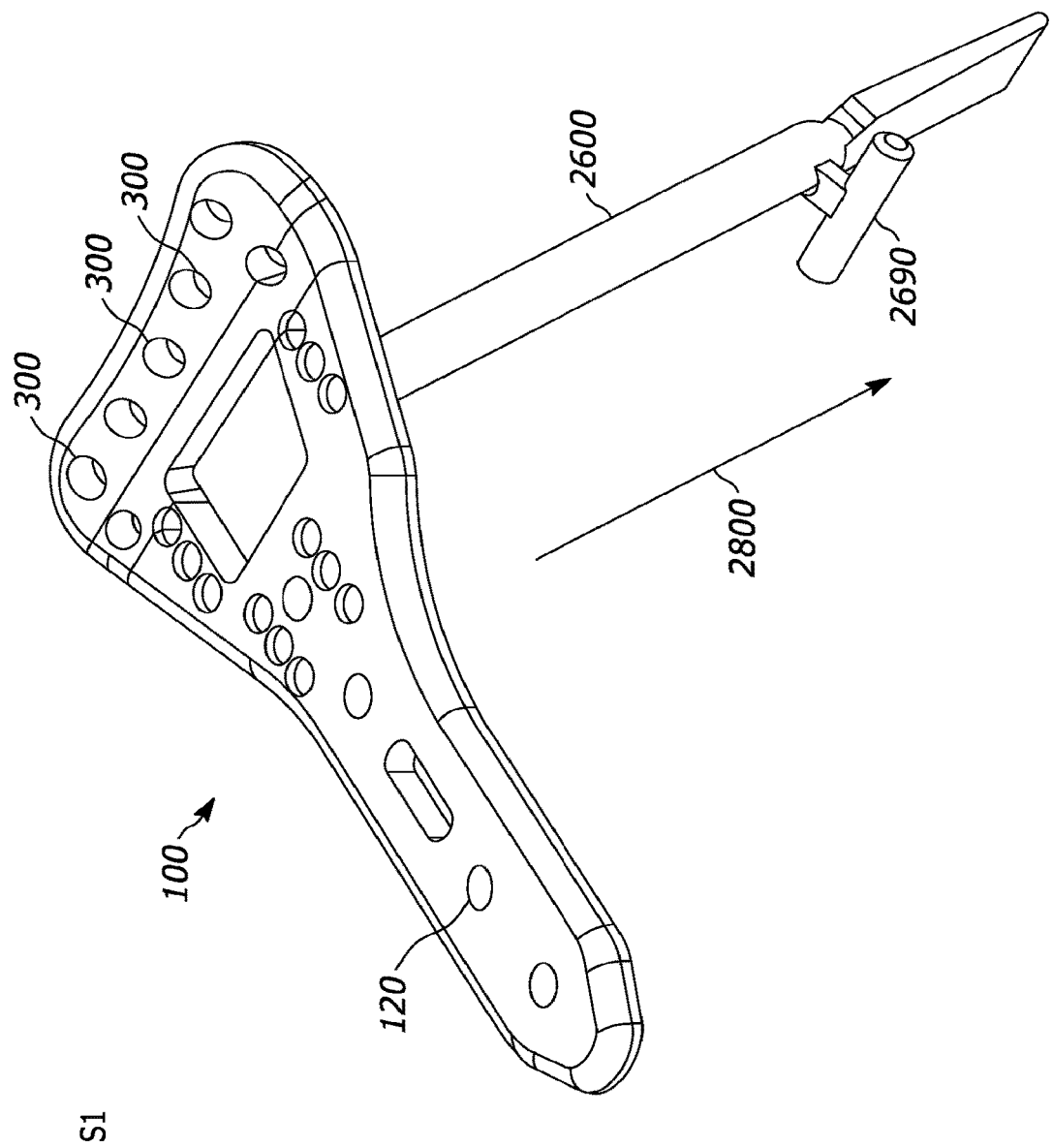
FIG. 28 graphically shows various method steps that may be performed to engage proximal and distal pads with a RIVAR plate and to reduce a bone fracture consistent with present principles.
Figure 28:
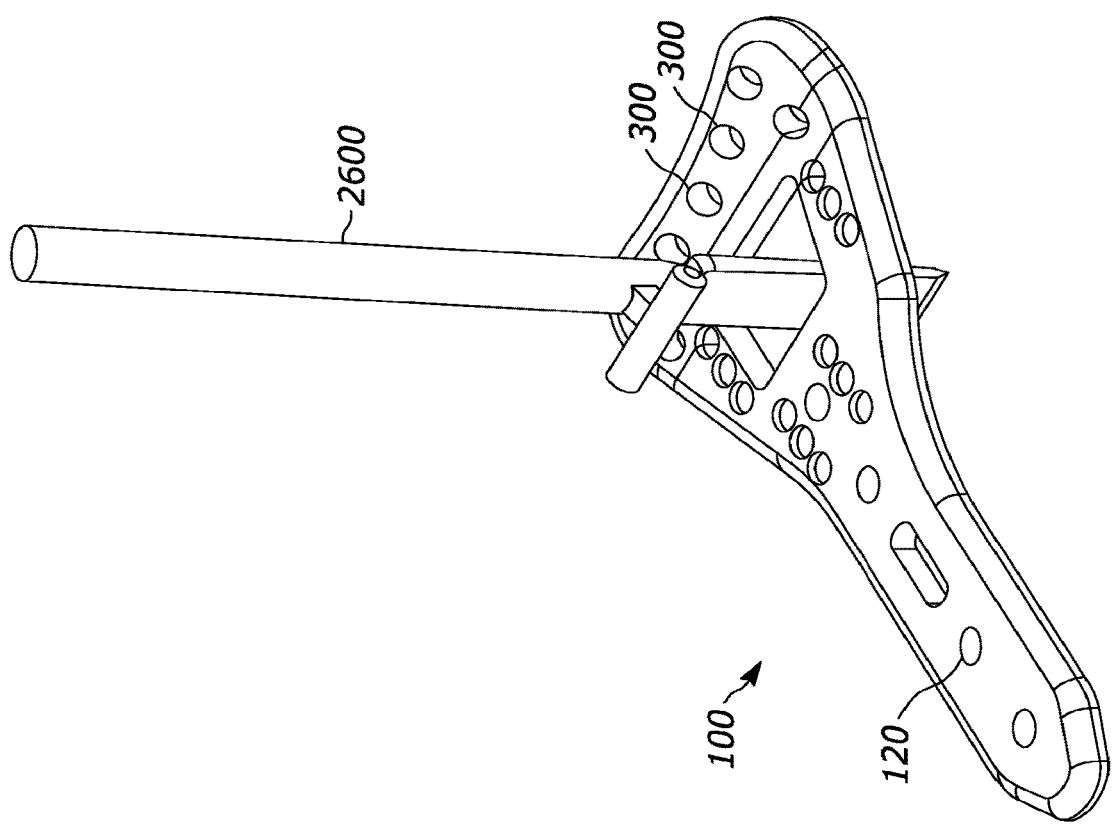
Figure 28:
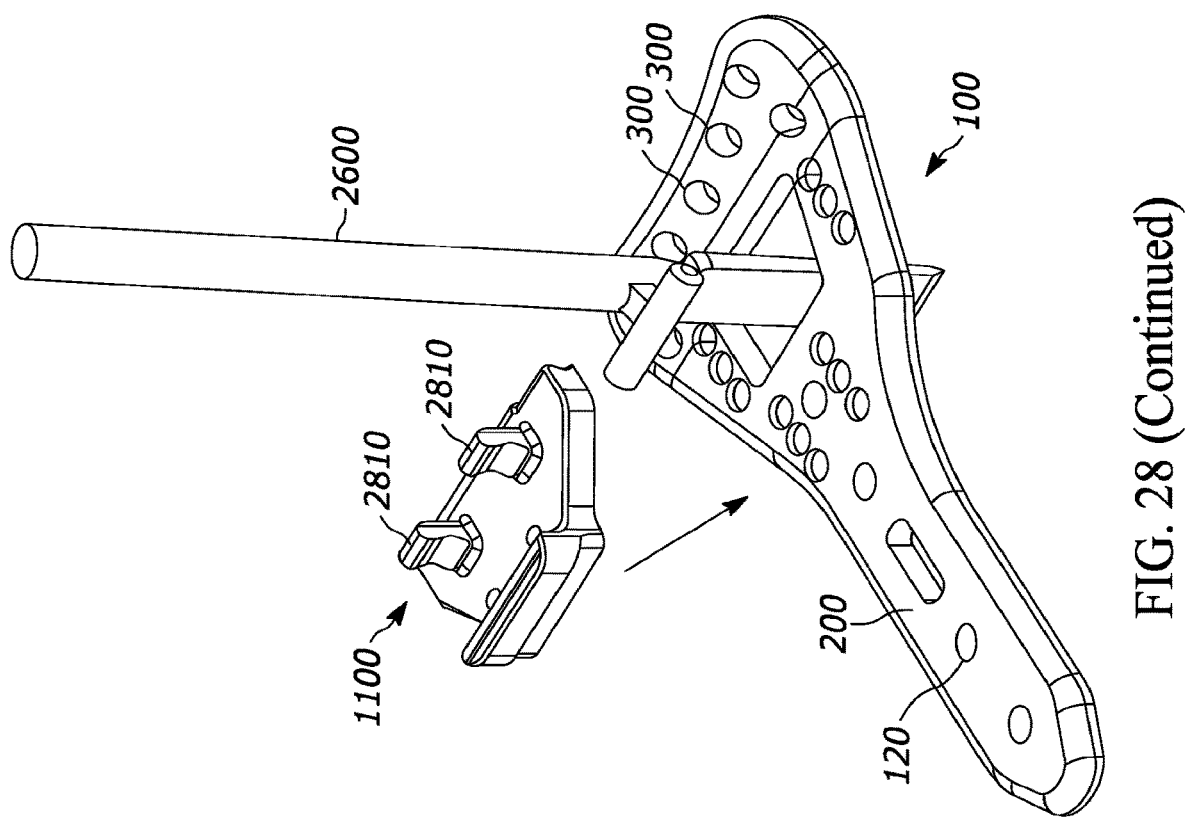
Figure 28:
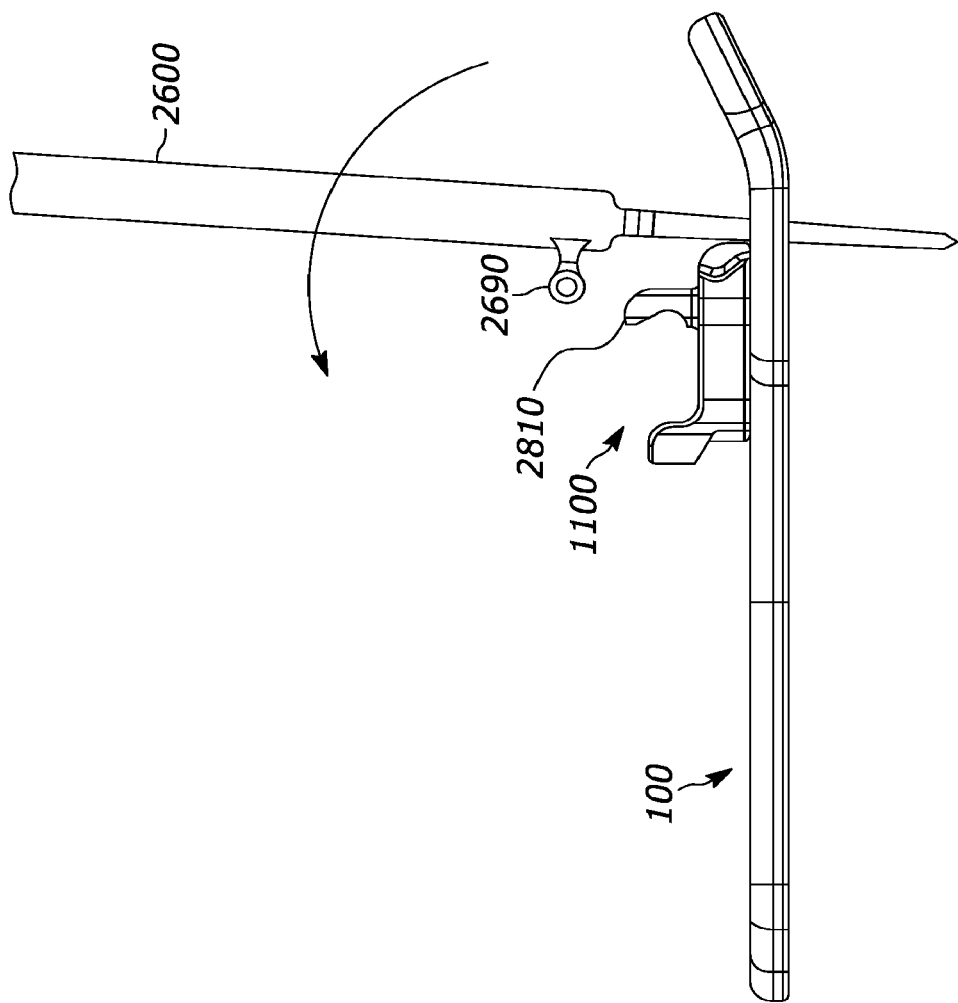
Figure 28:
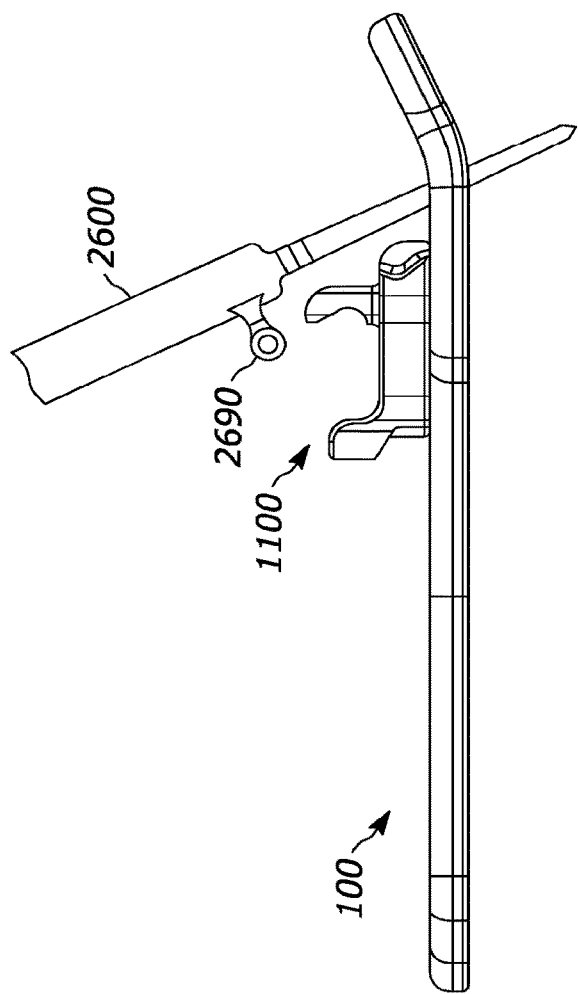
Figure 28:
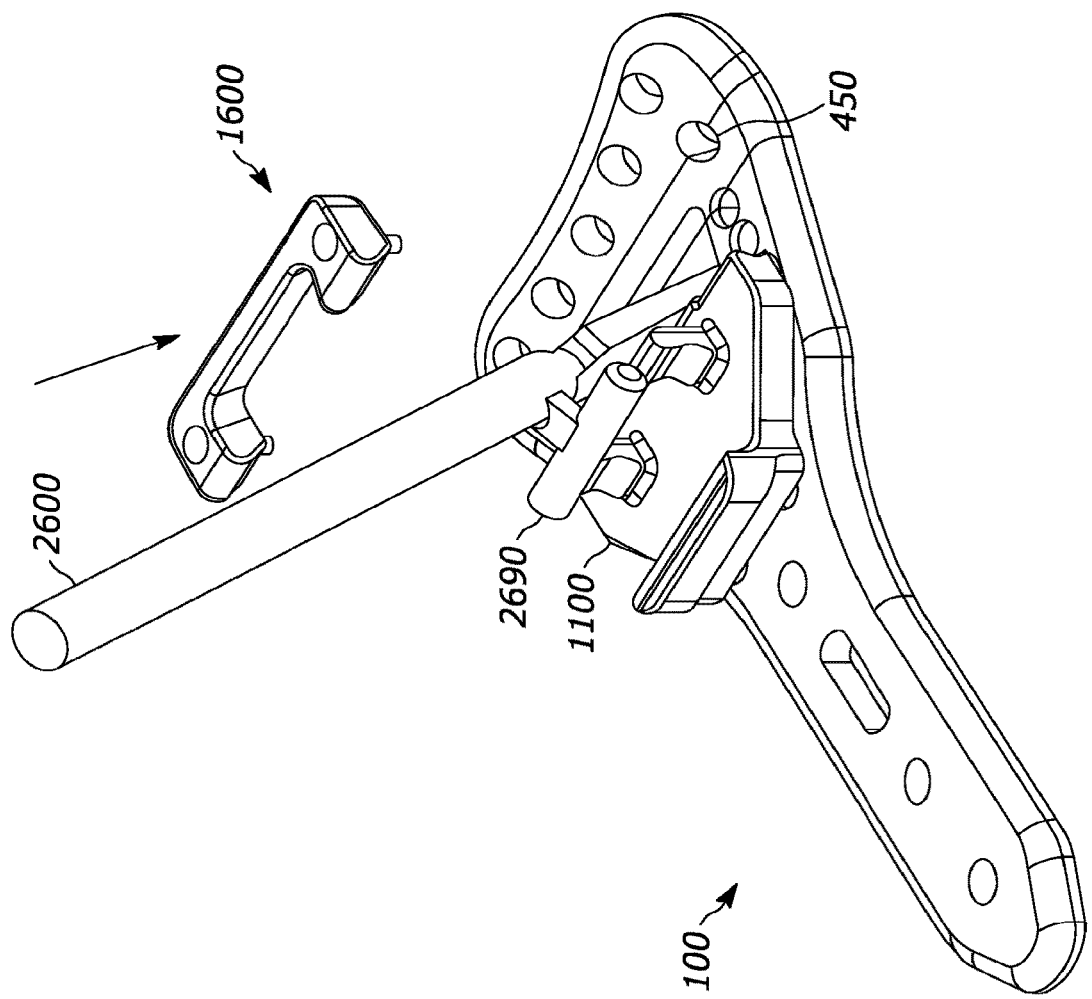
Figure 28:
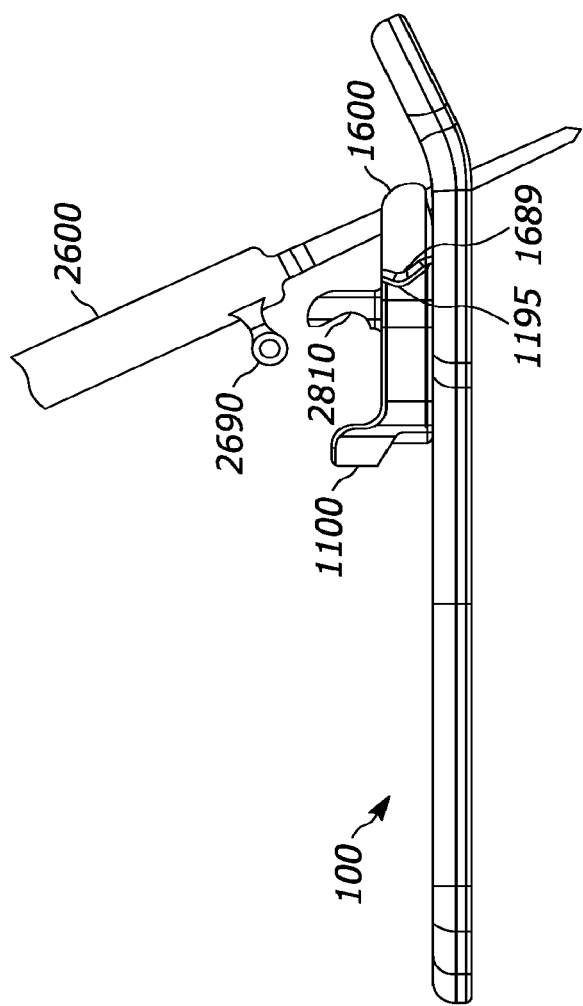
Figure 28:
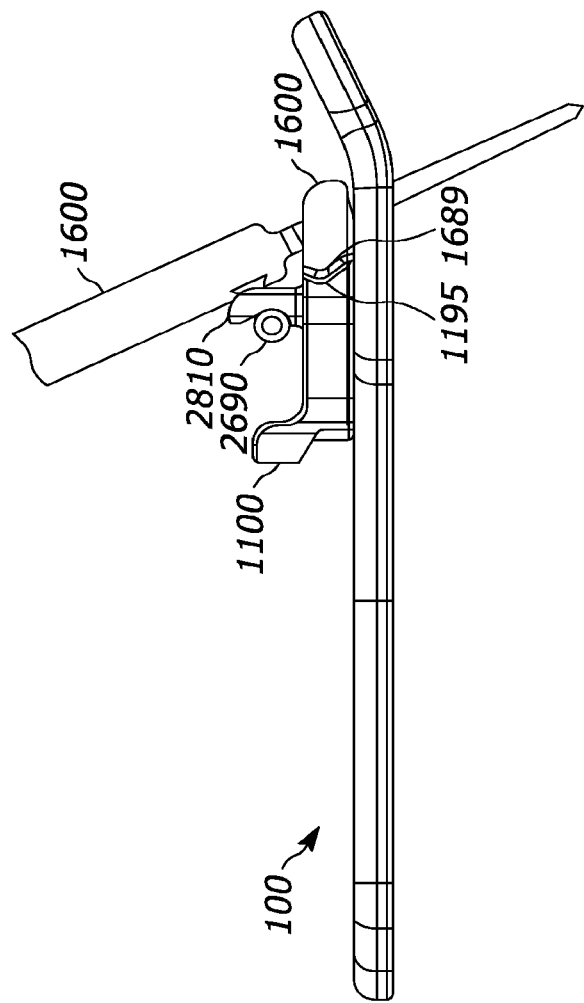

Continuing the detailed description in reference to FIG. 28, a graphical flow chart is shown that demonstrates steps for engagement of a RIVAR plate, proximal and distal pads, and an osteotome with a patient to reduce a distal radial fracture consistent with present principles.

As shown at Step S1, the reduction osteotome 2600 is placed from volar to dorsal through the fracture site and then the plate 100 is slid down the osteotome 2600 through the window 170 (or window 800), as demonstrated via arrow 2800, until the bar 2690 passes through the window 170 as shown in Step S2. In at least some instances and prior to sliding the plate 100 down, the osteotome 2600 may be placed perpendicular to the volar surface of the radius and angled slightly dorsal proximal. Also in at least some instances and prior to sliding the plate 100 down, the osteotome 2600 may be pushed dorsally just past the dorsal cortex.

Then, if the radius is not shortened but volar tilt is to still be restored, the plate 100 may be fixed to the volar edge of the distal fragment to serve as a hinge. The holes 300 on the distal edge of the plate 100 may then be used, with small K wires being passed therethrough and into the volar cortex of the distal fragment, fixing the plate 100 to the distal radius. Care may be taken to place the plate 100 such that the distal end of the plate is disposed proximal to the watershed line of the distal radius. However, if radial lengthening is desired, an x-ray may first be taken of the uninjured opposite wrist and the ideal/desired position of the plate 100 relative to the ulna may be defined for the injured wrist based on the x-ray so that the lengths of the healthy and injured radii may match or come close to it. This aspect may be performed during Step S2.

Additionally, though not shown, as an intervening step between steps S2 and S3, one or more fasteners 125 may be placed in one or more respective holes 120 of the plate 100 to secure the plate 100 to the radial shaft. Then fracture-reduction proximal and distal pads of appropriate thickness, depending on the nature of the fracture and the desired lengthening of the radius, may be selected.

Also note that in some examples, the plate 100 may instead be provisionally attached to the volar side of the distal radius and then the osteotome 2600 may enter the fracture site as described above through the window 170 and across the fracture (e.g., either perpendicular to the volar surface, or with the proximal handle of the osteotome 2600 disposed away from the arm and toward the hand). In this way, the plate need not be rotated to get around the bar 2690 as the plate 100 is slid down the osteotome 2600 through the window 170 per the description above, since the plate 100 is positioned against the patient before the osteotome contacts the patient.

Step S3 then shows that a proximal pad 1100 of a desired thickness may be attached to the volar side 200 of the plate 100, using the pegs 1160 to engage a lateral set of holes 400 to affix the pad 1100 to the plate 100. Note that a given lateral set of holes 400 (the sets being respectively spaced longitudinally from other sets on the plate 100) may be selected based on the location of the fracture. Also note that the greater the radial lengthening desired, the thicker the reduction pad that may be used (for both proximal and distal pads 1100, 1600).

Step S4 then shows that the osteotome may be levered proximally so that, at step S5, the lateral bar 2690 may be juxtaposed near the hook 2810 of the proximal pad 1100 (again, with the hook 2810 being formed at least in part by the groove 1175/lip 1177). Then at Step S6, a distal pad 1600 of desired thickness (e.g., same thickness as proximal pad that is selected) may be attached to the volar side 200 of the plate 100, using the pegs 1670 to engage a lateral set of holes 450 to affix the pad 1600 to the plate 100. Note that here too a given lateral set of holes 450 (the sets being spaced longitudinally from other sets on the plate 100) may be selected based on the location of the fracture and so that a narrow slit for the osteotome is created between the two pads. Also note that if an increase in radial inclination is desired as part of distal radial fracture reduction, then a distal reduction pad with a radial swivel can be used (e.g., the pad 2100 described above) rather than the pad 1600. Steps S7 and S8 then indicate that the lateral bar 2690 of the osteotome 2600 may be manipulated down and into the hook 2810 once both pads 1100, 1600 are secured to the plate 100.

Also note per Steps S7 and S8 that the grooves 1195 on the proximal pad 1100 may closely receive and engage with the proximal knobs 1689 of the distal pad 1600 to help lock the pads 1100, 1600 in place on the plate 100 and with respect to each other. Further note that to engage the distal pad 1600 with both the proximal pad 1100 and plate 100 itself, the knobs 1689 may be placed in the grooves 1195 before the pegs 1670 of the distal pad 1600 are engaged with the holes 450. Then once the knobs 1689 are within the grooves 1195, the distal pad may be swiveled down to extend the pegs 1670 into the holes 450.

Step S8 therefore shows that the osteotome 2600 may be engaged with the plate 100 itself via the hooks 2810, locking the osteotome 2600 to the plate 100 while still allowing a swinging, radial movement about the lateral hinge axis that results from the bar 2690 engaging the hooks 2810.

Also note that in some examples, the distal pad 1600 may be affixed to the plate 100 before the proximal pad 1100, rather than the other way around as described above. But either way, the osteotome 2600 may still be levered toward the body against the surface(s) of the pads and hooked onto the hooks 2810 for initial fracture reduction.

Any further reductions may be performed using the osteotome, plate and pads, and the plate 100 may then be affixed to the patient via the fasteners 125 and holes 120, 300.

Figure 29:
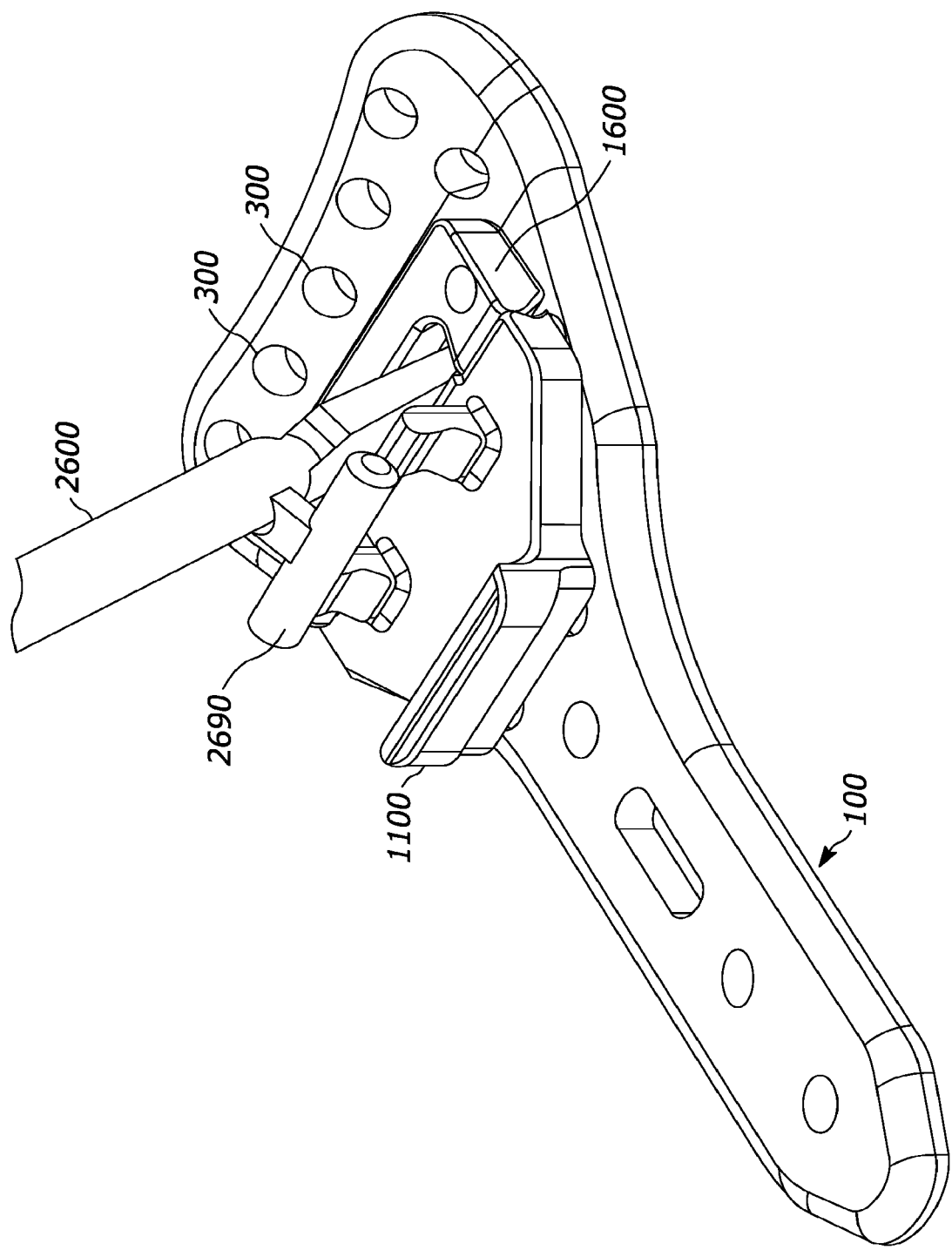
FIG. 29 shows a perspective view of an example RIVAR plate engaged with a proximal pad, a distal pad, and an osteotome consistent with present principles.

FIG. 29 shows a perspective view of the plate 100, proximal pad 1100, distal pad 1600, and osteotome 1600 when fully engaged with each other in this manner for fracture reduction. Additionally, as may be appreciated from FIG. 29, the distal pad 1600 does not extend distally to the point where it would obstruct the holes 300, allowing screws and/or K-wires to be placed in the distal fragment while the distal pad is in place and the plate 100 and pads otherwise affixed to the patient.

As for specific aspects of the reduction procedure itself, note that once the plate and pads have been assembled together and affixed to the patient per FIG. 29, the reduction osteotome 2600 may be levered within the reduction window 170 from distal to proximal (with the distal edge 1190 of the proximal pad 1100 being the fulcrum for the osteotome), restoring the volar tilt. The reduction osteotome 2600 can then be held in this position with the bar 2690 that both limits the depth of penetration of the osteotome 2600 (via the configuration of the hooks 2810 and volar surface of the pad 1100) and locks the bar 2690 into the hooks 2810 of the proximal reduction pad 1100.

Screws or other fasteners may then be extended through the holes 120, 300 as appropriate to fasten the plate 100 to the volar side of the distal radius. Once all screws are placed and fracture alignment is confirmed, the reduction osteotome 2600 may be removed, and the pads 1100 and 1600 may also be disengaged from the plate 100 and removed from the patient. If desired, at this point a bone graft may then be placed through the reduction window 170. The patient may then be sutured up, with the plate 100 remaining in the patient but not the pads or osteotome.

Accordingly, the RIVAR plate system described above may allow for reduction or restoration of anatomic volar tilt and maintenance of this tilt while the plate is applied for stabilization. The plate may accept one of several different reduction pads of varying thickness. The thicker the plate and/or pads, the farther the osteotome fulcrum 1190 is from the bone and the greater the amount of lengthening possible along with restoration of the volar tilt. If desired, a distal pad may even include a swivel option and/or a fixed radial angulation as described for the pad 2100 so that the radial inclination can be restored with the volar tilt. Also note that different iterations of the plate 100 may be configured for left or right arms, as well as the plate being wider or narrower in the ulnar-radius dimension in various iterations to match the width of the radius itself.

Further elaborating on a surgical technique that may be used consistent with present principles, note that preoperative x-rays may first be taken of both wrists to assess the degree of shortening for the fractured radius. If there is no shortening of the injured radius, the RIVAR plate 100 may be fixed to the volar surface of the distal radius just short of the watershed line. If there is shortening of the radius, then the correct position of the plate relative to the ulna may be determined by the x-ray of the opposite wrist, and the RIVAR plate 100 may be fixed in the appropriate position, relative to the ulna, with no screws in the distal fragment.

The reduction osteotome may then be pushed across the fracture until the far end of the osteotome just past the dorsal cortex.

The distal reduction pad may then be snapped into place. If greater lengthening is desired, a thicker plate may be utilized. Thereafter, the proximal reduction pad may be snapped into place.

The reduction osteotome may then be levered from distal to proximal (e.g., pulled back toward body), reducing the fracture by restoring radius length and volar tilt. The osteotome may then be engaged into the "capture" hooks/extensions 1170 on the proximal pad, holding the osteotome in place and hence helping to maintain the facture reduction just performed.

A fluoroscopic x-ray may then be taken. Based on the x-ray, if reduction is acceptable, then screws may be placed in the distal holes (e.g., holes 300) of the plate 100 and into the distal fragment(s). Additionally, K-wires can be placed across the fracture from the tip of the radial styloid.

If reduction is not acceptable, the distal and proximal pads may be exchanged (e.g., add a radial inclination distal pad, exchange both pads for thicker pads, etc.). Leverage reduction may then be repeated as described above. This part of the process may repeat until reduction is acceptable (e.g., as confirmed through additional x-rays).

The osteotome may then be removed, and the pads may also be removed.

Additional screws can be applied through the screw holes along the plate (e.g., holes 120) and fixation of the distal fragments of the radius may also be performed by fastening the fragments to the plate through the plate's distal holes (e.g., holes 300). Remaining proximal holes may then be filled with fasteners to mount to the radius, and/or filled with filler material if not being used.

A bone graft can also be placed into the area of the reduction window before covering with the pronator quadratus during closure.

Figure 30A:
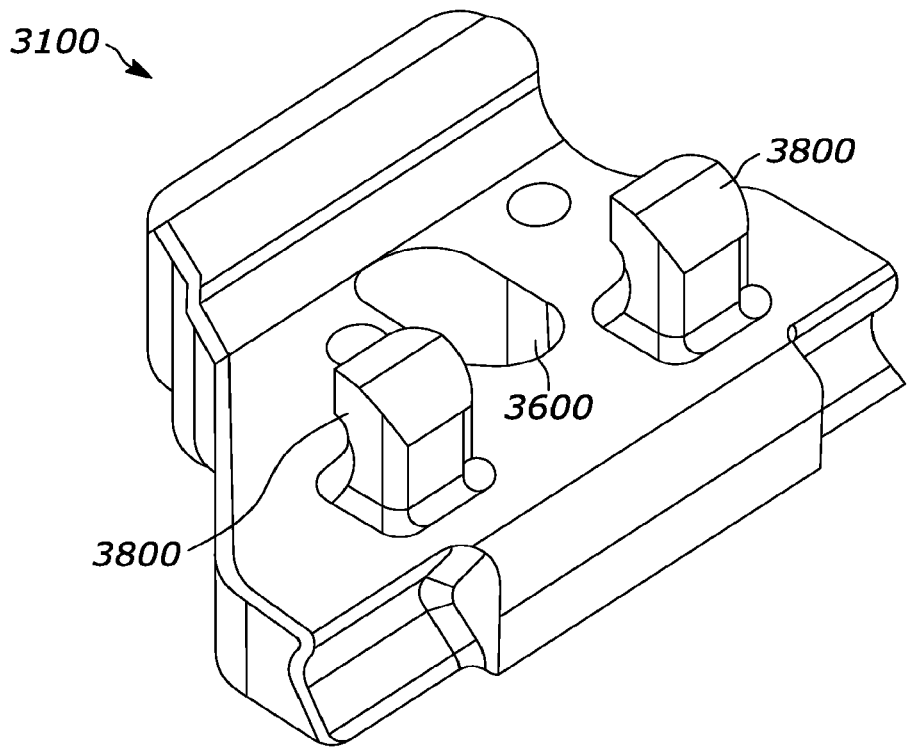
FIGS. 30A-30D show various views of a second example proximal pad that may be used on a RIVAR plate consistent with present principles.
Figure 30B:
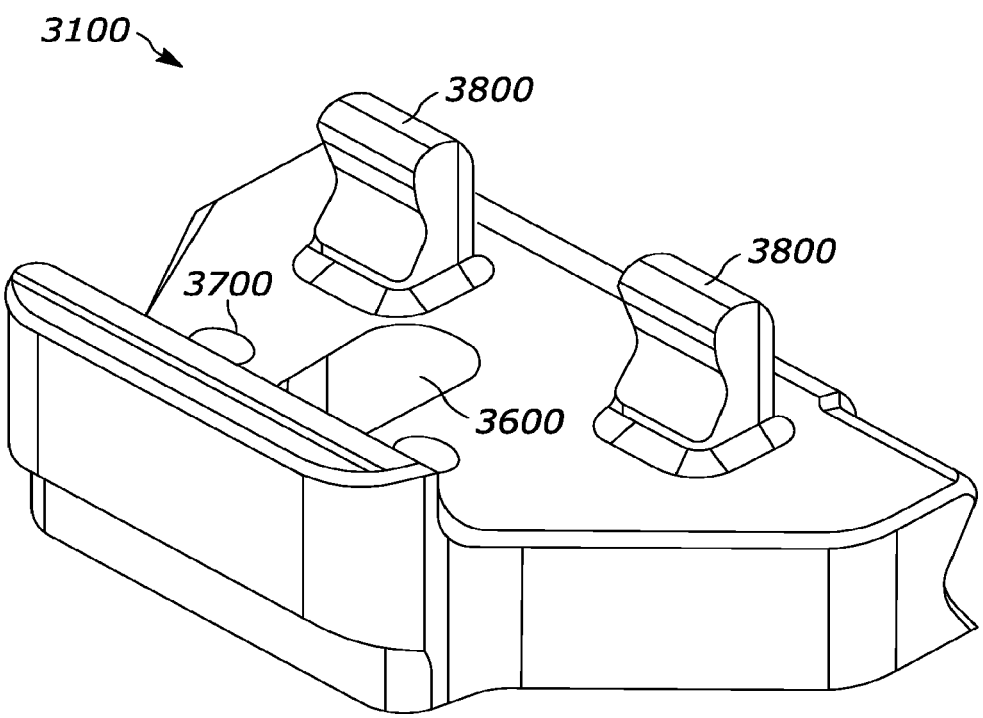
Figure 30C:
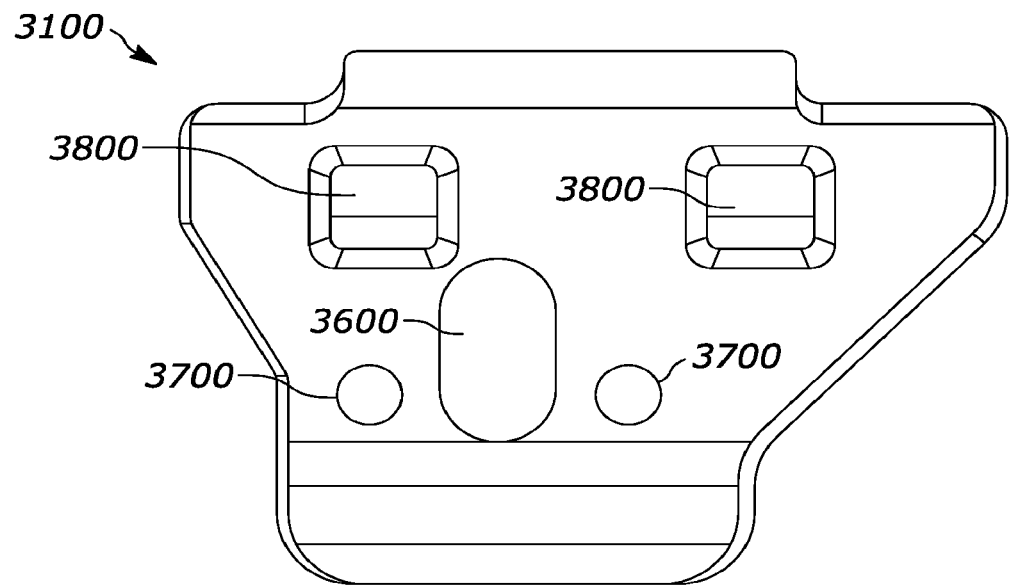
Figure 30D:
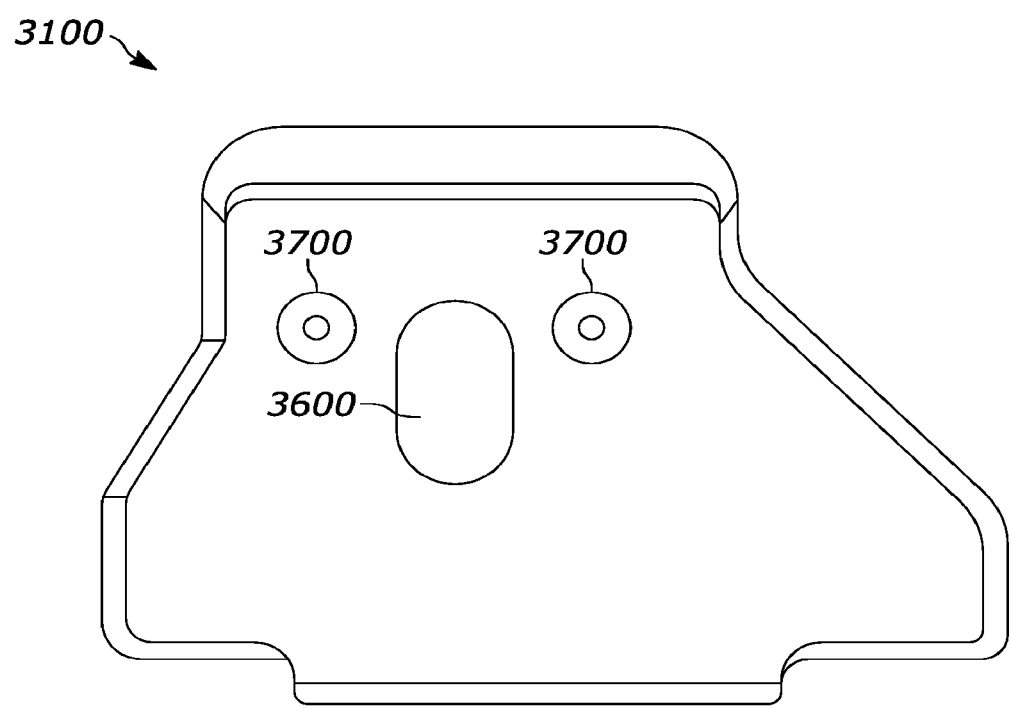
Figure 31A:
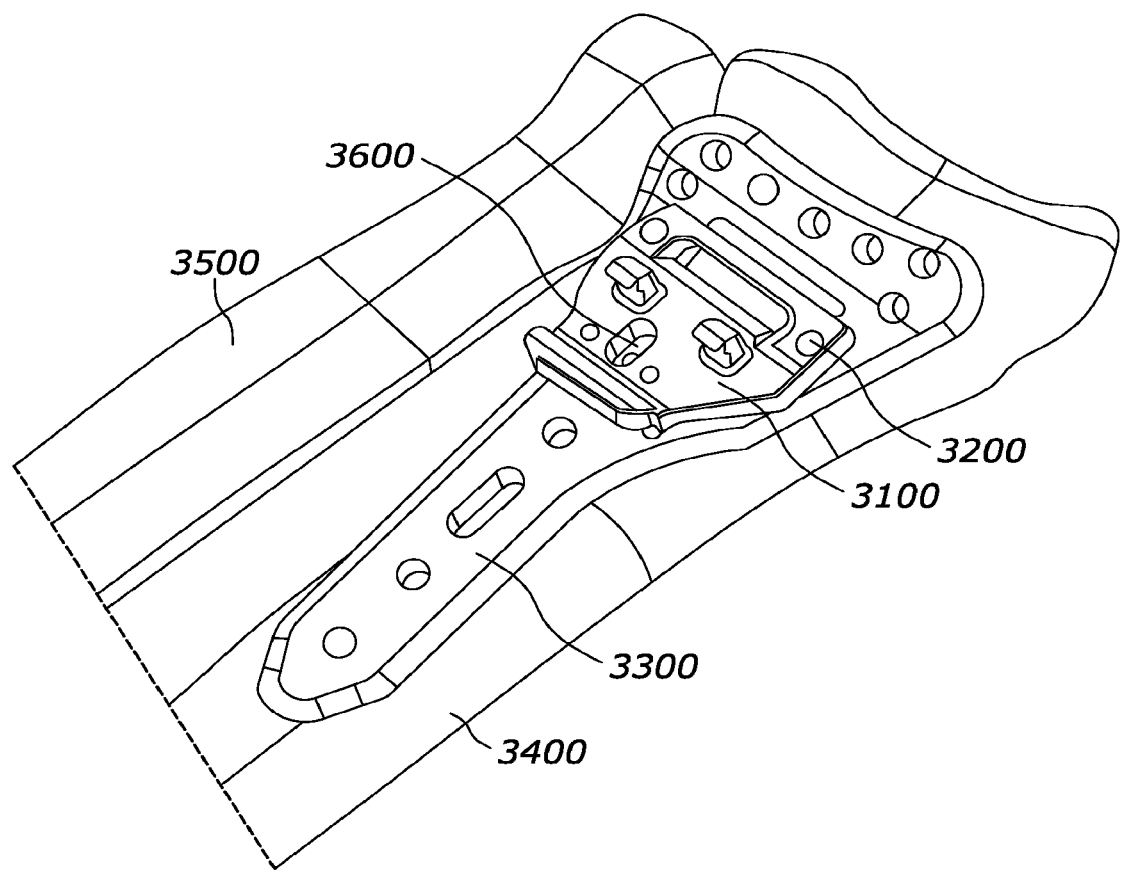
FIGS. 31A and 31B show different views of this second example proximal pad as coupled to a RIVAR plate along with a distal pad, with the RIVAR plate itself coupled to a distal radius of a patient consistent with present principles.
Figure 31B:
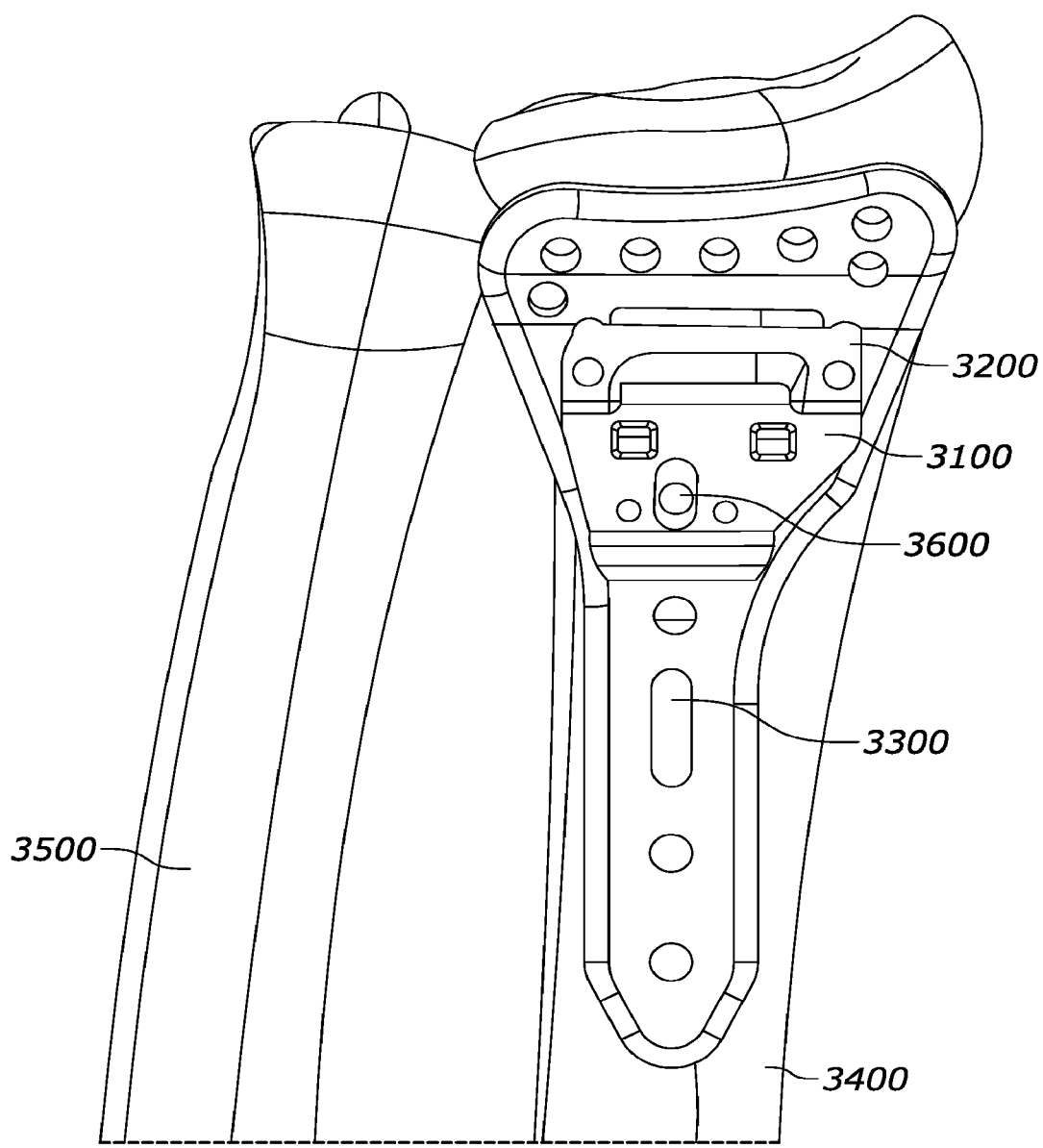

Reference is now made to FIGS. 30A-30D and 31A-31B, which show another example proximal pad 3100. FIGS. 30A and 30B show front and rear perspective views of the pad 3100, FIG. 31C shows a volar side plan view of the pad 3100, and FIG. 31D shows a dorsal side plan view of the pad 3100. FIGS. 31A-31B then show the proximal pad 3100 engaged with a distal pad 3200, with both being removably engaged with a RIVAR plate 3300 mounted to a patient's radius 3400 consistent with present principles (with an ulna 3500 also being shown).

The pad 3100 may be the same as the pad 1100 save for having a hole 3600 extending volar-dorsal through the pad 3100. The hole 3600 may extend volar-dorsal through the pad 3100 between the pegs 3700 and hooks 3800 as shown, generally in the middle of the body portion of the pad 3100. This slot/hole 3600 may be used to leverage a spike or screw on a volar face of the plate 3300 into the hole 3600 to help secure/lock down the proximal pad 3100, since the spike or screw is affixed to the plate 3300 and/or radial bone and can help anchor the pad 3100 to the plate 3300. The hole 3600 therefore allows the pad 3100 to be tightened down/snapped onto the plate 3300 while affording space for the head of a fastener 125 to extend from dorsal to volar into the hole 3600.

Now in reference to FIGS. 32A and 32B, they show example perspective and side elevational views of an example sliding osteotome 3200 that may be used consistent with present principles. Also note that features of the osteotome 3200 may be combined with the features of the osteotome 2600 (e.g., include fanning capability).

The sliding osteotome 3200 may be composed of a flat, integral bar with a proximal portion 3210 and a distal portion 3220. As shown, a distal end of the distal portion 3220 may be bi-beveled such that the front and back faces slope inward toward the middle as they extend distally. The bar that may be made of titanium, titanium alloy, stainless steel, cobalt chrome, iron, cobalt, chromium, other metal alloys, tantalum, polyethylene, acrylic, other polymers/plastics, and/or ceramics etc. The bar may be longer longitudinally than wide width-wise. A slider 3230 may slide longitudinally up and down the bar through upper and lower faces of the slider 3230 when the slider 3230 is not locked in place. The slider 3230 may be made of the same material as the bar itself.

The slider 3230 may also include a set/compression screw 3240. The set screw 3240 may screw in and out transversely from front to back. The screw 3240 may therefore be screwed in to extend the screw 3240 onto or through either of the proximal or distal portion 3210, 3220 of the bar to clamp down on an area of the bar inside the slider 3230 (e.g., establishing a screw fit, friction fit, and/or compressed locking fit between the interlocked slider 3230 and portion 3210/3220). Setting the set screw 3240 may therefore lock the bar with respect to the slider 3230 after the slider 3230 is slid longitudinally along the bar in an axis parallel to the longitudinal axis of the bar itself to a desired length. Thus, in at least some example embodiments, the portions 3210, 3220 may have screw tracks or screw holes spaced longitudinally from each other along middle sections of the bar's front face to receive the screw 3240 and lock the slider 3230 with respect to the osteotome bar.

Note that the sliding osteotome 3200 may also include one or more extension bars 3250 extending laterally from the osteotome 3200. The bars 3250 may hook into a hook of a proximal pad consistent with present principles, such as the hook 2810 of the proximal pad 1100, after a desired osteotome depth that is to be used for fracture reduction is set by a physician using the slider 3230 and screw 3240. Thus, further note here with respect to FIGS. 32A and 32B that at least respective front faces of the portions 3210, 3220 of the bar may include ruler/length markings spaced longitudinally thereon (as shown, expressed in centimeters) to aid a surgeon in determining a set length for the osteotome 3200. Once the desired length is set via sliding the slider 3230 to a desired length and locking the locking screw 3240, the surgeon may place the bars 3250 within the hooks 2810 to use the radius-mounted plate 100 and hooks 2810 to maintain the osteotome 3200 at the desired volar-dorsal depth to aid the surgeon for fracture reduction.

Before describing FIG. 33, note with respect to the principles of FIGS. 32A and 32B that an osteotome standard peg to tip depth may be 2.5 cm, which may match the average distance from the plate to the dorsal cortex.

Moving on to FIG. 33, an example Reduction Chart 3300 that may be used consistent with present principles is shown. The chart 3300 may include a left-most column of respective thicknesses of either a plate by itself (top row) or with proximal and distal pads of various volar-dorsal thicknesses being used. And note that pad thickness may exclude any segments of the peg(s), hooks, and/or extension elements (e.g., 1160, 1670, 1170, 1180) extending away from respective dorsal or volar faces of the respective pads themselves.

Subsequent columns in the chart 3300 set forth osteotome excursion by degree, dorsal cortical correction (lengthening), true dorsal cortical correction, volar cortical correction (lengthening), and true volar cortical correction. Note that true correction/subtraction may be a calculated correction minus thirty percent to compensate for compressibility of the radial bone.

Figure 34:
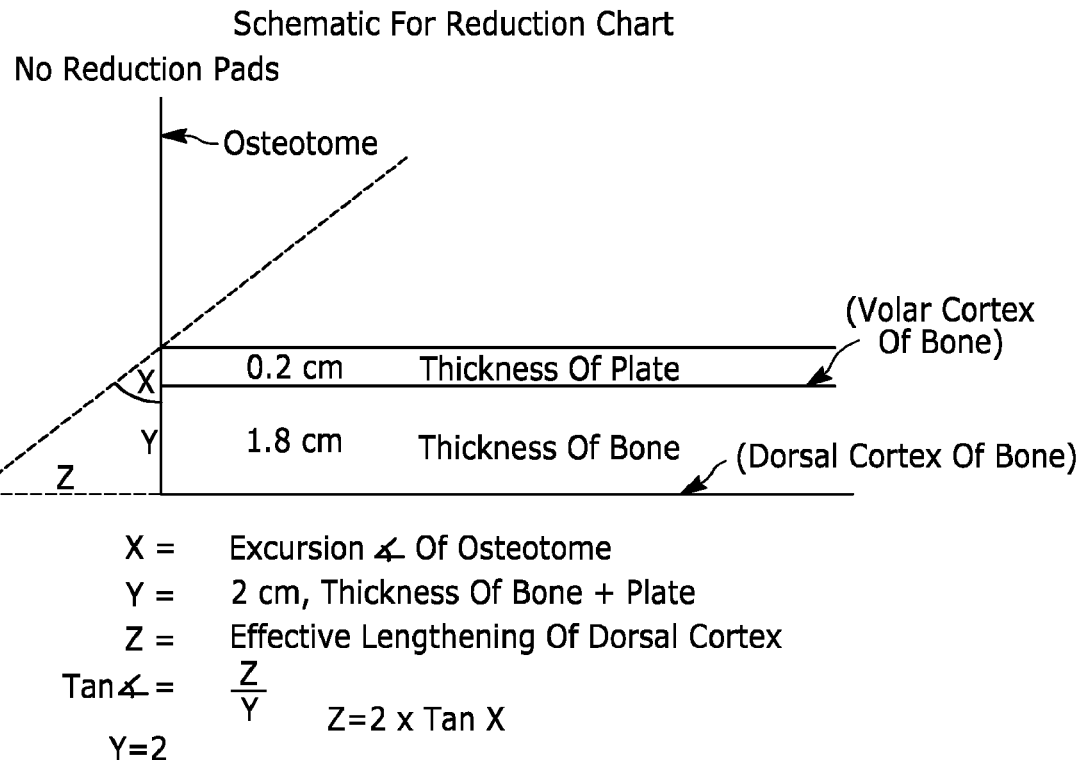
FIGS. 34 and 35 show example schematics illustrating present principles in accordance with the reduction charge of FIG. 33.
Figure 35:
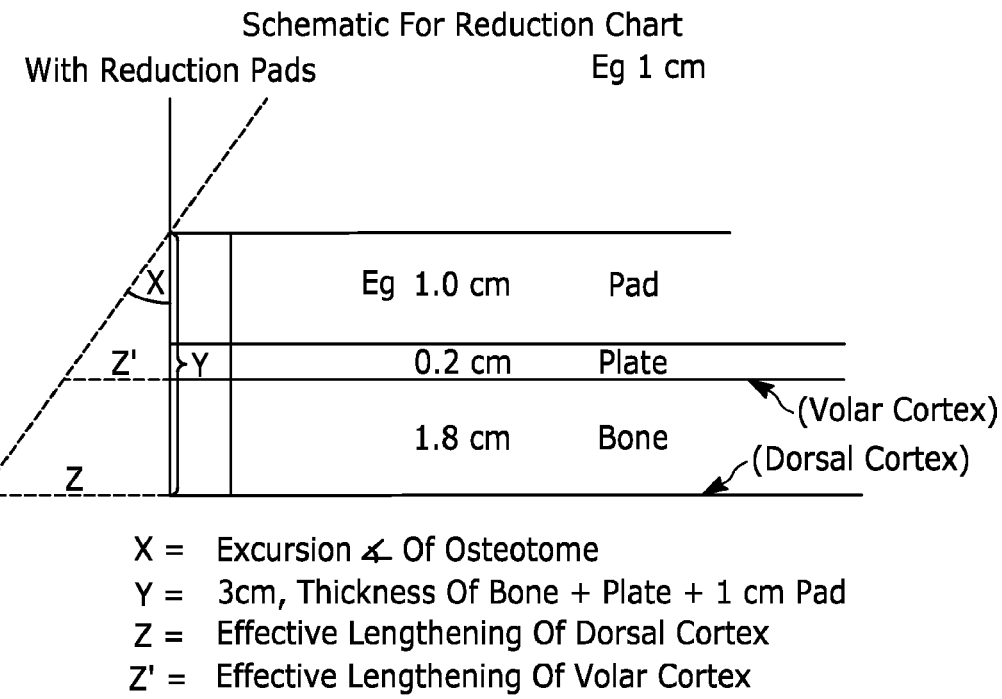

It is therefore recognized consistent with present principles that factors affecting lengthening of the dorsal/volar cortices may be the following: initial insertion angle of the osteotome, quality/compressibility of the bone, and angular excursion of the lever arm/osteotome. With this in mind, note that FIG. 34 shows a schematic per the Reduction Chart 3300 while no proximal and distal reduction pads are attached to a RIVAR plate consistent with present principles, while FIG. 35 shows a schematic per the Reduction Chart 3300 when proximal and distal pads of a 1 centimeter (cm) thickness are used. Also note here that the RIVAR plate itself may have a dorsal to volar thickness of 0.2 cm while an example radial bone may have a thickness of 1.8 cm. It may be appreciated from these two figures that in using proximal and distal pads with a plate per FIG. 35, rather than simply a plate by itself per FIG. 34, the effective lengthening of the dorsal cortex may be increased. Additionally, it may be further appreciated that use of pads of increasingly greater thicknesses may result in increasingly greater lengthening ability.

Also, note before concluding that in addition to methods of radial fracture reduction according to the above, and in addition to the physical components described above (including plate, pads, fasteners, and osteotome), present principles also relate to providing/vending a kit including some or all of the physical components described above. For instance, the kit may come with or without an osteotome but still include proximal pads of varying thickness, and distal pads of varying thickness in one or both of single-bevel or dual-bevel form for increasing radial inclination. Fasteners may also be included, as may be different RIVAR plates for different arms and RIVAR plates different lengths and thickness for each arm. Also note that any and all components described herein may be manufactured by injection molding, 3D printing, etc.

While particular techniques are herein shown and described in detail, it is to be understood that the subject matter which is encompassed by the present invention is limited only by the claims.

Components included in one embodiment can be used in other embodiments in any appropriate combination. For example, any of the various components described herein and/or depicted in the Figures may be combined, interchanged, or excluded from other embodiments.

"A system having at least one of A, B, and C" (likewise "a system having at least one of A, B, or C" and "a system having at least one of A, B, C") includes systems that have A alone, B alone, C alone, A and B together, A and C together, B and C together, and/or A, B, and C together, etc.

What is claimed is:
1. A device, comprising:
a shank defining a proximal-distal dimension and formed with plural longitudinally-spaced holes for accepting respective bone fasteners;

a window portion made integrally with the shank and extending distally away from a distal end of the shank, the window portion defining a dorsal surface and a volar surface opposite the dorsal surface, the window portion defining an ulna-radius dimension generally perpendicular to the proximal-distal dimension, the window portion comprising an ulnar wall and a radial wall opposite the ulnar wall, at least the radial wall tapering radially from the distal end of the shank, a cross-member connecting distal ends of the radial and ulnar walls to form a window with a periphery between the radial and ulnar walls and the cross-member, the cross-member being wider in the ulna-radius dimension than the shank; and at least a first proximal pad removably engageable with the shank, the first proximal pad comprising plural pegs each engageable with a respective hole in the shank, the plural pegs extending from a dorsal side of the first proximal pad, the first proximal pad comprising plural extension elements extending from a volar side of the first proximal pad, the plural extension elements spaced from each other, each extension element comprising a respective curved end portion, each curved end portion configured for receiving a portion of one or more bars extending laterally from an osteotome.

2. The device of claim 1, wherein at least a distal portion of the window portion is angled or curved volarly.

3. The device of claim 1, wherein the radial wall of the window portion extends further radially than the ulnar wall extends ulnarly.

4. The device of claim 1, further comprising at least a first distal pad removably engageable with the window portion.

5. The device of claim 4, wherein the first distal pad comprises at least one peg engageable with a respective hole in the window portion.

6. The device of claim 4, wherein the first distal pad comprises a distal face that is at least partially curved or beveled distally.

7. The device of claim 4, wherein the first distal pad comprises a proximal edge portion.

8. The device of claim 7, wherein the proximal edge portion comprises a proximal edge establishing a lip, the lip extending in the ulna-radius dimension.

9. The device of claim 7, wherein the proximal edge portion comprises a proximal wall beveled distally, the proximal wall of the proximal edge portion configured to engage the osteotome.

10. The device of claim 9, wherein the proximal wall is beveled distally and also beveled radially.

11. The device of claim 9, wherein the proximal wall is beveled distally but not beveled in the ulnar-radial dimension.

12. The device of claim 1, wherein the first proximal pad comprises a distal edge portion against which the osteotome can be disposed, the distal edge portion establishing a fulcrum for the osteotome.

13. The device of claim 1, comprising the osteotome, the osteotome configured to extend through the window portion to provide leverage to reduce a bone fracture.

14. The device of claim 1, wherein the cross-member comprises plural holes configured to accept at least one fixation wire.

15. A device, comprising:
a shank defining a proximal-distal dimension and formed with plural longitudinally-spaced holes for accepting respective bone fasteners;
a window portion made integrally with the shank and extending distally away from a distal end of the shank, the window portion defining a dorsal surface and a volar surface opposite the dorsal surface, the window portion defining an ulna-radius dimension, the window portion comprising an ulnar wall and a radial wall opposite the ulnar wall, the window portion comprising a cross-member connecting distal ends of the radial and ulnar walls; and
at least a first pad removably engageable with the shank, the first pad comprising plural extension elements extending from a volar side of the first pad, the plural extension elements spaced from each other, each extension element of the plural extension elements comprising a respective end portion, each respective end portion configured for receiving a portion of one or more components extending from an osteotome.

16. The device of claim 15, wherein the window portion comprises a distal end portion that extends volarly and obliquely away from a proximal portion of the window portion, the shank comprising at least a first hole configured to receive a first peg of the first pad, the window portion comprising at least a second hole configured to receive a second peg of a second pad, the first and second holes being different from each other and being different from the plural longitudinally-spaced holes.

17. The device of claim 16, comprising the second pad, wherein the second pad comprises a proximal edge portion, the proximal edge portion comprising a proximal wall beveled distally and also beveled radially, the proximal wall of the proximal edge portion configured to engage the osteotome.

18. The device of claim 15, comprising the osteotome.

19. The device of claim 15, wherein the one or more components comprise one or more bars.

20. A method, comprising:
providing a device, the device comprising a shank and a window portion, the shank defining a proximal-distal dimension and formed with plural longitudinally-spaced holes for accepting respective bone fasteners, the window portion made integrally with the shank and extending distally away from the shank, the window portion defining a dorsal surface and a volar surface opposite the dorsal surface, the window portion defining an ulna-radius dimension, the window portion comprising an ulnar wall and a radial wall opposite the ulnar wall, the window portion comprising a cross-member connecting distal ends of the radial and ulnar walls; and
providing at least a first pad removably engageable with the shank, the first pad comprising plural extension elements extending from a volar side of the first pad, the plural extension elements spaced from each other, each extension element of the plural extension elements comprising a respective end portion, each respective end portion configured for receiving a portion of one or more components extending from an osteotome.

* * * * *